(12) United States Patent
Sopher et al.

(10) Patent No.: US 11,185,438 B2
(45) Date of Patent: Nov. 30, 2021

(54) PESSARY FOR PELVIC ORGAN PROLAPSE

(71) Applicant: Reia, LLC, Lyme, NH (US)

(72) Inventors: Ariana M. Sopher, Somerville, MA (US); Kaitlin E. Maier, Cambridge, MA (US); Meegan P. Daigler, Brooklyn, NY (US); Paul D. Hanissian, Lyme, NH (US); Dana L. Wieland, Los Angeles, CA (US); Callan R. M. George, Sunnyvale, CA (US); Juhi Kalra, San Francisco, CA (US); Sophie K. Sheeline, Hillsborough, CA (US)

(73) Assignee: REIA, LLC, Lyme, NH (US)

( * ) Notice: Subject to any disclaimer, the term of this patent is extended or adjusted under 35 U.S.C. 154(b) by 281 days.

(21) Appl. No.: 16/141,955

(22) Filed: Sep. 25, 2018

(65) Prior Publication Data

US 2019/0091062 A1 Mar. 28, 2019

Related U.S. Application Data

(60) Provisional application No. 62/563,443, filed on Sep. 26, 2017.

(51) Int. Cl.
*A61F 2/04* (2013.01)
*A61F 6/08* (2006.01)

(52) U.S. Cl.
CPC .................... *A61F 6/08* (2013.01)

(58) Field of Classification Search
CPC ...... A61F 6/06; A61F 6/08; A61F 6/12; A61F 2/0004; A61F 2/0006; A61F 2/0022; A61F 2/005; A61F 2/06; A61F 2/0031; A61F 2/0036
See application file for complete search history.

(56) References Cited

U.S. PATENT DOCUMENTS

| 2,422,377 A | 6/1947 | Waterbury |
| 3,626,942 A | 12/1971 | Waldron |
| 4,677,967 A | 7/1987 | Zartman |
| 5,014,722 A | 5/1991 | Bauer |

(Continued)

FOREIGN PATENT DOCUMENTS

| GB | 1121925 A | 7/1968 |
| JP | 06133996 | 5/1994 |

(Continued)

OTHER PUBLICATIONS

International Search Report for PCT/US2018/052851 dated Jan. 16, 2019, 15 pages.

*Primary Examiner* — Camtu T Nguyen
(74) *Attorney, Agent, or Firm* — Barlow, Josephs & Holmes, Ltd.

(57) ABSTRACT

A collapsible pessary is provided, and can have a stem and at least one rotating petal member that can rotate between a collapsed state with a smaller diameter and a deployed state with a larger diameter. The collapsible pessary can have a plunger within the stem, and pushing the plunger upwards can cause the plunger to push upwards on a portion of the petal member, thereby causing the petal member to rotate into a deployed position. The pessary can be in a collapsed state wherein its overall diameter is at a minimum, or a deployed state, wherein its overall diameter is at a maximum.

15 Claims, 47 Drawing Sheets

(56) References Cited

U.S. PATENT DOCUMENTS

| | | |
|---|---|---|
| 6,503,190 B1 | 1/2003 | Ulmsten et al. |
| 6,530,879 B1 | 3/2003 | Adamkiewicz |
| 6,645,137 B2 | 11/2003 | Ulmsten et al. |
| 8,127,768 B2 | 3/2012 | Ziv |
| 8,302,608 B2 | 11/2012 | Harmanli |
| 8,651,109 B2 | 2/2014 | Ziv et al. |
| 8,728,013 B2 | 5/2014 | Perle et al. |
| 8,840,598 B2 | 9/2014 | Minoguchi et al. |
| 8,888,676 B2 | 11/2014 | Ziv et al. |
| 8,919,345 B2 | 12/2014 | Avery, Jr. et al. |
| 8,926,493 B2 | 1/2015 | Karapasha |
| 9,078,726 B2 | 7/2015 | Karapasha |
| 9,211,211 B2 | 12/2015 | Maurette |
| 9,320,640 B2 | 4/2016 | Durling et al. |
| 9,339,364 B2 | 5/2016 | Durling et al. |
| 9,393,090 B2 | 7/2016 | Karapasha |
| 9,402,703 B2 | 8/2016 | Ziv et al. |
| 9,433,523 B2 | 9/2016 | Avery, Jr. et al. |
| 9,439,748 B2 | 9/2016 | Durling et al. |
| 9,555,168 B2 | 1/2017 | Browning |
| 9,597,222 B2 | 3/2017 | Durling et al. |
| 9,649,219 B2 | 5/2017 | Strong et al. |
| 9,655,769 B2 | 5/2017 | Ziv et al. |
| 9,717,582 B2 | 8/2017 | Arcand et al. |
| 9,744,630 B2 | 8/2017 | Avery, Jr. et al. |
| 10,039,666 B2 | 8/2018 | Ziv et al. |
| 10,143,598 B2 | 12/2018 | Strong et al. |
| 10,188,545 B2 | 1/2019 | Conti |
| 10,201,411 B2 | 2/2019 | Ramachandran et al. |
| 10,335,312 B2 | 7/2019 | Williams et al. |
| 10,405,959 B2 | 9/2019 | Ziv |
| 10,617,503 B2 | 4/2020 | Rosen et al. |
| 2009/0266367 A1 | 10/2009 | Elan |
| 2013/0025604 A1 | 1/2013 | Oz |
| 2013/0327338 A1 | 12/2013 | Churchill et al. |
| 2016/0235583 A1 | 8/2016 | Durling et al. |
| 2017/0100278 A1 | 4/2017 | Ziv et al. |
| 2017/0224457 A1 | 8/2017 | Strong et al. |
| 2018/0296387 A1 | 10/2018 | Ziv et al. |
| 2018/0296388 A1 | 10/2018 | Ziv et al. |
| 2019/0053937 A1 | 2/2019 | Meyer |
| 2019/0091062 A1 | 3/2019 | Sopher et al. |
| 2019/0336260 A1 | 11/2019 | Price et al. |

FOREIGN PATENT DOCUMENTS

| | | |
|---|---|---|
| WO | 2004103213 | 12/2004 |
| WO | WO 2014/103213 A1 * | 12/2004 |
| WO | 2008079271 A1 | 7/2008 |
| WO | 2017064713 | 4/2017 |
| WO | 2020205614 A1 | 10/2020 |

* cited by examiner

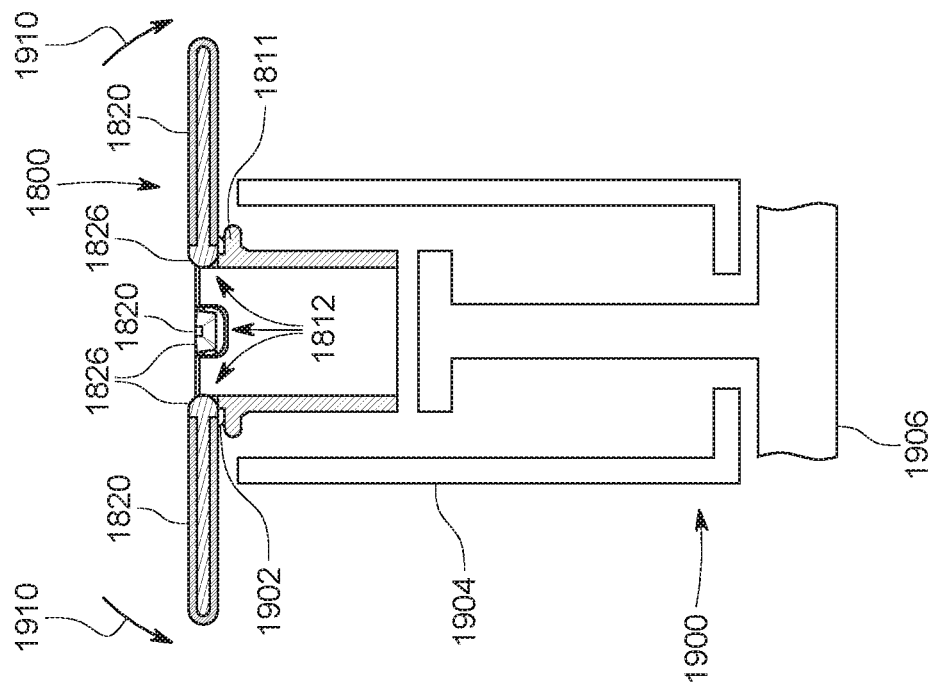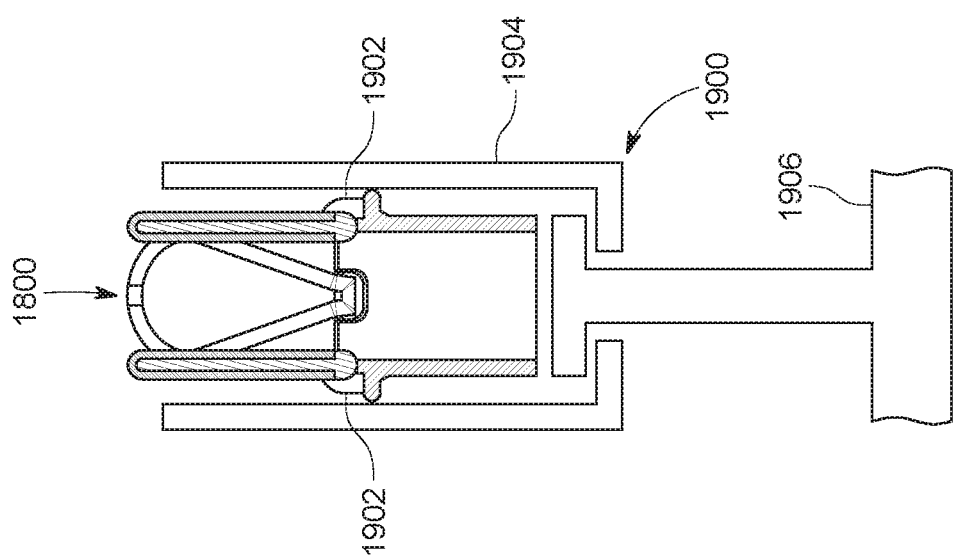

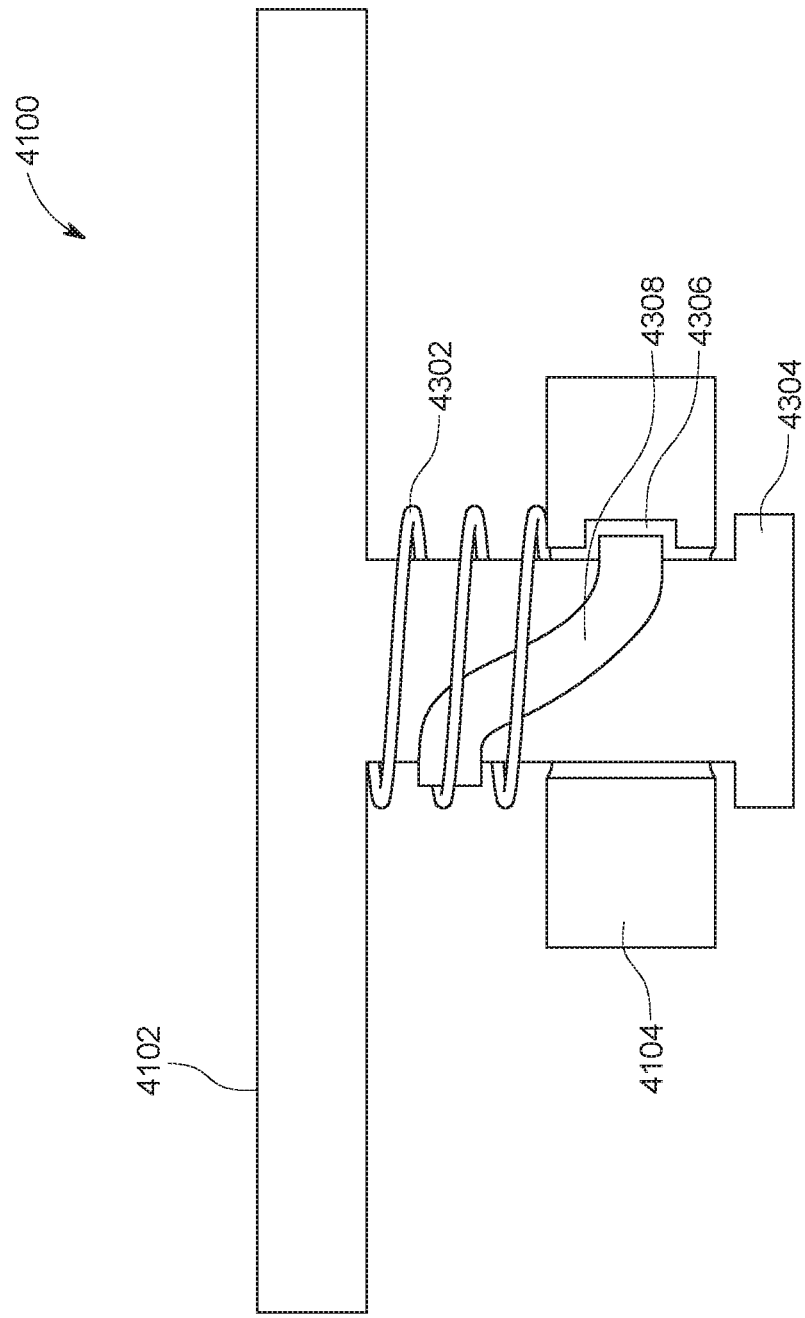

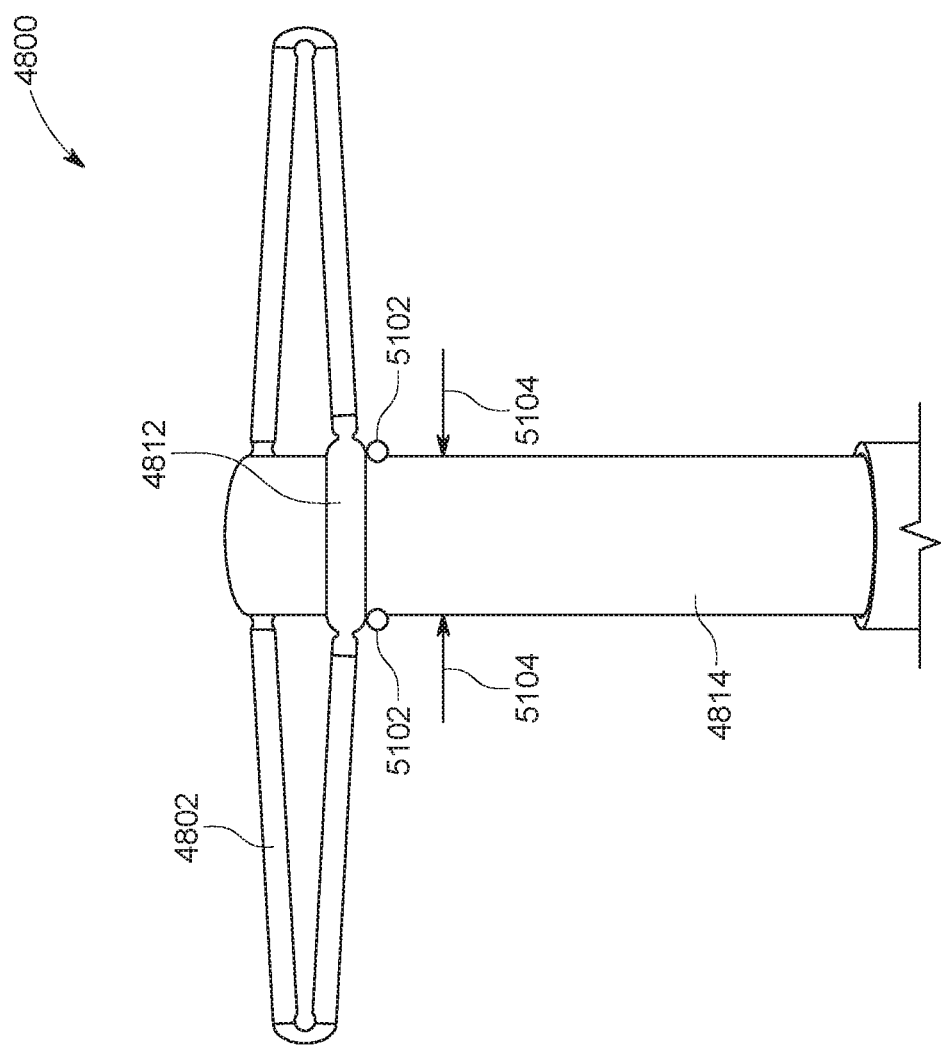

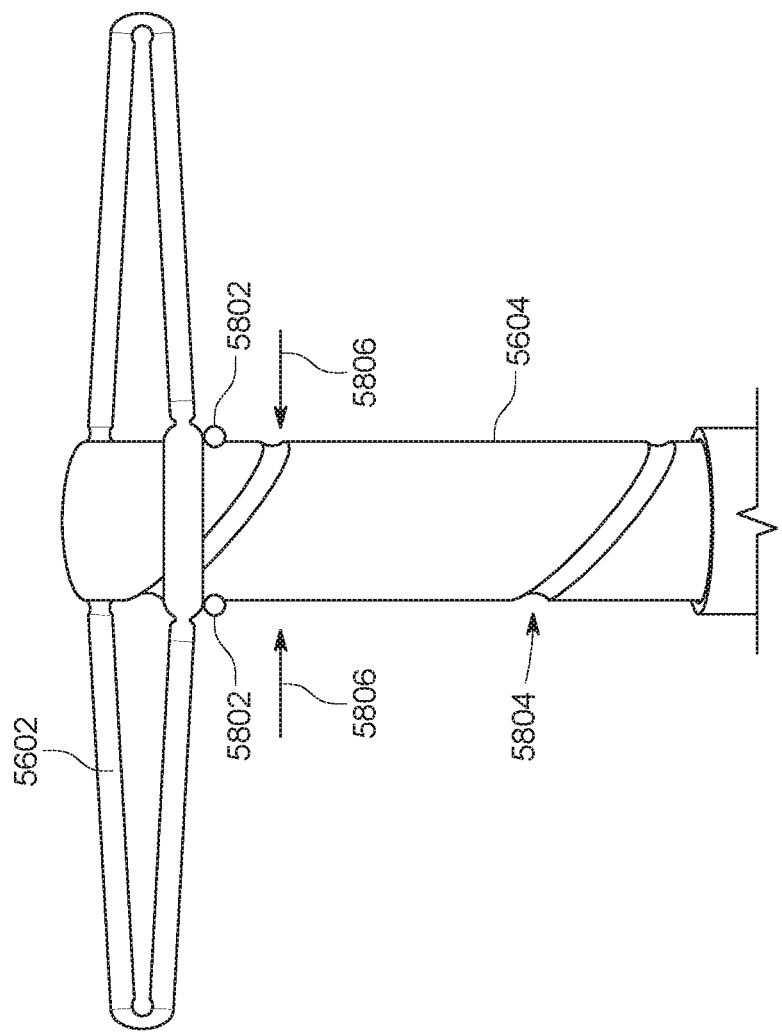

PESSARY FOR PELVIC ORGAN PROLAPSE

RELATED APPLICATION

This application claims the benefit of U.S. Provisional Application Ser. No. 62/563,443, entitled PESSARY FOR PELVIC ORGAN PROLAPSE, filed Sep. 26, 2017, the teachings of which are incorporated herein by reference.

FIELD OF THE INVENTION

This invention relates to pessaries for use in treating pelvic organ prolapse, and more specifically, to removable pessaries

BACKGROUND OF THE INVENTION

About 50 percent of women over the age of 50 suffer from some degree of pelvic organ prolapse ("POP"). The female pelvic organs include the bladder, uterus, vaginal canal and rectum. A prolapse is a medical condition in which at least one organ of the body has slipped forward or downward. Pelvic organ prolapse can result from weakening of the pelvic floor muscles and loss of integrity of the pelvic floor connective tissue of which allows for abnormal uterine or vaginal descent. In certain cases, the uterus can descend through the opening to the vaginal canal. Contributory factors for POP can include hard labors with long episodes of pushing, large babies, smoking, obesity, connective tissue disorders, upper respiratory disorders and repetitive strain injuries. The severity of POP can range from minor and asymptomatic to more severe degrees requiring medical intervention. In the latter case, women can choose to undergo reconstructive surgery using a surgically implanted mesh or a native tissue repair to resuspend the fallen structures. Alternatively, women can manage non-surgically with a pessary.

FIG. 1 of the prior art presents a case of POP in which certain of the pelvic organs have descended from a female pelvic region 100. The female pelvic region 100 is shown in a side view such that the front side 102 is oriented to the left and the rear side 104 is to the right. The pelvic region 100 is supported by a skeletal frame 106. A plurality of prolapsed organs 108 have descended from the pelvic region below the pelvic floor axis 109 that corresponds to a plane running from front to rear along the bottom of the pelvic region. Ordinarily, the pelvic organs are disposed above axis 109. The prolapsed organs 108 that have descended below axis 109 to include a bladder 110, a uterus 112 and the vaginal canal 114. In the case of the vaginal canal 114, this organ has become inverted, such that the interior lining is now an exterior surface, to the great discomfort of the person for whom it is an ordinary recessed organ. A rectum 116 remains situated above axis 109, but it is contemplated that eventually, it can descend through axis 109 to join the other prolapsed organs 108.

A pessary is a device that can be inserted into the vaginal canal to support the descending organs. Pessaries can be recommended for women who do not wish to undergo surgery, for pregnant women, or for women with other serious health issues which makes surgery too risky. Pessaries are primarily made of medical grade silicone, with some containing internal plastic support structures for added rigidity. In function, the pessary resides in the vaginal canal and provides vertical support for the uterus, as well as lateral support for the bladder and/or rectum, if also prolapsed.

FIG. 2 of the prior art shows a pessary 200 inserted into the vaginal canal 114 to support the prolapsed organs 108 of FIG. 1. The pessary 200 can be placed in the vaginal canal 114 just above axis 109 and can stay in place due to residual tone of the pelvic floor muscle group 202 and at least one of a suction, a friction force and/or larger size (so as to cause the vaginal wall to indent around the perimeter of the pessary 200). When in position, the pessary supports the organs above it and prevents them from impinging upon or passing through the vaginal canal. However, pessaries can cause erosion of the vaginal lining (epithelium) if they are inappropriately sized or left in situ for prolonged periods. To fit a pessary, a healthcare practitioner (for example, a physician, a physician's assistant, a nurse or midwife) assesses the size of the vaginal canal, introitus (opening) 204 and depth. The pessary can be lubricated, inserted and positioned behind the pubic symphysis 206 (a bony structure in the skeletal frame 106). Pessaries in the prior art tend to be rigid and difficult to remove and re-insert by the user alone. Many women return to the practitioner every three to six months to have their pessary removed, cleaned and replaced. Some women are able to remove and clean their pessaries themselves. The recommendations for self-cleaning have not been standardized, but for example, current Canadian practice advises any woman who is able to remove her own pessary to remove, wash and replace it once per week. Pessaries can be cumbersome and uncomfortable to insert and remove. The average pessary user is a postmenopausal woman and these women often experience vaginal atrophy and dryness as well as narrowing of the vaginal canal introitus, creating the potential for further difficulty and discomfort of insertion and removal. Currently available pessaries are manually folded or compressed to some degree before insertion. Although this can be helpful with enhancing the ease and comfort of the insertion, currently available pessaries are not able to significantly decrease in cross-sectional area. During removal it can be difficult to fold the pessary, often resulting in the pessary being removed in its full or close to full size and shape. These attributes make self-maintenance of the pessary very painful, if not impossible, and consequently, only approximately 5% of women with a pessary are able to remove, clean, and insert their own pessaries. Furthermore, some pessaries are not removable by the patient at all.

The relative rigidity of pessaries and the difficulties in removal can result in a reliance on a healthcare practitioner for regular cleaning, an inability to experience vaginal intercourse and the pessary remaining inserted even when not necessary. It would be desirable for a pessary to be readily inserted and removed by the user, thereby improving the quality of life for that user.

SUMMARY OF THE INVENTION

A pessary overcomes the disadvantages of the prior art by providing a collapsible pessary that can be readily inserted, removed and cleaned without the assistance of a health practitioner. In an embodiment, a pessary can consist of a stem and at least one petal member hingedly attached to an insertion end of the stem. The at least one petal member can rotate between a collapsed state and a deployed state. In the deployed state, the at least one petal member can extend outward from the stem, and in the collapsed state, the at least one petal member can be rotated upwards so that the diameter of the pessary is smaller in the collapsed state than in the deployed state. The pessary can have a plunger that can move within the stem along a vertical axis of the stem, wherein the plunger can slide away from the insertion end of the stem to allow the at least one petal member to rotate upwards into the collapsed state, and the plunger can slide towards the insertion end of the stem to push the at least one petal member into the deployed state. When the plunger is pushed towards the insertion end of the stem, a top of the plunger pushes upwards on the short segment causing the at least one petal member to rotate into the deployed state with the elongated segment extending outwards from the stem. The pessary can include a connection between the top of the plunger and the short segment of the at least one petal member, and when the plunger is pulled away from the insertion end of the stem, the top of the plunger can pull the short segment inwards and downwards, thereby rotating the elongated segment upwards into the collapsed state. The pessary can include a shelf at the insertion end of the stem, so that when the pessary is in a deployed state, the at least one petal member can be supported by the shelf. The pessary can include at least one sliding hinge between the stem and the at least one petal member. The sliding hinge can be hingedly attached to the at least one petal member, and the sliding hinge can be slidably attached within the interior of the stem. The sliding hinge can slide along the interior of the stem in a direction parallel to the vertical axis. The pessary can include a deformable membrane that can be connected to and located between a plurality of short segments. The deformable membrane can be connected to the top of the plunger. The at least one short segment can be connected to the top of the plunger. The at least one petal member can include a tab at the bend, and the plunger cap can have at least one groove, so that when the pessary is in a deployed state, the tab can be engaged with the groove. The at least one petal member can include at least two petal members, and the pessary can include an outer rim, so that the outer rim connects the at least three petal members thereby forming a unitary petal member. The at least one petal member can include at least two petal members, and the pessary can include a petal webbing between the petal members, the petal members and the petal webbing forming a unitary petal member. The pessary can include a stem cap, and in a deployed position, the short segment can be held between the plunger and the stem cap, thereby preventing the petal member from rotating out of the deployed position. The petal members can include an intermediate segment, and in a deployed state, the plunger can prevent the short segment from rotating upwards, thereby preventing the petal member from over-rotating out of the deployed position, and the plunger can prevent the intermediate segment from rotating inwards, thereby preventing the petal member from rotating back to the collapsed state. In the collapsed state, the at least one petal member can be substantially parallel to a vertical axis of the stem.

In an embodiment, a method of inserting a pessary can include collapsing the pessary into a collapsed state by rotating an elongated member of at least one petal member upwards to decrease the diameter of the pessary; inserting the pessary into the vaginal canal; and pushing a plunger upwards into a stem of the pessary, so that a top of the plunger pushes against the petal members, thereby extending the petal members outwards into a deployed state.

In an embodiment, a method of removing a pessary can include pulling a plunger downwards from the stem of a pessary, thereby allowing petal members to rotate out of a deployed state; and pulling the pessary downwards, thereby allowing the petal members to rotate into a collapsed state, decreasing the diameter of the pessary; and removing the pessary from the vaginal canal.

BRIEF DESCRIPTION OF THE DRAWINGS

The invention description below refers to the accompanying drawings, of which:

FIG. 19 is a view of the pessary of FIG. 18 that can be operated without a plunger, shown in a deployed state according to an embodiment;

FIG. 43 is a cutaway view of a central pivoting hinge for the pessary of FIG. 41 showing inner workings and in a deployed state, according to another illustrative embodiment;

Figure 51C:
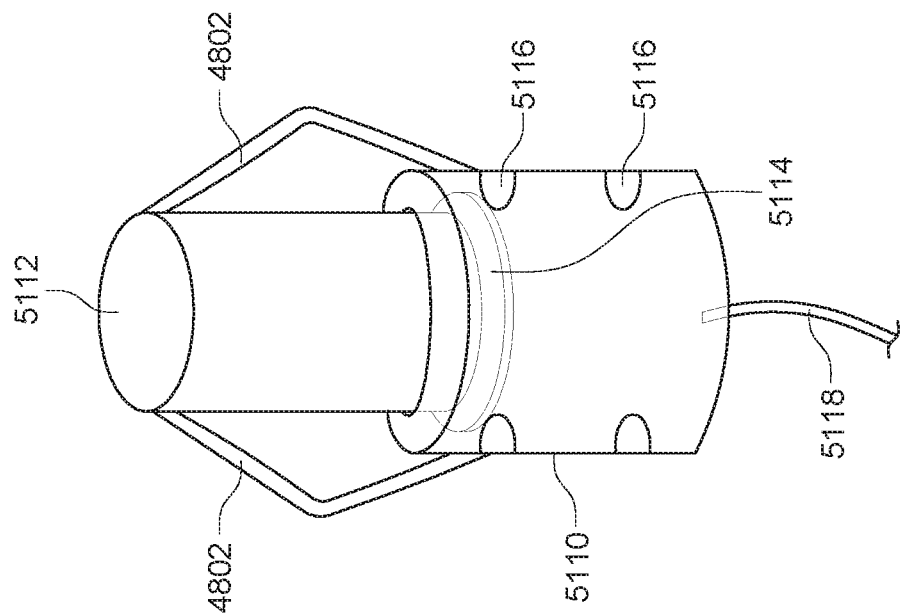
FIG. 51A is a perspective view of a locking mechanism for the pessary of FIG. 48, according to an illustrative embodiment.
FIG. 51B is a partially cut away perspective view of a locking mechanism for the pessary of FIG. 48 and shown in a deployed state, according to another illustrative embodiment.
Figure 51B:
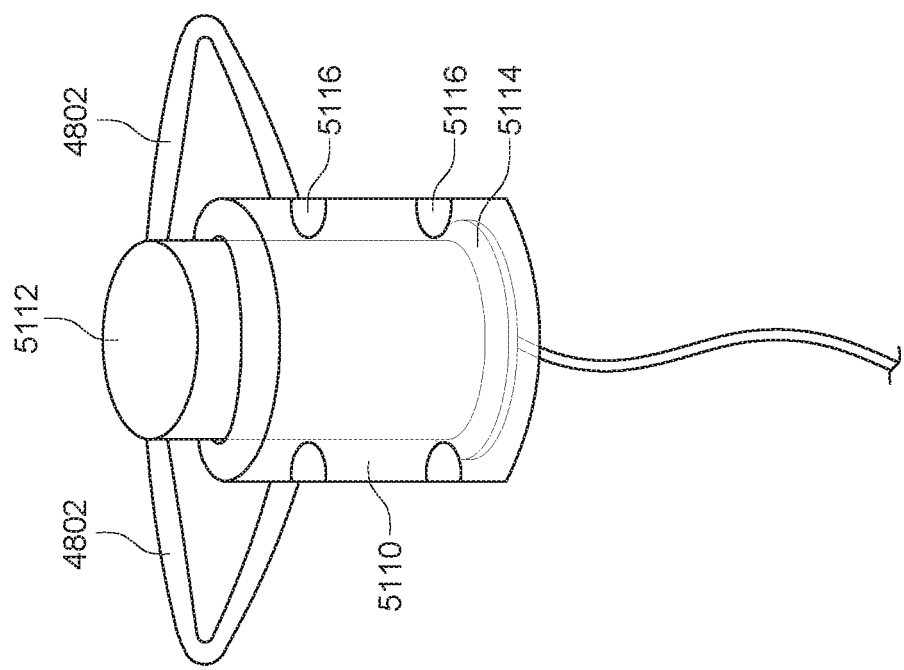
Figure 51E:
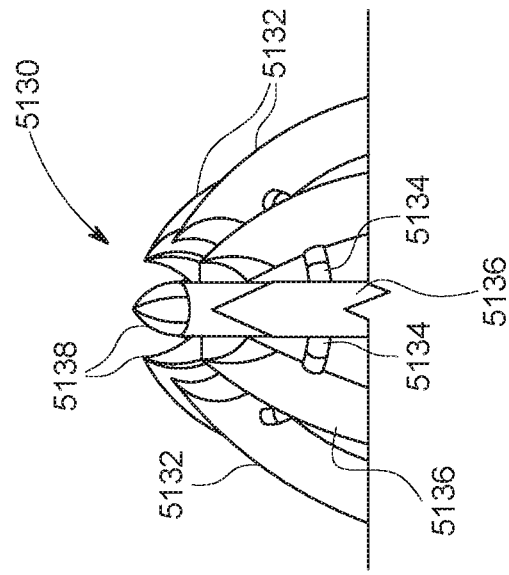
Figure 51D:
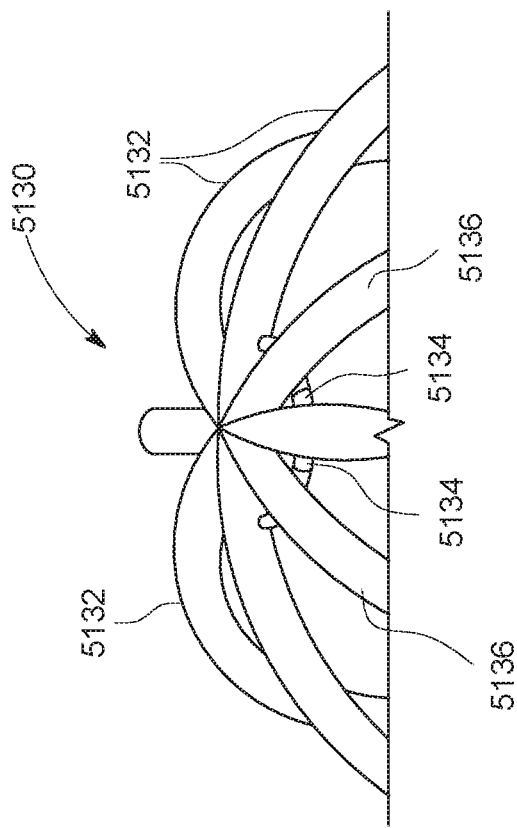
Figure 52:
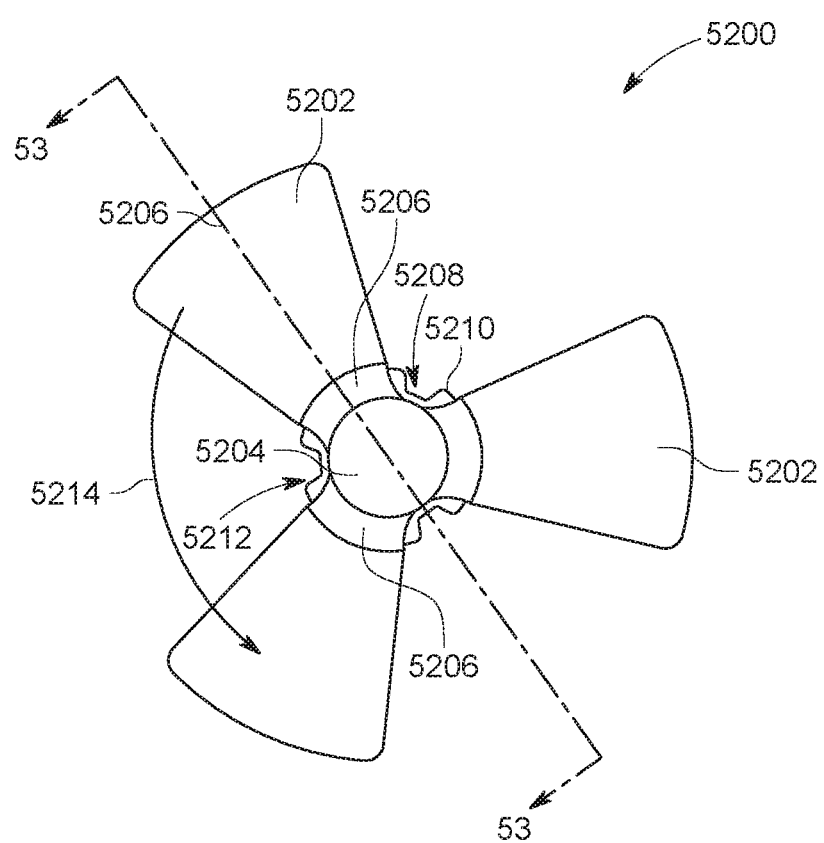
Figure 53:
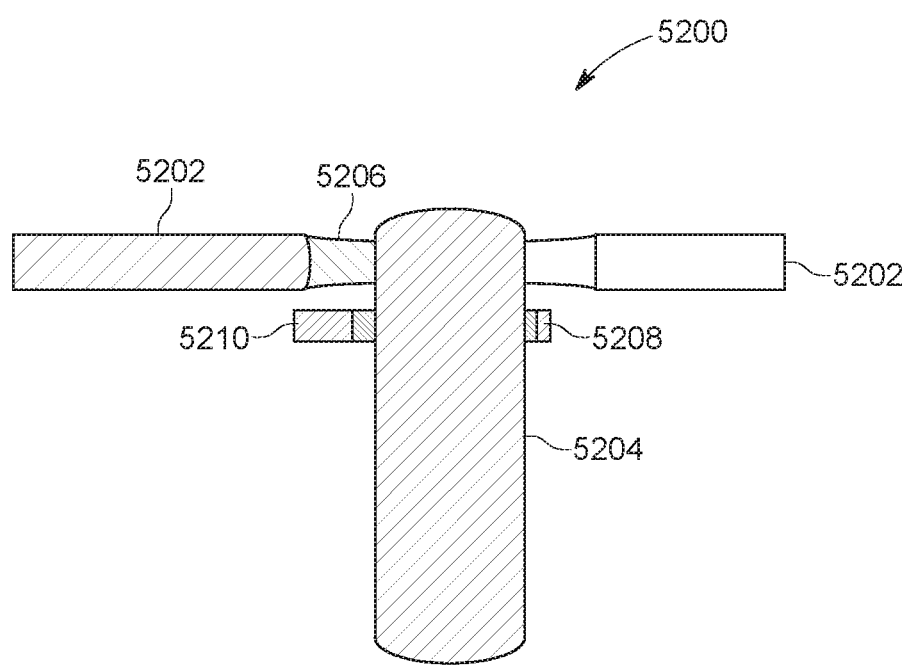
Figure 54:
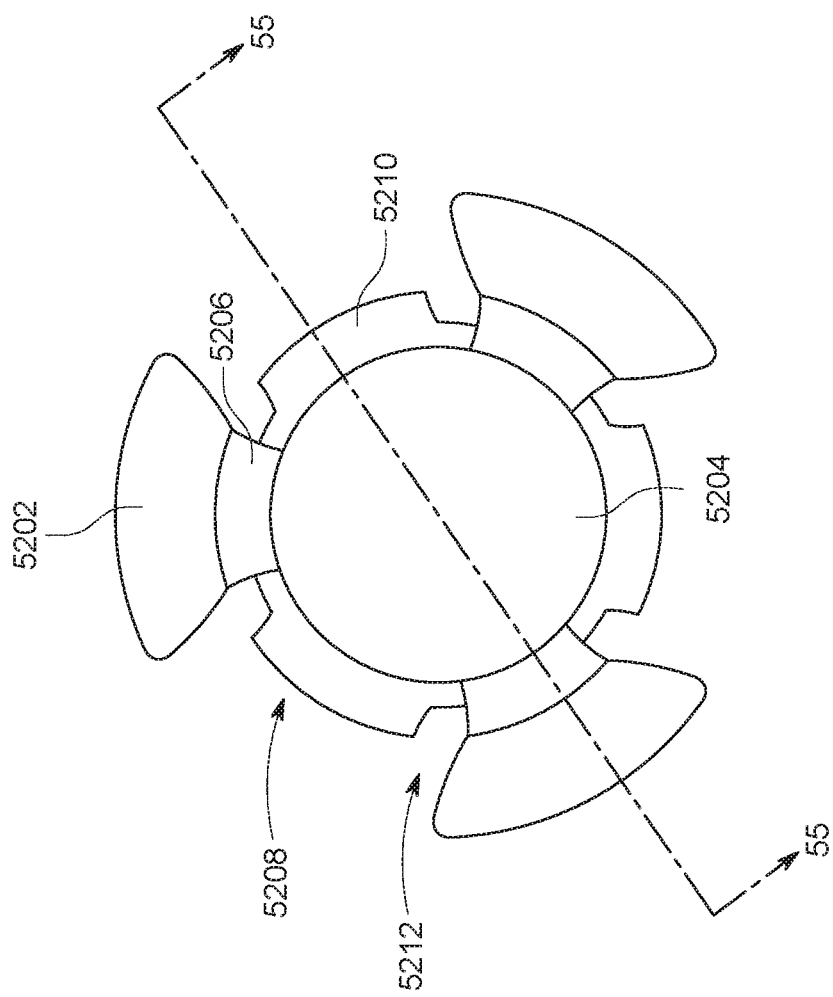
Figure 55:
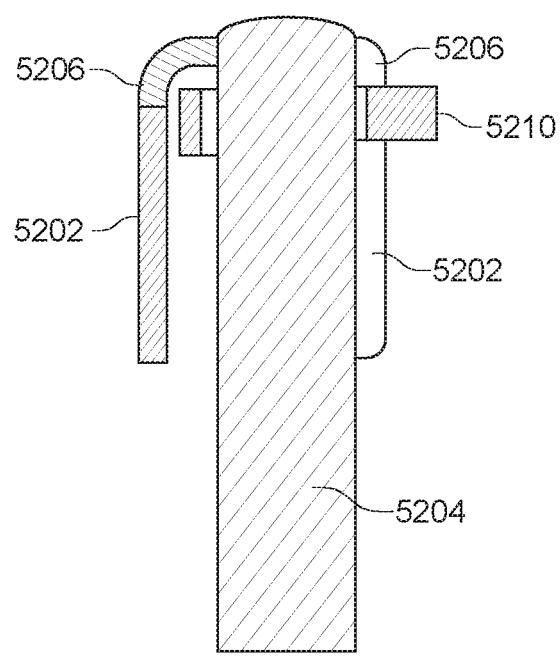
Figure 57:
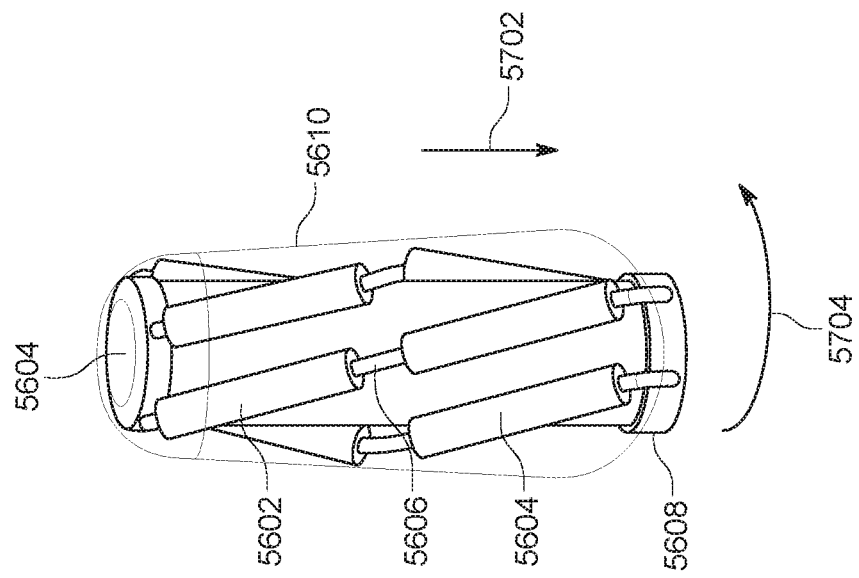
Figure 56:
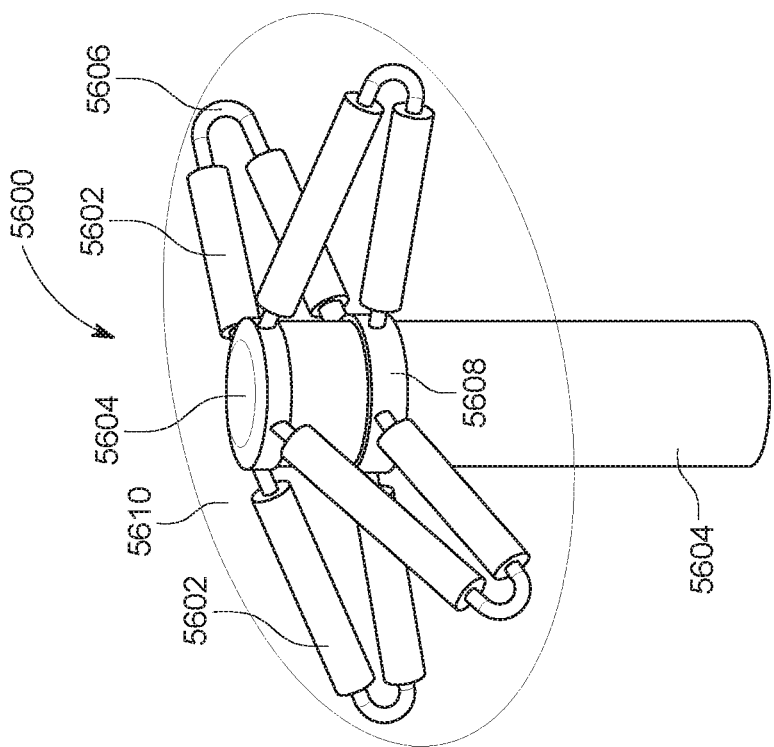
Figure 59:
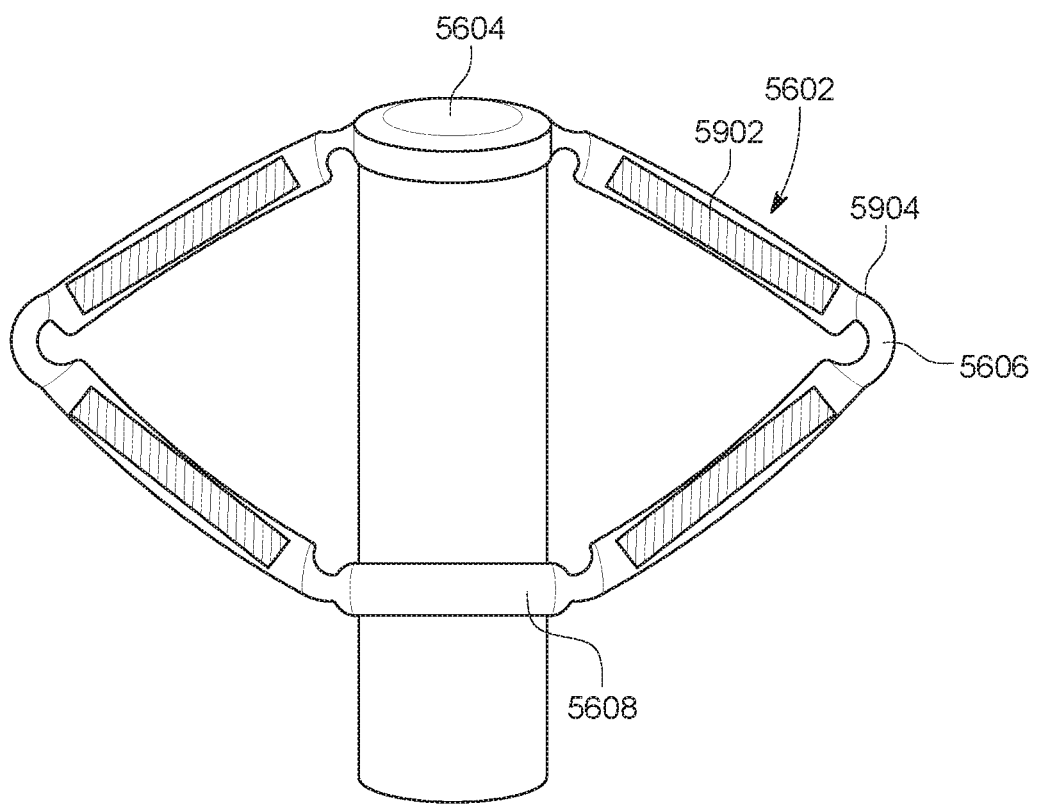
Figure 60:
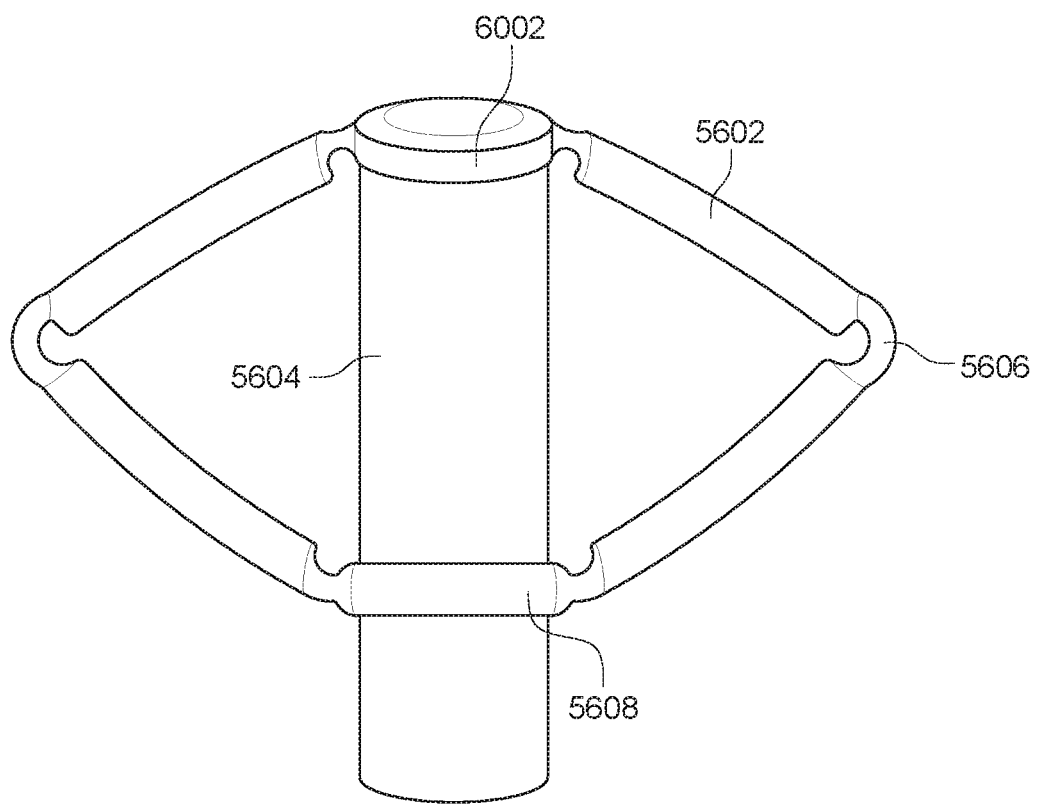

51C is a partially cut away perspective view of a locking mechanism pessary of FIG. 51B and shown in a collapsed state, according to the illustrative embodiment;

FIG. 51D is a partial perspective view of an upper portion of a pessary with a sliding ring, according to another embodiment;

FIG. 51E is a partial perspective view of the upper portion of the pessary of FIG. 51B shown in a collapsed state, according to the embodiment;

FIG. 52 is a top view of a pessary with a rotating ring lock, according to an illustrative embodiment;

FIG. 53 is a cross sectional view of the pessary with a rotating ring lock taken along cross section line 53-53 of FIG. 52, according to an illustrative embodiment;

FIG. 54 is a top view of a pessary with a rotating ring lock in a collapsed state, according to an illustrative embodiment;

FIG. 55 is a cross sectional view of the pessary of with a rotating ring lock in a collapsed state, taken along cross section line 55-55 of FIG. 54, according to an illustrative embodiment;

FIG. 56 is a perspective view of a pessary with a twisting deployment shown in a deployed state, according to an illustrative embodiment;

FIG. 57 is a perspective view of the pessary with a twisting deployment shown in a collapsed state, according to an illustrative embodiment;

FIG. 58 is a perspective view of the pessary with a twisting deployment of FIG. 56 showing a locking mechanism, according to an illustrative embodiment;

FIG. 59 is a partially cut away perspective view of the pessary with a twisting deployment of FIG. 56 showing the interior of the petals, according to an illustrative embodiment; and FIG. 60 is a perspective view of the pessary with a twisting deployment of FIG. 56 showing living hinges, according to an illustrative embodiment.

DETAILED DESCRIPTION

Figure 1:
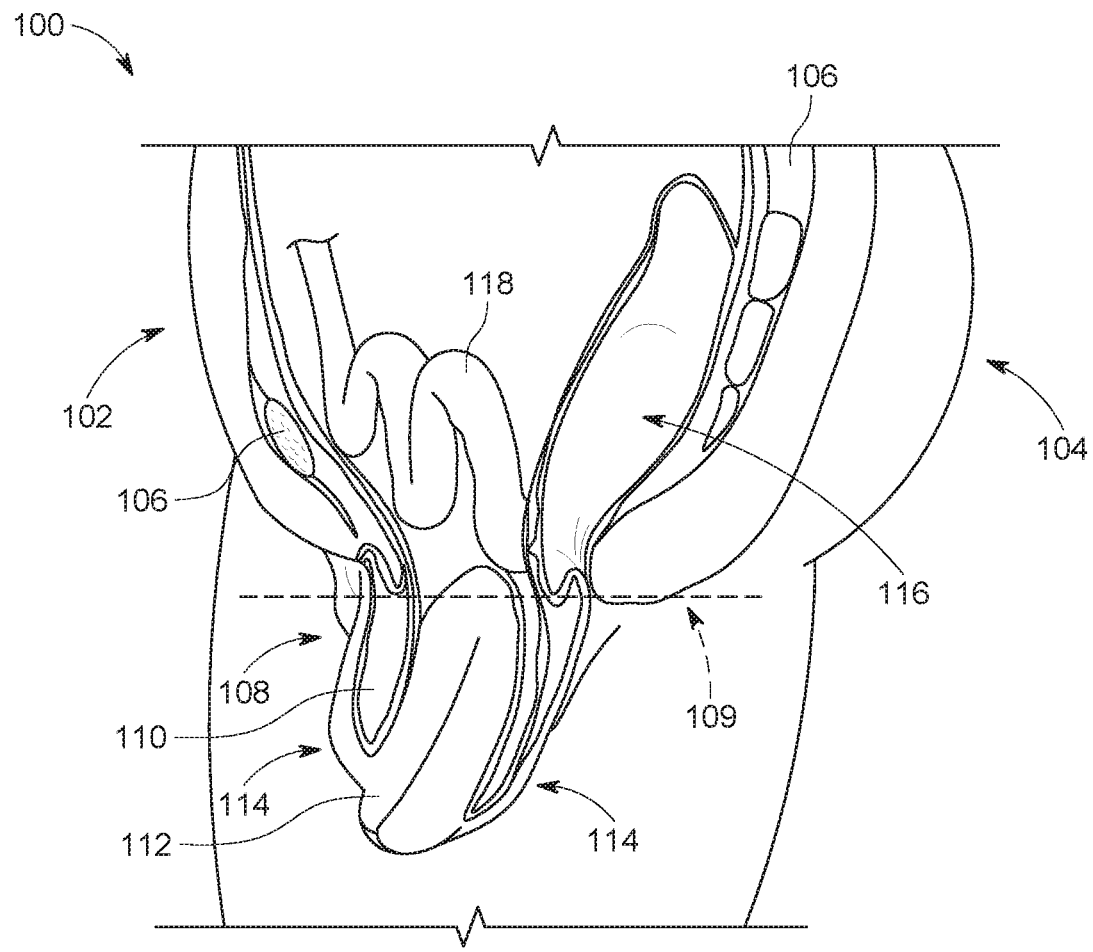
FIG. 1 is a cross sectional view of the pelvic organs in a prolapsed state, according to the prior art.
Figure 2:
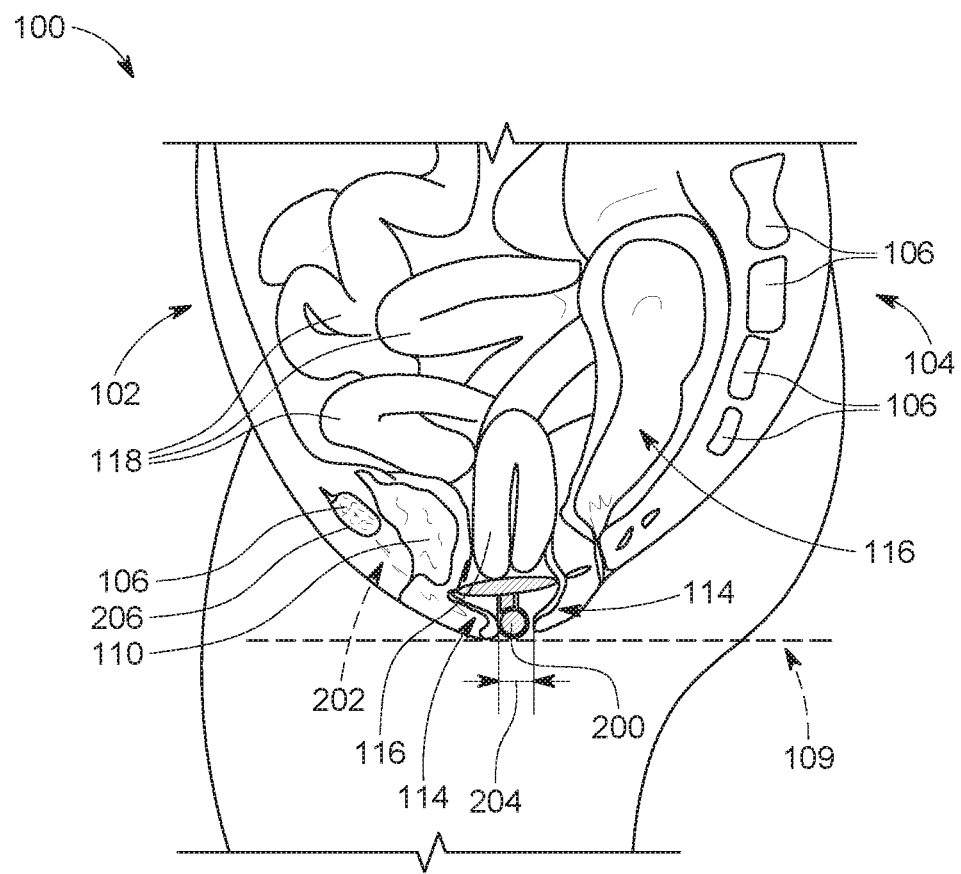
FIG. 2 is a view of an inserted pessary, according to the prior art.
Figure 3:
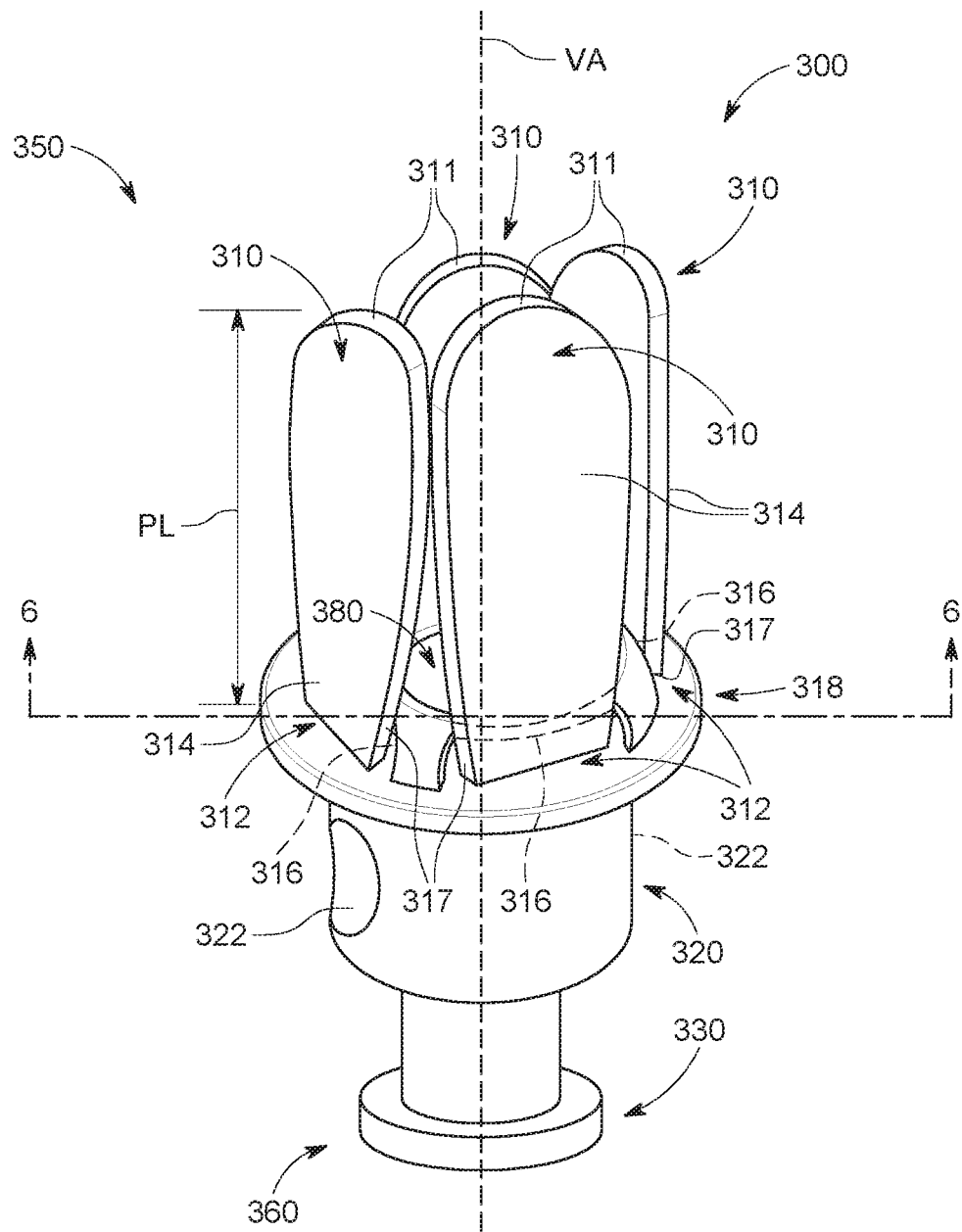
FIG. 3 is a perspective view of a pessary for pelvic organ prolapse in a collapsed state, according to an embodiment.

FIG. 3 is a perspective view of a pessary for pelvic organ prolapse in a collapsed state, according to a first embodiment. A vaginal pessary 300 can be used for treatment of pelvic organ prolapse, and can be retractable and/or collapsible. The pessary 300 can be easily insertable and removable when in a collapsed state. The pessary 300 can include a plurality of L-shaped petal members 310, a hollow stem 320 that can include a shelf 318 at or near the top of the hollow stem 320, a plunger 330 that can include a plunger cap 380 and can reside within the hollow stem 320, and at least one connection to join the petal member 310 to the top of the stem 320. In an embodiment, a pessary can be provided with four rigid or semi-rigid L-shaped petal members 310 with rounded edges 311. In various embodiments, a pessary can have more than or fewer than four petal members. The L-shaped petal members 310 can have a longer segment 314 that is the upper portion of the "L" shape, and a shorter segment 316 that is the lower portion of the "L" shape, so that the elongated segment 314 and the shorter segment 316 can have an angle between them. Each of the petal members 310 can be constructed with a rotation point 317 that can define a bend, or a point of transition, between the elongated segment 314 and the short segment 316. The petal members 310 can be attached to the stem 320 at a hinge. The long segment 314 can rotate from the approximately vertical orientation as shown in FIG. 3, to a position that can be approximately perpendicular to a vertical axis VA that describes a central line extending through and from the top end 350 through the bottom end 360. The material of the pessary can be a biocompatible FDA (U.S. Food and Drug Administration) approved silicone or plastic material. The exterior edges of the petal members can be rounded off, to avoid any sharp edges that might cause injury, infection or irritation to the user.

In the collapsed state shown in FIG. 3, the plunger 330 and plunger cap 380 can be in a lowered position with respect to the stem 320, and can be out of contact with the short segment 316. The short segment 316 can be oriented inwards towards the vertical axis VA, and the elongated segment 314 can be oriented upwards so as to be substantially aligned with the vertical axis VA. In the collapsed state the overall diameter of the pessary is at a minimum. Although the elongated segments 314 are referred to herein as being vertical, or parallel with the vertical axis VA, when they are in the collapsed state, it should be clear that the elongated segments 314 can hinge inward to a position beyond vertical, so that the elongated segments 314 are leaning inward towards the vertical axis, however, for the sake of clarity and readability, the collapsed state will be referred to herein as being vertical or parallel to the vertical axis.

The elongated segment 314 can have a length PL that can vary depending on the overall width of the pessary, which can be dependent upon the size of the vaginal canal introitus. In various embodiments, the length PL of a petal member can be in a range from approximately 0.75 to approximately 2.5 inches (±0.25 inches). The stem 320 can be a hollow cylinder with a shelf 318 at its uppermost end. Shelf 318 can be co-formed with the stem 320. The shelf 318 can provide a resting place for the petal members when deployed, as well as a stopping point for the rotation of the petal members. The stem can include indented gripping surfaces 322 that can improve gripping during insertion and removal. A plunger 330 can be provided at the bottom end 360. When pushed upwards, the plunger can cause deployment of the petal members 310. As used herein, the directional terms, such as, but not limited to, "up" and "down", "upward" and "downward", "rear", "rearward" and "forward", "top", "topmost" and "bottom", "inside" and "outer", "front" and "back", "inner" and "outer", "interior" and "exterior", "downward" and "upward", "horizontal" and "vertical" should be taken as relative conventions only, rather than absolute indications of orientation or direction with respect to an acting direction of the force of gravity.

Figure 4:
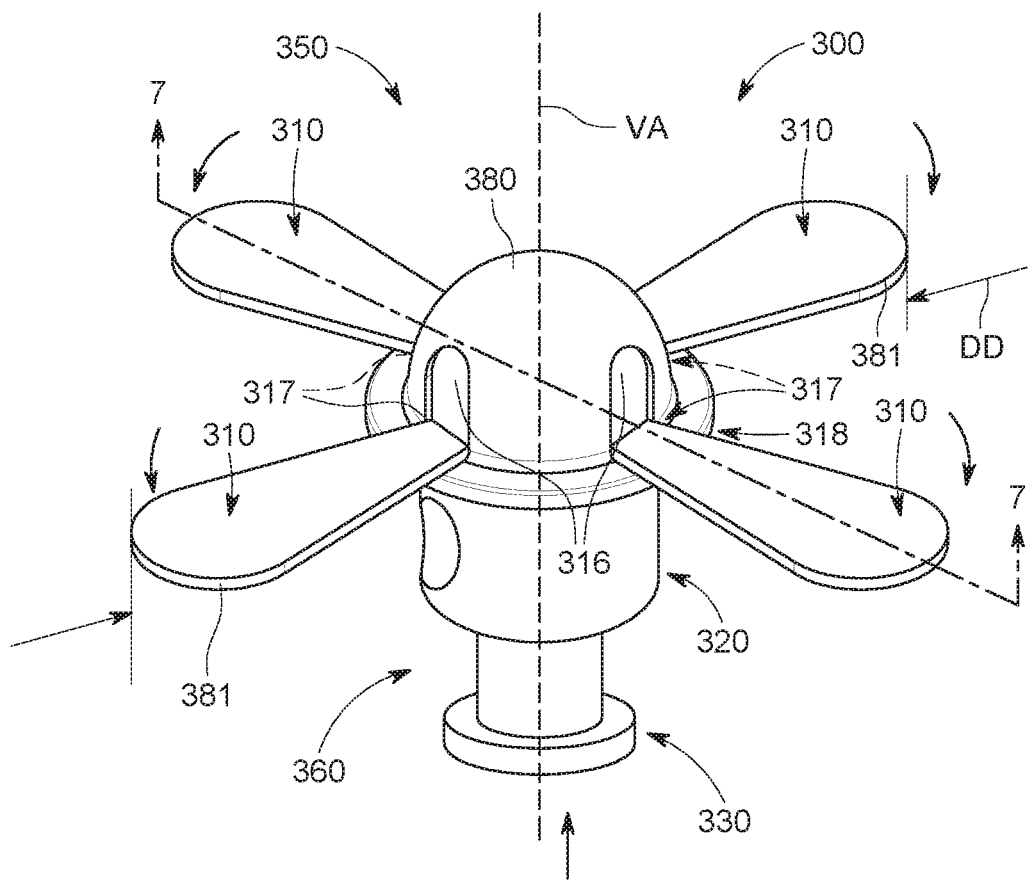
FIG. 4 is a view of the pessary in a deployed state, according to an embodiment.

FIG. 4 is a view of a pessary in a deployed state, according to an embodiment. Turning to FIGS. 3 and 4, a pessary 300 can be arranged in either a collapsed state or a deployed state. The collapsed state is suitable for the insertion and removal of the pessary, and can be defined as the configuration in which the plunger 330 is at its lowest position and the elongated segment of each of the L-shaped petal members can be parallel with the vertical axis VA and the shorter segment of each petal member can be oriented inwards. In the collapsed state, the shorter segments 316 can protrude into the center of the stem. When the pessary is in its collapsed state, the diameter of the pessary is at a minimum. When the pessary is in a deployed state, the plunger 330 can be at an uppermost position, the plunger cap 380 can be protruding from the stem, and the elongated segments 314 of each of the petal members 310 can be resting upon and supported by the shelf 318 such that each of the elongated segments 314 can be extended outwards from the vertical axis VA. The pessary 300 can be deployed to the deployed state after insertion into the vaginal canal. In the deployed state, the pessary can have a maximum deployed diameter DD at the widest location. The deployed diameter DD of the pessary in the deployed state can vary based upon the size of the vaginal canal introitus. In an embodiment, the diameter DD of a deployed pessary can be in a range from approximately 1.75 to approximately 5 inches (±0.25 inches). The overall diameter of the pessary in a deployed state is greater than the overall diameter of the pessary in a collapsed state.

A pessary can be inserted by introducing the top end 350 of the pessary 300 into the opening of the vaginal canal and pushing upwards along the vaginal canal (and inwards with respect to the vaginal canal) until the pessary is in a desired position. Once the pessary 300 is inserted into the vaginal canal to the desired position, the plunger 330 can be pushed upwards within the hollow stem 320 to its highest position. As the plunger 330 moves upwards, the plunger cap 380 can engage with and push upwards on the short segment 316 of each petal member 310, thereby causing a rotational motion of the petal members. As the petal members 310 rotate, the elongated segments 314 can move downwards and outwards. The members can rotate approximately 90 degrees or more such that the short segments are approximately vertical (aligned so as to be parallel to the vertical axis VA) and the elongated segments 314 can be approximately perpendicular to the vertical axis VA. In this state, the elongated segments 314 can make contact with and can be supported by the shelf 318. The plunger 330 can remain at its highest position in the stem when the pessary is in its deployed state, and can constrain the L-shaped petal members 310 from rotating and returning to the collapsed state. When the plunger 330 is pulled downwards, the petal members 310 are no longer restrained and are thus free to rotate to the collapsed state with the elongated segments 314 in the vertical position. The pessary can have the smallest diameter in the collapsed state.

Figure 5:
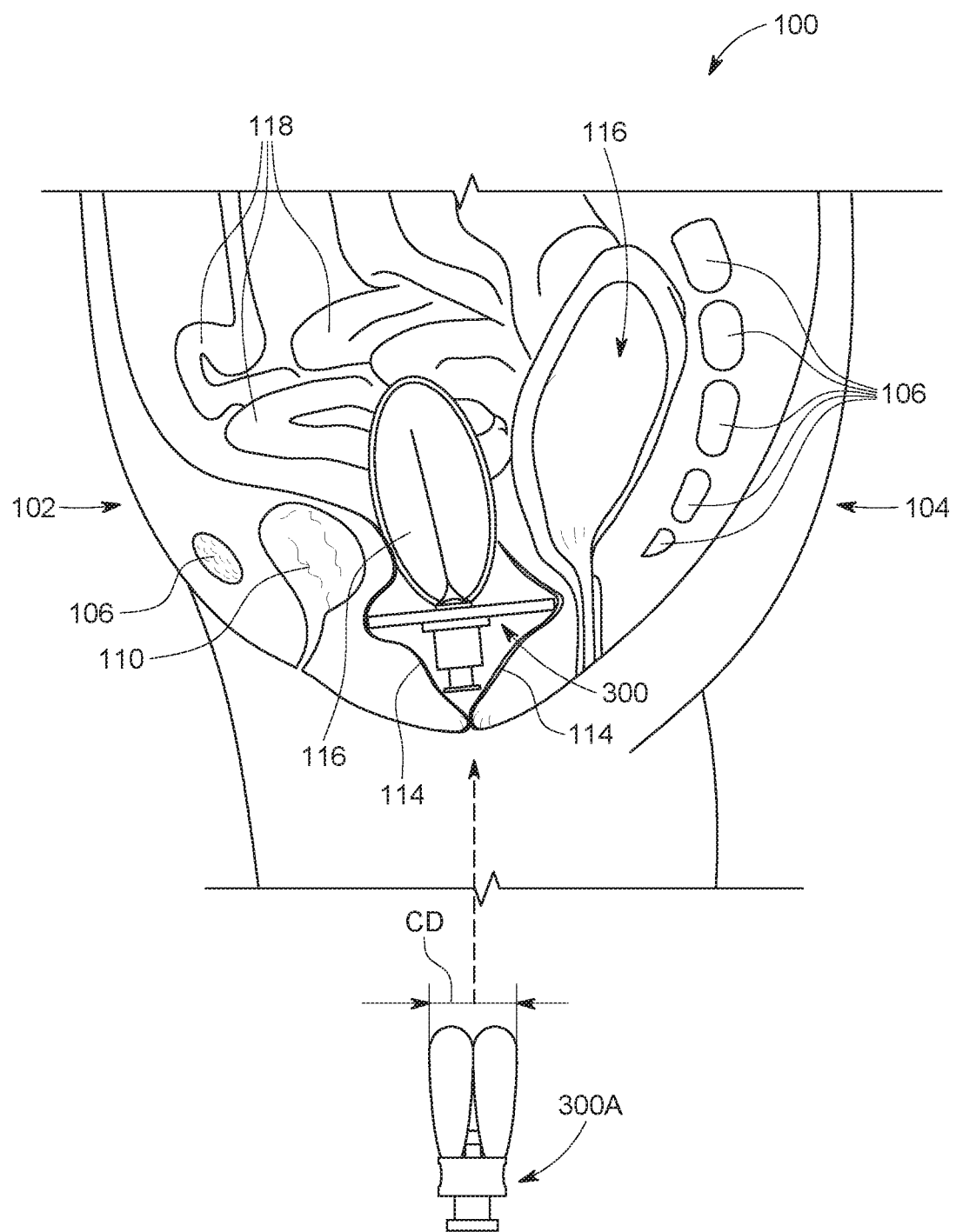
FIG. 5 is a view of the pessary in a deployed state, according to an embodiment.

FIG. 5 is a view of a pessary in a deployed state, according to an embodiment. The pessary 300 is shown in a deployed state within a vaginal canal 114 for support of a uterus 116 as a therapy for pelvic organ prolapse. Pessary 300A shows the pessary in a collapsed state prior to insertion and deployment. In its collapsed state, a pessary can have a collapsed diameter CD of approximately 1 inch (±0.5 inches). A soft silicone overmolding can provide for greater comfort during insertion, removal and deployment of the pessary.

Figure 6:
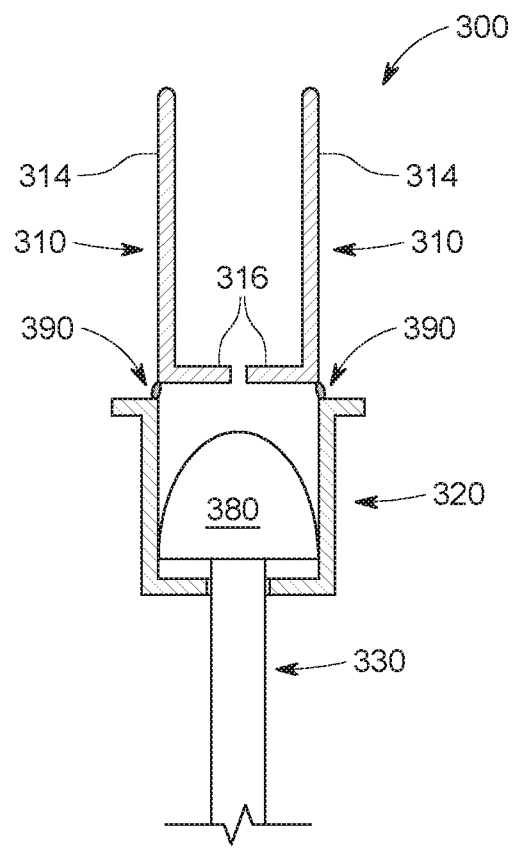
FIG. 6 is a cross-sectional view of the pessary along cross section line 6-6 of FIG. 3, according to an embodiment.

FIG. 6 is a cross-sectional view of the pessary along cross section line 6-6 of FIG. 3, according to an embodiment. FIG. 6 shows the petal members 310 in a collapsed state. A plurality of joints 390 can be situated along the top end of the stem 320 and can connect the stem 320 with the petal members 310. Each petal member 310 can be connected to the stem 320 by at least one joint 390. The joint 390 can be an interface between the stem and each of the petal members and can retain the petal members in connection with the stem during rotation and the states of collapsed and deployed. The joint 390 can be a hinge structure. It is contemplated that in other embodiments, the joint 390 can be a ring-like circumferential feature. In the collapsed state, the plunger cap 380 can be situated within the stem 320, below the short segments 316 of each of the petal members 310.

Figure 7:
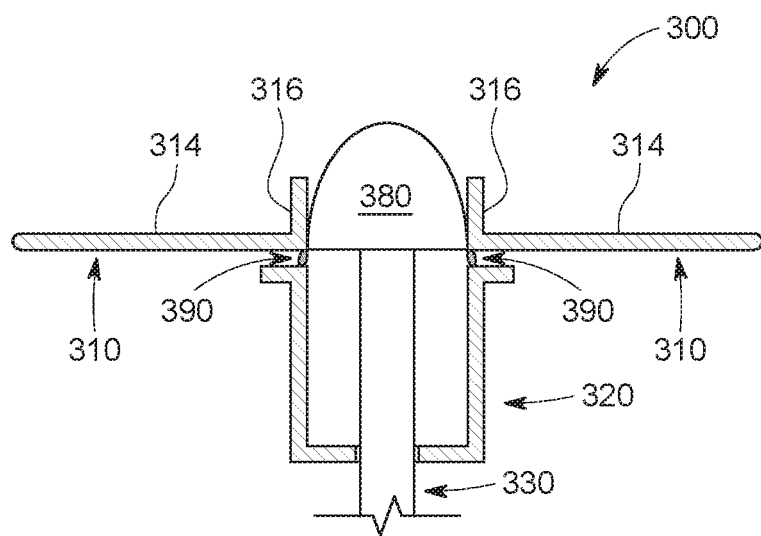
FIG. 7 is a cross-sectional view of the pessary along cross section line 7-7 of FIG. 4, according to an embodiment.

FIG. 7 is a cross-sectional view of the pessary along cross section line 7-7 of FIG. 4, according to an embodiment. FIG. 7 shows the petal members in the deployed state. In the deployed state, the plunger cap 380 can be situated at the top end of the stem 320, engaging the short segments 316 of each of the petal members 310. During movement from the collapsed state to the deployed state, the motion of the petal members can be initiated when the plunger cap 380 is pushed upwards, coming into contact with the short segments 316 and urging them to rotate outwards as the plunger cap rises in the stem. When a removal of the pessary is desired, the plunger is moved to its downward position in the stem, drawing the plunger cap 380 downwards and out of contact with the petal members 310, allowing the elongated segments to return to the vertical orientation as the stem is pulled downwards.

Figure 8:
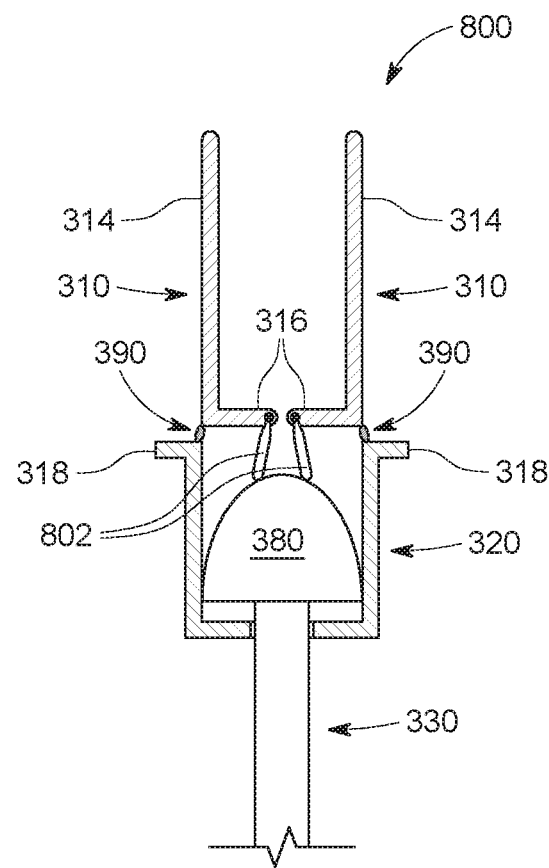
FIG. 8 is a view of a pessary with a connection between the plunger cap and the petal members shown in a collapsed state, according to an embodiment.

FIG. 8 is a view of a pessary in a collapsed state and with a connection between the plunger cap and the petal members, according to an embodiment. In an embodiment, a pessary 800 can have a connection 802 that can be connected at one end to the top surface of the plunger cap 380, and can be connected at the other end to each of the short segments 316 of the petal members 310. The pessary 800 is depicted in a collapsed state in FIG. 8. Connection 802 can be fixed at its ends so that it can serve as a hinge during the movements (upwards and downwards) of the plunger cap 380. When the pessary 800 is converted from a deployed state to a collapsed state by pulling down on the plunger, the connections 802 can pull the short segments 316 inward and downward, thereby rotating the elongated segments 314 upward and inward into the collapsed state.

Figure 9:
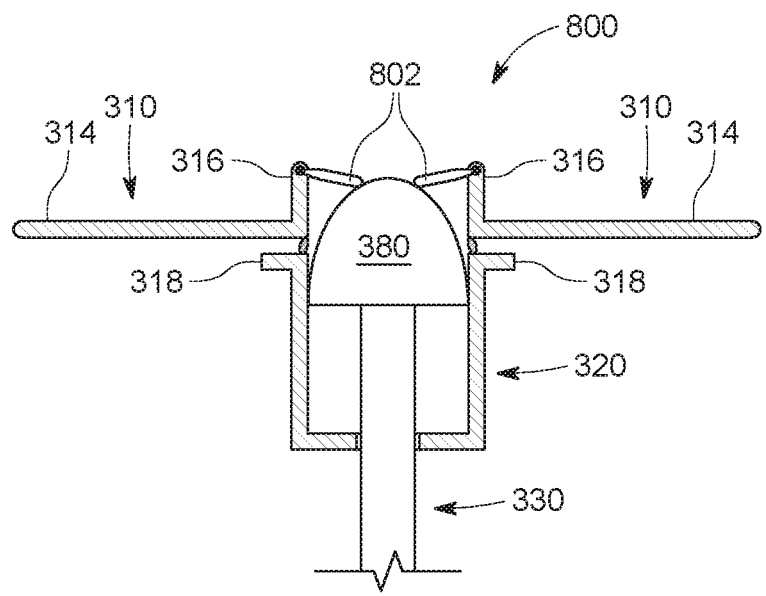
FIG. 9 is a view of the pessary of FIG. 8 with a connection between the plunger cap and the petal members and shown in a deployed state, according to an embodiment.

FIG. 9 is a view of the pessary in a deployed state and with a connection between the plunger cap and the petal members, according to an embodiment. When the pessary 800 is converted from a collapsed state to a deployed state by pushing the plunger up into the stem 320, the connections 802 can urge the short segments 316 upwards and outwards, thereby rotating the elongated segments outward and downward into the deployed state.

Figure 10:
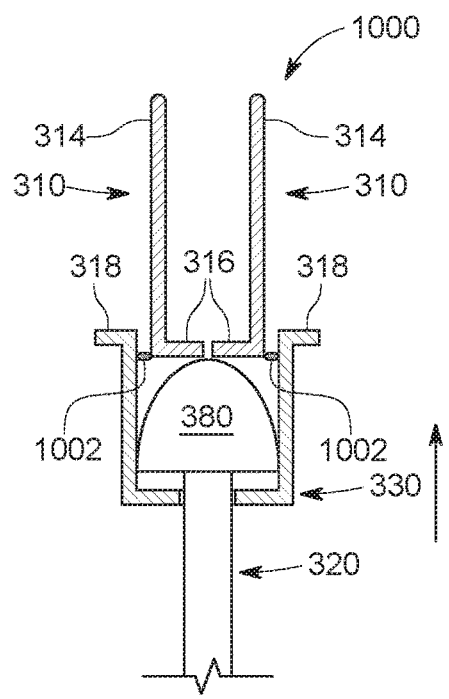
FIG. 10 is a view of a pessary with a sliding joint interface in a first collapsed state for insertion, according to an embodiment.

FIGS. 10-13 show a pessary with a sliding joint interface, according to an embodiment. A pessary 1000 can have a connection 1002 that can be a sliding joint interface between the petal members 310 and the stem 320. The connection 1002 can slide up and down within the stem 320, and can permit the petal members 310 to rotate at the connection 1002. FIG. 10 is a view of a pessary with a sliding joint interface in a first collapsed state, according to an embodiment. In the first collapsed state shown in FIG. 10 the pessary 1000 is in a pre-insertion state and is ready for insertion. The plunger cap 380 can be below the short segments 316 of the petal members 310. The plunger cap 380 can be out of contact with the petal members 310 in the first collapsed state. The sliding connections 1002 are in their lowest position in the stem. The sliding connections 1002 can reside in part in grooves (not shown) on the interior surface of the stem 320, and the sliding connections 1002 can move upwards and downwards within the grooves. In the pre-insertion state, the petal members can be at least partially contained within the stem 320. In this pre-insertion state, the stem 320 can retain the elongated members 314 in a collapsed state, so that they cannot rotate into a deployed state during the insertion process.

Figure 11:
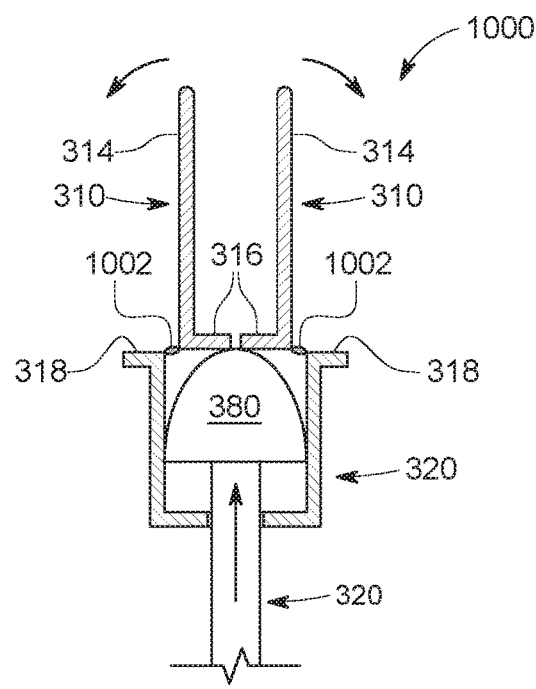
FIG. 11 is a view of the pessary of FIG. 10 with a sliding joint interface in an intermediary state, according to an embodiment.

FIG. 11 is a view of the pessary of FIG. 10 with a sliding joint interface in an intermediary state, according to an embodiment. In FIG. 11, the plunger 330 is shown in an intermediate state, and moving upwards into a deployed position. The plunger cap 380 can be in contact with the short segments 316 of the petal members 310. In the intermediate state, the plunger cap 380 can begin urging the petal members 310 upwards until they emerge above the shaft 320. As the petal members move upwards, the sliding connections 1002 also move upwards to the top of the shaft. When the sliding connections 1002 and the petal members 310 reach the end of their travel at the top of the shaft, the plunger cap 380 can push the short segments 316 upwards and outwards, so that the petal members 310 can begin to rotate at the sliding connections 1002. As the petal members 310 rotate, the elongated segments 314 can swing outwards and downwards towards the deployed position.

Figure 12:
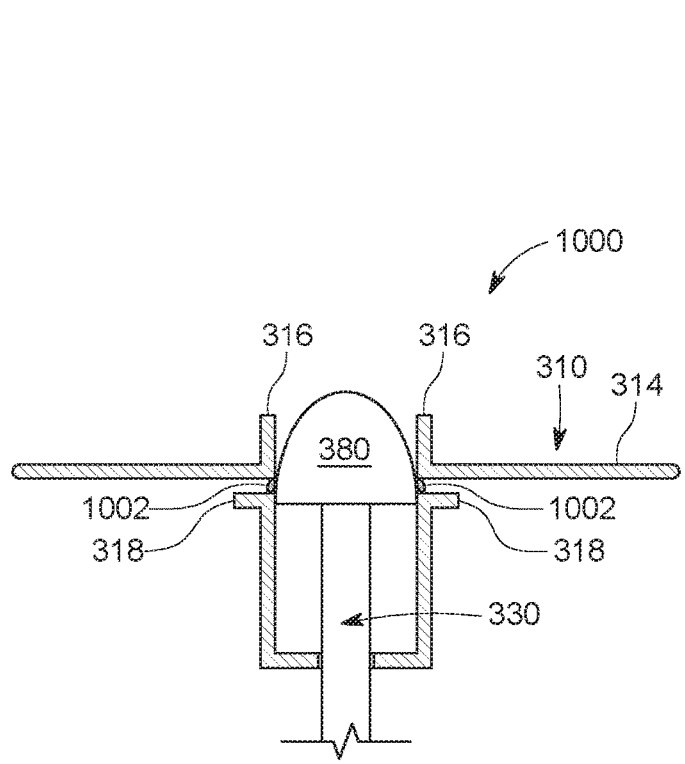
FIG. 12 is a view of the pessary of FIG. 10 with a sliding joint interface in a deployed state, according to an embodiment.

FIG. 12 is a view of the pessary of FIG. 10 with a sliding joint interface in a deployed state, according to an embodiment. The plunger cap 380 and the sliding connections 1002 are at their highest position in the stem. The elongated segments 314 are in the deployed position and are resting on and supported by the shelf 316.

Figure 13:
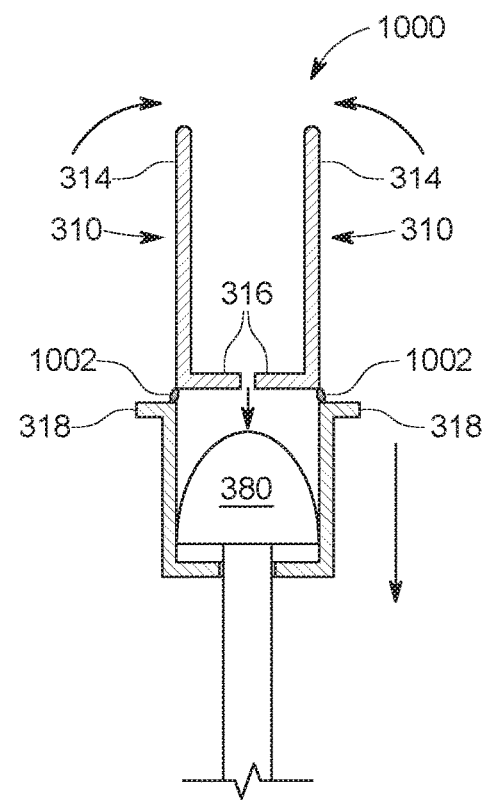
FIG. 13 is a view of the pessary of FIG. 10 with a sliding joint interface in a second collapsed state for removal, according to an embodiment.

FIG. 13 is a view of the pessary of FIG. 10 with a sliding joint interface in a second collapsed state for removal, according to an embodiment. The plunger cap 380 can be below the short segments 316 in the stem 320 and can be out of contact with the petal members 310. The plunger cap 380 can be at its lowest position in the stem 320. The sliding connections 1002 can remain in their highest position in the stem. As the pessary is removed in a downward movement through the vaginal canal, the walls of the vaginal canal can urge the petal members 310 to move upwards into the vertical orientation.

Figure 14:
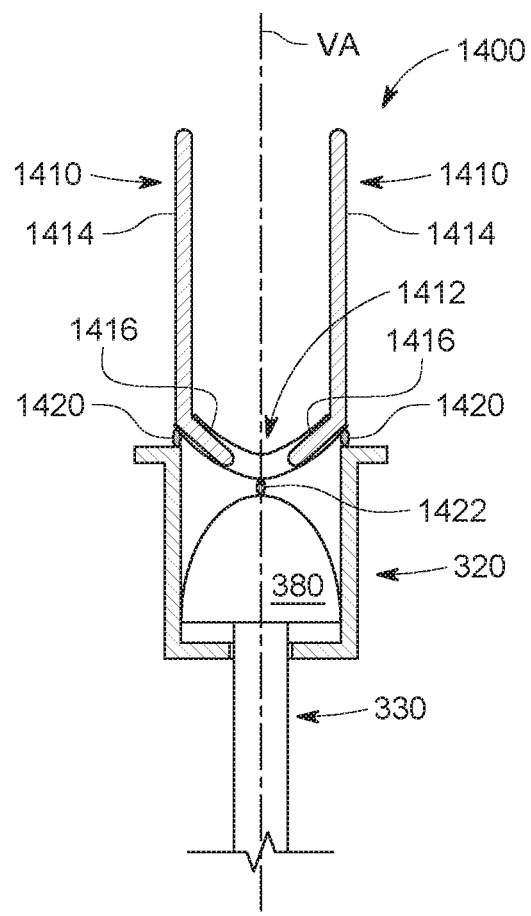
FIG. 14 is a view of a pessary with a connecting deformable membrane in a collapsed state, according to an embodiment.

FIG. 14 is a view of a pessary with a connecting deformable membrane in a collapsed state, according to an embodiment. A pessary 1400 can have a connecting deformable membrane 1412 that connects petal members 1410. The pessary 1400 can have connections 1420 that can connect the petal members 1410 to the shaft 320. The pessary 1400 can have a connection 1422 that connects the membrane 1412 to the plunger cap 380. The petal members 1410 can have an obtuse angle between the elongated segment 1414 and the short segment 1416. The short segments 1416 can be at least partially embedded within the deformable membrane 1412. In the collapsed state shown in FIG. 14, the deformable membrane can bulge inwards and downwards towards the interior of the shaft 320. In the collapsed state, the elongated segments 1414 can be in an approximately vertical orientation and can be aligned parallel to vertical axis VA. Connections 1420 join the petal members 1410 to the stem 320 and can function as a hinging joint. Connection 1422 joins the plunger cap 380 to the deformable membrane 1412.

Figure 15:
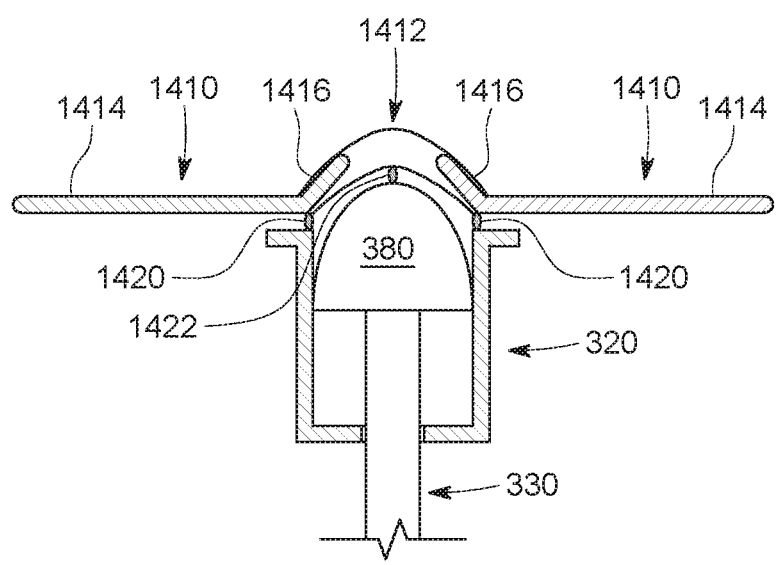
FIG. 15 is a view of the pessary of FIG. 14 with a connecting deformable membrane in a deployed state, according to an embodiment.

FIG. 15 is a view of the pessary of FIG. 14 with a connecting deformable membrane in a deployed state, according to an embodiment. In the deployed state, the plunger cap 380 can be at its highest position in the stem 320, pushing up on the deformable membrane 1412 and causing it to bulge upwards. When the deformable membrane 1412 and short segments 1416 are pushed upwards by the plunger cap 380, the elongated segments 1414 rotate outwards and downwards around connections 1420 until they are in the deployed position, which can be perpendicular to the vertical axis VA. As the plunger is pushed upwards, the plunger cap 380 can push upwards on the deformable membrane 1412 through connection 1422, causing the petal members 1410 to rotate into the deployed position shown in FIG. 15. When the plunger is pulled downwards, the deformable membrane 1412 can be pulled downwards by connection 1422, causing the petal members to rotate back into the collapsed position shown in FIG. 14.

Figure 16:
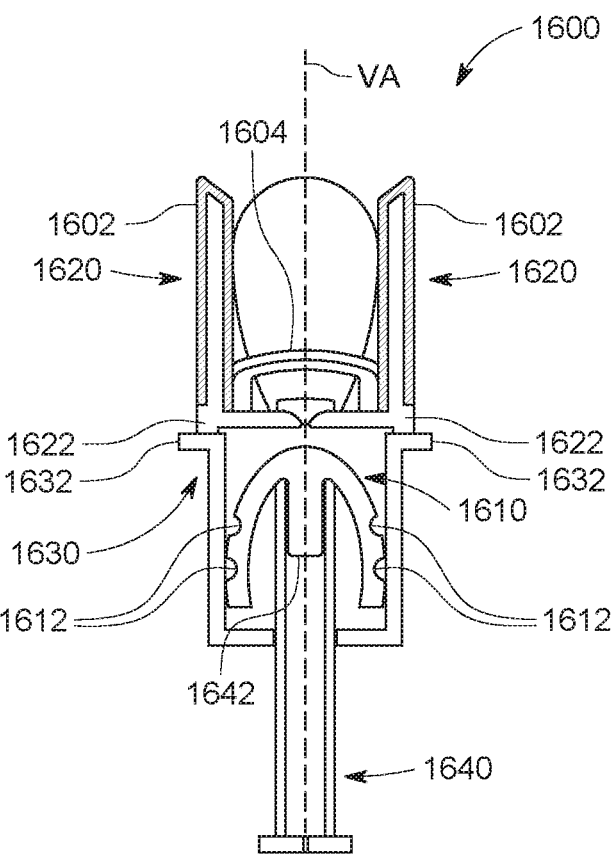
FIG. 16 is a view of a pessary with notches in the plunger cap and shown in a collapsed state, according to an embodiment.

FIG. 16 is a view of a pessary with notches in the plunger cap and shown in a collapsed state, according to an embodiment. A pessary 1600 can have silicone overmoldings 1602, a stem cap 1604, and a plunger cap 1610 that can include notches 1612. Stem cap 1604 can be a deformable membrane, or stem cap 1604 can be a rigid or semi-rigid cap. The pessary 1600 can have petal members 1620 with tabs 1622 near the hinge. Notches 1612 can engage the petal members 1620 at tabs 1622 to lock the petal members in a deployed state. Silicone overmoldings 1602 can cover the elongated segments of the petal members 1620, and can provide the petal members 1620 with a covering that can increase comfort for the user. In the collapsed state shown in FIG. 16, the plunger cap 1610 can be in a resting position that can be out of contact with the petal members 1620. The stem 1630 can include a shelf 1632 to support the petal members 1620 in the deployed state. In the collapsed state, the petal members 1620 can be in an approximately vertical orientation and aligned with the vertical axis VA.

When the pessary 1600 is manufactured, a hollow plunger 1640 can be inserted into the stem 1630. The plunger cap 1610 can have a plug 1642 within the bottom of the plunger cap 1610, and the plunger cap 1610 can be seated on the hollow plunger 1640 by insertion of the plug 1642 into the hollow plunger 1640. Petal members 1620 can then be added to the top of the stem 1630.

Figure 17:
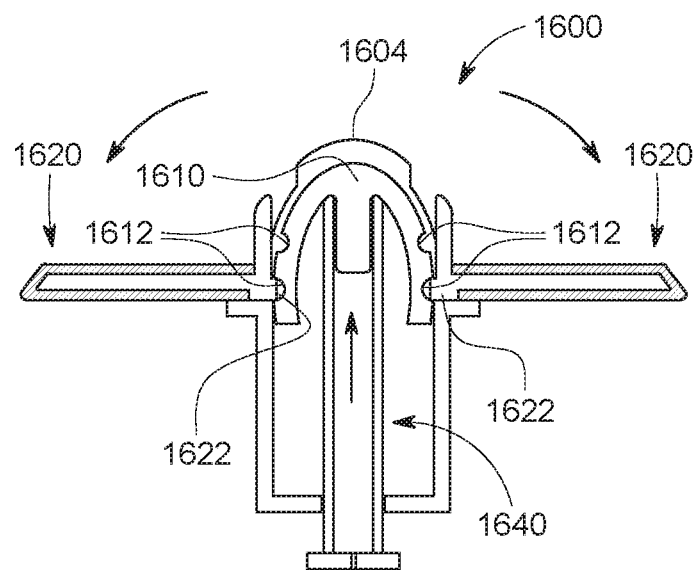
FIG. 17 is a view of the pessary of FIG. 16 with notches in the plunger cap and shown in a deployed state, according to an embodiment.

FIG. 17 is a view of the pessary of FIG. 16 with notches in the plunger cap and shown in a deployed state, according to an embodiment. Plunger cap 1610 can be pushed upwards in the stem, and the plunger cap 1610 can push upwards on the stem cap 1604 and/or petal members 1620, thereby rotating the petal members 1620 into a deployed position. In the deployed position, the petal members 1620 can be supported on the shelf 1632. In the deployed position, tabs 1622 can engage with grooves 1612, thereby locking the pessary 1600 in a deployed state. The tabs 1622 engaged in the grooves 1612 can hold the plunger cap 1610 in the upward position, thereby locking the petal members 1620 in the outstretched position.

Figure 18:
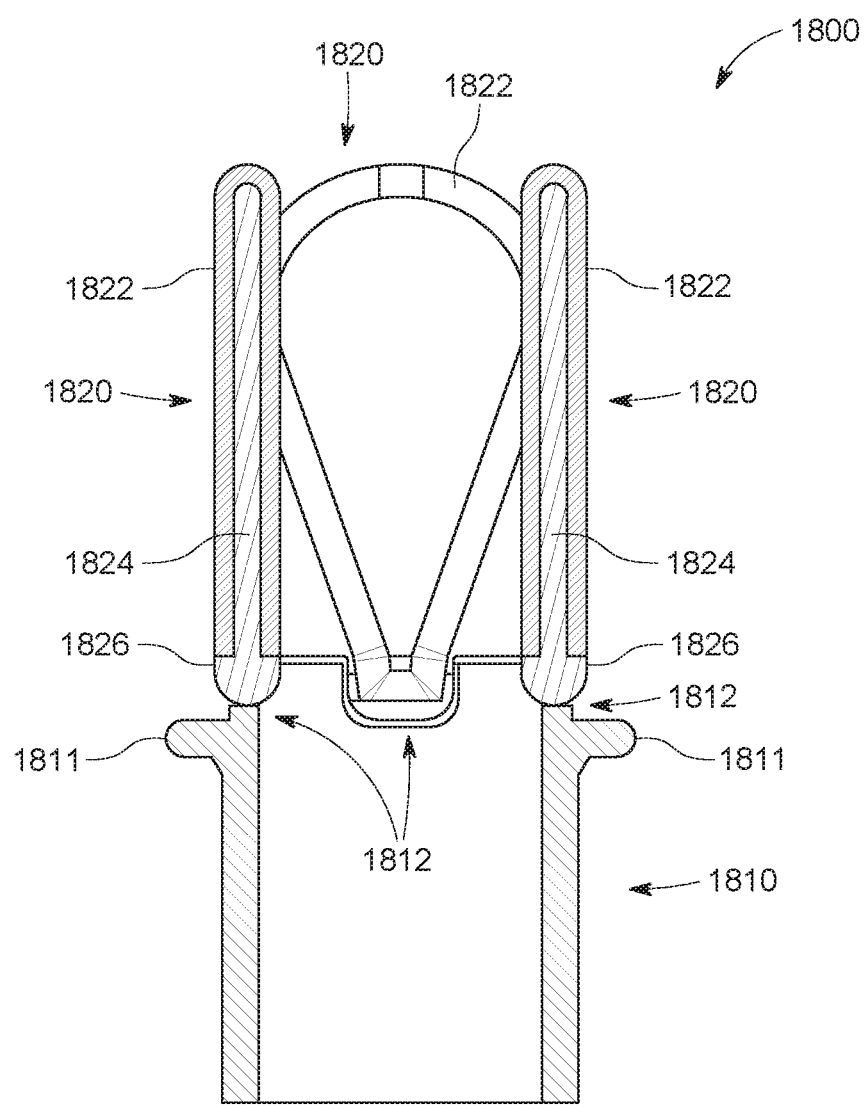
FIG. 18 is a view of a pessary that can be operated without a plunger, shown in a collapsed state according to an embodiment.

FIG. 18 is a view of a pessary that can be operated without a plunger, shown in a collapsed state according to an embodiment. Pessary 1800 can be free of a plunger. This plungerless pessary 1800 can be inserted, deployed and removed with the assistance of an applicator. FIG. 18 shows pessary 1800 in a collapsed state. The pessary 1800 can include a hollow stem 1810 and a plurality of petal members 1820. An applicator can hold the petal members in the collapsed state during the insertion process, and then the applicator can be removed after insertion, so that the petal members can rotate into the deployed state. The stem 1810 can be provided with a shelf 1811 at one end for supporting the petal members 1820. The stem 1810 can have cavities 1812 at or near the top edge of the stem. Cavities 1812 can allow petal members 1820 to rotate within the cavities 1812. The number of cavities 1812 can be the same as the number of petal members 1820. The petal members 1820 can have an outer layer of silicone overmolding 1822 over a rigid interior layer 1824. A hinged lower edge 1826 can be connected to the stem 1820 by a snap fitted nub in a socket.

FIG. 19A is a view of the pessary of FIG. 18 in a collapsed state with an applicator. The applicator 1900 can constrain the pessary 1800 in the collapsed state for insertion. In various embodiments, a pessary 1800 can have resilient hinge members 1902 that can be a silicone or other stretchable material. When the pessary 1800 is in the collapsed state within the applicator housing 1904, the petals 1820 have been rotated upwards and the silicone hinge 1902 can be stretched. After the pessary 1800 and applicator 1900 have been inserted into the vaginal canal, a user can push up on the plunger 1906 to eject the pessary 1800 out of the applicator housing 1904.

FIG. 19B is a view of the pessary 1800 that has been ejected from the applicator 1900. When the pessary 1800 is ejected out of the applicator 1900, the silicone hinges 1902 can return to the relaxed state by pulling the petals down so that they can rotate in the direction of arrow 1910 around their hinged lower edges 1826 until they rest upon the supportive shelf 1811. The silicone hinges 1902 can bias the petals 1820 into the deployed state so that the pessary 1800 remains in the deployed state within the vaginal canal. In various embodiments, the pessary 1800 can be free of silicone hinges 1902, the petals 1820 can be allowed to over-rotate further in the direction of arrow 1910, so that the petals point slightly downwards, and can therefore be maintained in the deployed position by the natural downward force exerted on the pessary 1800 by the descending organs.

Figure 20:
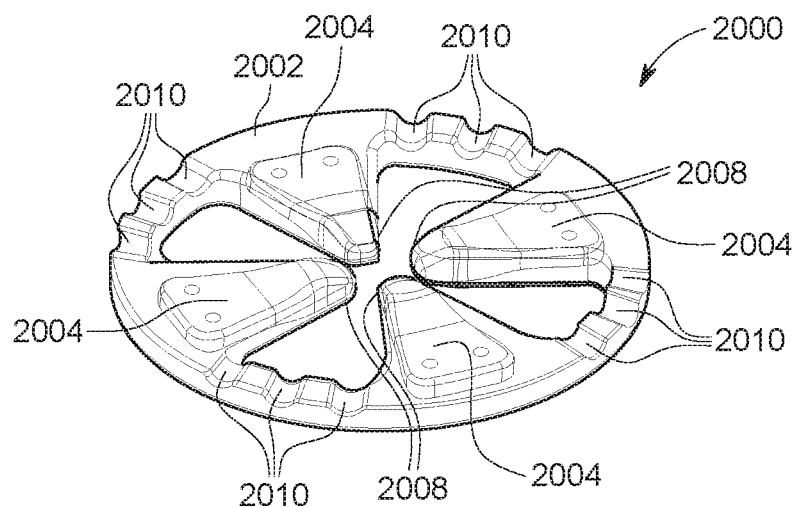
FIG. 20 is a perspective view of a unitary petal member for a pessary, according to an embodiment.

FIGS. 20-26 depict various alternative embodiments for the designs of the petal members as unitary petal members. These unitary petal members can be incorporated into various embodiments described herein, and can include features of the various embodiments. FIG. 20 is a view of a unitary petal member for a pessary, according to an embodiment. A unitary petal member 2000 for a pessary is shown in a fully extended and deployed state. The unitary petal member 2000 can be circular in shape and can includes a flexible and soft overmolding 2002 with multiple support members 2004 arranged within the unitary petal member 2000. Connection points 2008 can be hinged or otherwise connected to a stem (not shown). Cutout grooves 2010 can facilitate the collapse of the unitary petal member 2000 into a collapsed state with a smaller diameter for ease of insertion and removal.

Figure 21:
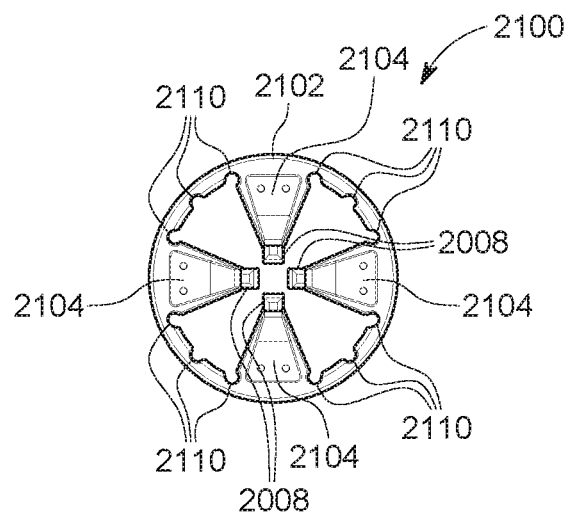
FIG. 21 is a top view of a unitary petal member for a pessary, according to an embodiment.

FIG. 21 is a top view of a unitary petal member for a pessary, according to an embodiment. The unitary petal member 2100 is shown in a fully extended and deployed state. The unitary petal member 2100 can be circular in shape and can include a flexible and soft overmolding 2102 with multiple support members 2104 arranged within the unitary petal member 2100. The unitary petal member 2100 is shown with four support members 2104, however, a unitary petal member can have more or fewer support members 2104. Connection points 2108 can be hinged or otherwise connected to a stem (not shown). Cutout grooves 2110 can be widely dispersed and can be located along the interior surface of the unitary petal member to facilitate the collapse of the unitary petal member into a collapsed state with a smaller diameter for ease of insertion and removal. The cutout grooves can be spaced widely between the support members 2104.

Figure 22:
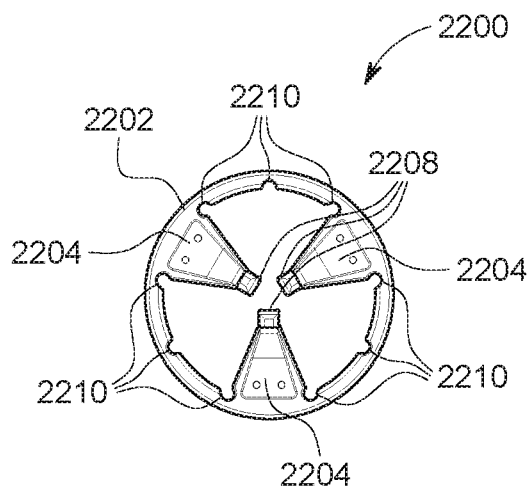
FIG. 22 is a top view of a unitary petal member for a pessary with three support members, according to an embodiment.

FIG. 22 is a top view of a unitary petal member for a pessary with three support members, according to an embodiment. A unitary petal member 2200 is shown in a fully extended and deployed state. The unitary petal member 2200 can be circular in shape and can include a flexible and soft overmolding 2202 with three support members 2204 arranged within the unitary petal member 2200. Connection points 2208 can be hinged or otherwise connected to a stem (not shown). Cutout grooves 2210 are widely dispersed and are located along the interior surface of the unitary petal member facilitate the collapse of the unitary petal member into a collapsed state with a smaller diameter for ease of insertion and removal.

Figure 23:
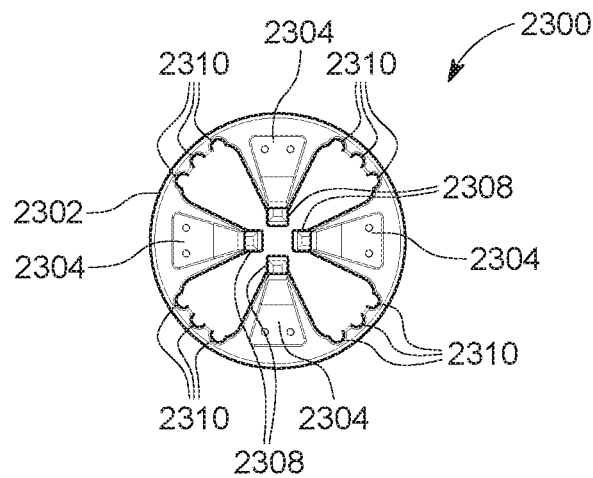
FIG. 23 is a view of a unitary petal member for a pessary with closely arranged cutout grooves, according to an embodiment.

FIG. 23 is a view of a unitary petal member for a pessary with closely arranged cutout grooves, according to an embodiment. The unitary petal member 2300 can be circular in shape and can include a flexible and soft overmolding 2302 with multiple support members 2304 arranged within the unitary petal member 2300. Connection points 2308 can be hinged or otherwise connected to a stem (not shown). Cutout grooves 2310 can be narrowly arranged with respect to each other and can located along the interior surface of the unitary petal member to facilitate the collapse of the unitary petal member into a collapsed state with a smaller diameter for ease of insertion and removal.

Figure 24:
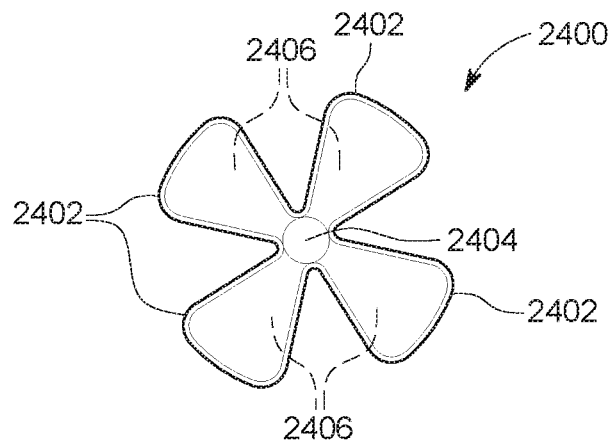
FIG. 24 is a view of a unitary petal member for a pessary with petal lobes, according to an embodiment.

FIG. 24 is a view of a unitary petal member for a pessary with petal lobes, according to an embodiment. The unitary petal member 2400 can have a plurality of petal lobes 2402. In an embodiment, the unitary petal member can be provided with four petal lobes 2402, however, it is expressly contemplated that the unitary petal member can be provided with more than four petal lobes, or less than four petal lobes in various embodiments. The petal lobes 2402 can be joined at a central hub 2404. The petal lobes 2402 can include internal supports 2406. The central hub and/or petal lobes can be flexible to provide for transition from collapsed state to deployed state and a narrower diameter while in the collapsed state.

Figure 25:
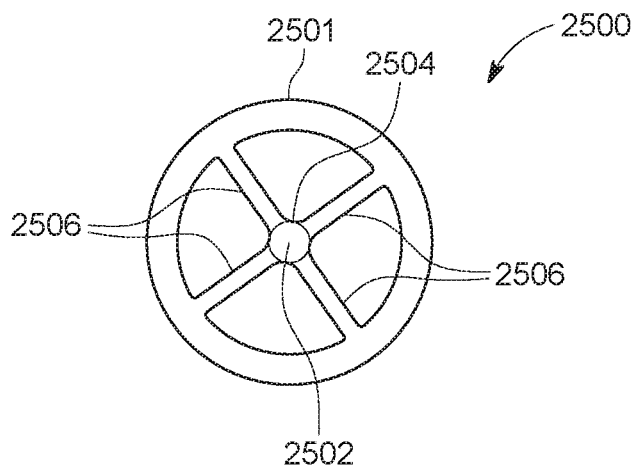
FIG. 25 is a view of a unitary petal member for a pessary with a circular profile, according to an embodiment.

FIG. 25 is a view of a unitary petal member for a pessary with a circular profile, according to an embodiment. A unitary petal member 2500 can have a circular outer rim 2501 that can be a ring shape. A central hub 2502 can be connected to the outer rim 2501 by spokes 2506. While the illustrative unitary petal member includes four spokes 2506, it is contemplated that it can be provided with more than four or less than four spokes. The central hub and/or petal lobes can be flexible to provide for transition from collapsed state to deployed state and a narrower diameter while in the collapsed state.

Figure 26:
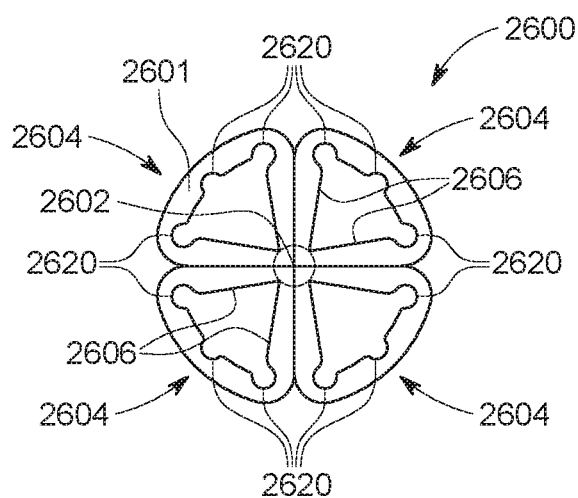
FIG. 26 is a view of a unitary petal member for a pessary with a lobed outer rim, according to an embodiment.

FIG. 26 is a view of a unitary petal member for a pessary with a lobed outer rim, according to an embodiment. A unitary petal member 2600 can have an outer rim 2601, and outer rim 2601 can have multiple lobes 2604. Outer rim 2601 is shown with four lobes 2604, however, an outer rim 2601 can have more or fewer lobes than four. A central hub 2602 can be connected to the outer rim 2601 by spokes 2606. While the illustrative unitary petal member includes four spokes 2606, it is contemplated that in other embodiments, the petal member can be provided with more than four or less than four spokes. The outer rim 2601 can include widely dispersed grooves 2620 to facilitate collapse. The central hub and/or petal lobes can be flexible to provide for transition from collapsed state to deployed state and a narrower diameter while in the collapsed state.

Figure 27:
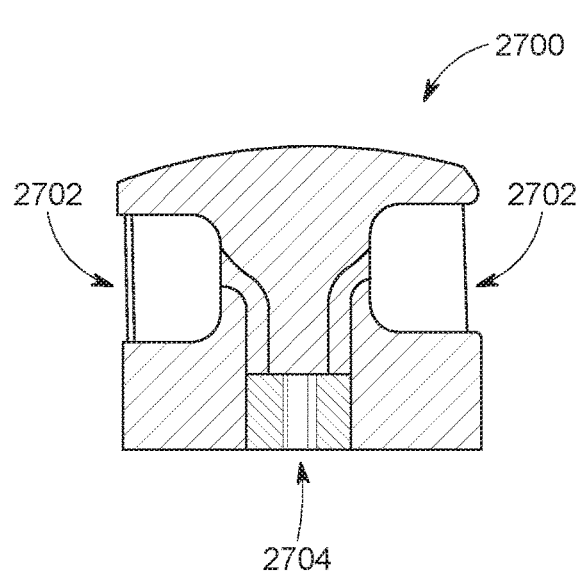
FIG. 27 is a view of a stem with rectangular cavities for petal members, according to an embodiment.

FIGS. 27-30 depict various cavity designs for the connection of the petal members to the top of the stem. FIG. 27 is a view of a stem with rectangular cavities for petal members, according to an embodiment. The top of a stem 2700 can be provided with multiple rectangular-shaped cavities 2702 that can function as seats for holding petal members. The stem 2700 can have passages 2704 that connect to the cavities 2702. Petal members (not shown) can have a cord that extends from the base of the petal through the passage 2704. When the cord is pulled, the base of the petal member can be pulled into the cavity so that when the petal member is engaged within the cavity, the petal member can be held in a deployed position with the petal member extending outwards from the cavity. In various embodiments, the cord can be a string, a wire, etc.

Figure 28:
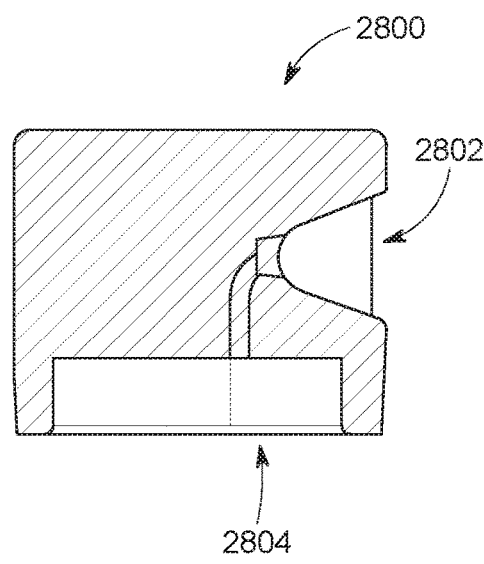
FIG. 28 is a view of a stem with trapezoidal cavities for petal members, according to an embodiment.

FIG. 28 is a view of a stem with trapezoidal cavities for petal members, according to an embodiment. The top of a stem 2800 can be provided with multiple trapezoidal-shaped cavities 2802 that can function as seats for holding petal members. The stem 2800 can have passages 2804 that connect to the cavities 2802. Petal members (not shown) can have a cord that extends from the base of the petal through the passage 2804. When the cord is pulled, the base of the petal member can be pulled into the cavity so that while the petal member is engaged within the cavity, the petal member can be held in a deployed position with the petal member extending outwards from the cavity. Turning back to FIG. 27, the rectangular cavities can hold the petal members in a more fixed position compared to the trapezoidal cavities of FIG. 28. The trapezoidal cavities 2802 can allow increased movement of the petal members up and down compared to the rectangular cavities of FIG. 27.

Figure 29:
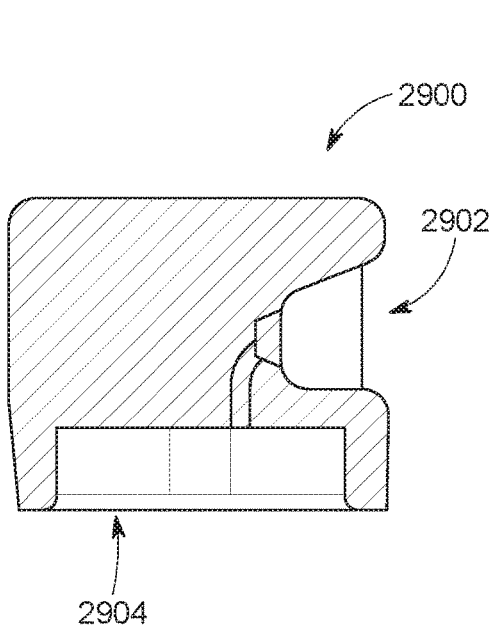
FIG. 29 is a view of a stem with an alternate cavity shape, according to a an embodiment.

FIG. 29 is a view of a stem with an alternate cavity shape, according to an embodiment. The top of a stem 2900 can have multiple cavities 2902 that can function as seats for holding petal members. Cavities 2902 can have a floor that can support the petal members (not shown) in a substantially horizontal position in the deployed state. The cavities 2902 can have a sloped ceiling that can allow the petal members to be angled upwards during removal of the pessary. The stem 2900 can have passages 2904 that can connect to the cavities 2902. Petal members (not shown) can have a cord that extends from the base of the petal through the passage 2904.

Figure 30:
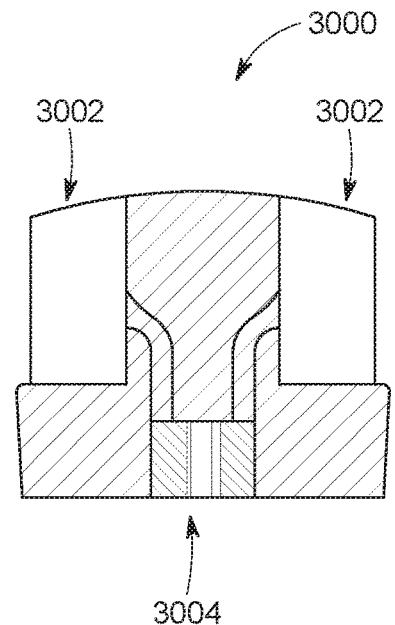
FIG. 30 is a view of a stem with a cavities having no ceiling, according to an embodiment.

FIG. 30 is a view of a stem with a cavities having no ceiling, according to an embodiment. The top of stem 3000 can have multiple cavities 3002. Cavities 3002 can have a floor that can support the petal members (not shown) in a substantially horizontal position in the deployed state. The cavities 3002 can be free of ceilings, so that the petal members can rotate upwards into a substantially vertical position in the collapsed state. The stem 3000 can have passages 3004 that can connect to the cavities 3002. Petal members can have a cord that extends from the base of the petal through the passage 3004. When the cord is pulled, the petal member can be pulled into the cavity 3002 so that the petal member can be held in a deployed position extending outward from the stem 3000. When the cord is relaxed, the petal members can rotate upwards into a collapsed state to facilitate insertion or removal of the pessary.

Figure 31:
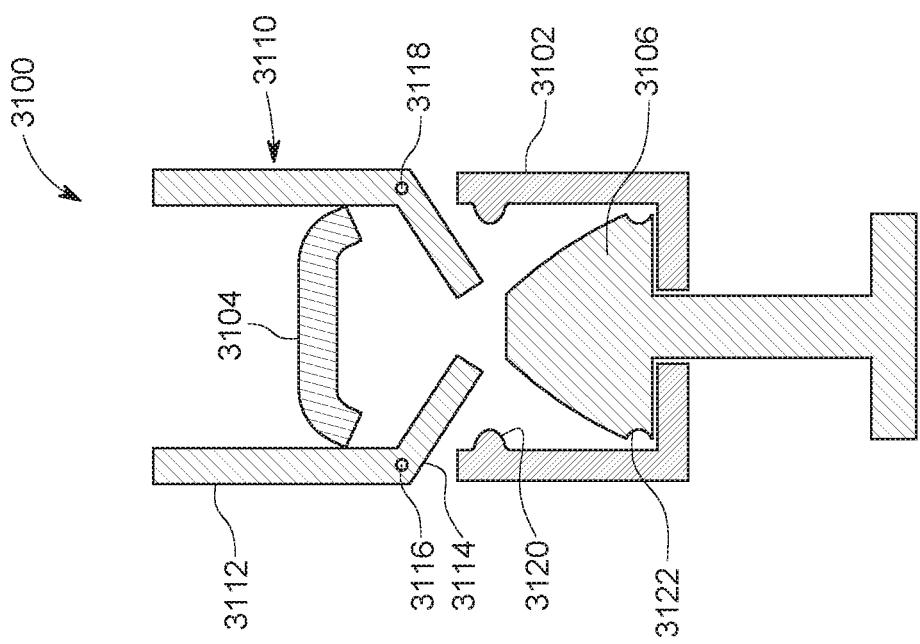
FIG. 31 is a partial view of a pessary with a rigid stem cap in a collapsed state, according to an embodiment.

FIG. 31 is a partial cutaway view showing the inner workings of a pessary with a rigid stem cap for holding petals in place in a deployed state, according to an embodiment. A pessary 3100 with a rigid stem cap can have a stem 3102 with a rigid stem cap 3104, a plunger cap 3106, and petal members 3110. Petal members 3110 can have an elongated segment 3112, a short segment 3114, a bend 3116 between the elongated segment 3112 and the short segment 3114, and a hinge 3118 at the bend 3116. The bend 3116 can have an obtuse angle, so that the short segments 3114 and the elongated segments 3112 can be fixed at an angle greater than 90 degrees relative to each other. The petal members 3110 can be attached to the stem 3102 at the hinge 3118. FIG. 31 depicts the pessary with a rigid stem cap 3104 in a collapsed state. In the collapsed state, the plunger cap 3106 can be in a down position, as shown in FIG. 31, thereby allowing the short segments 3114 to be in a downward position within the stem 3102. In this collapsed state with the short segments in a downward position within the stem, the elongated segments 3112 can rest against the rigid stem cap 3104, and the pessary can have a smaller diameter than in the deployed state. In various embodiments, an inner wall of the stem 3102 can have an interengaging feature such as bumps or a ridge 3120, and a stem cap 3104 can have a corresponding interengaging feature such as a divot or groove 3122, so that the interengaging features can hold the stem cap up in the deployed state.

Figure 32:
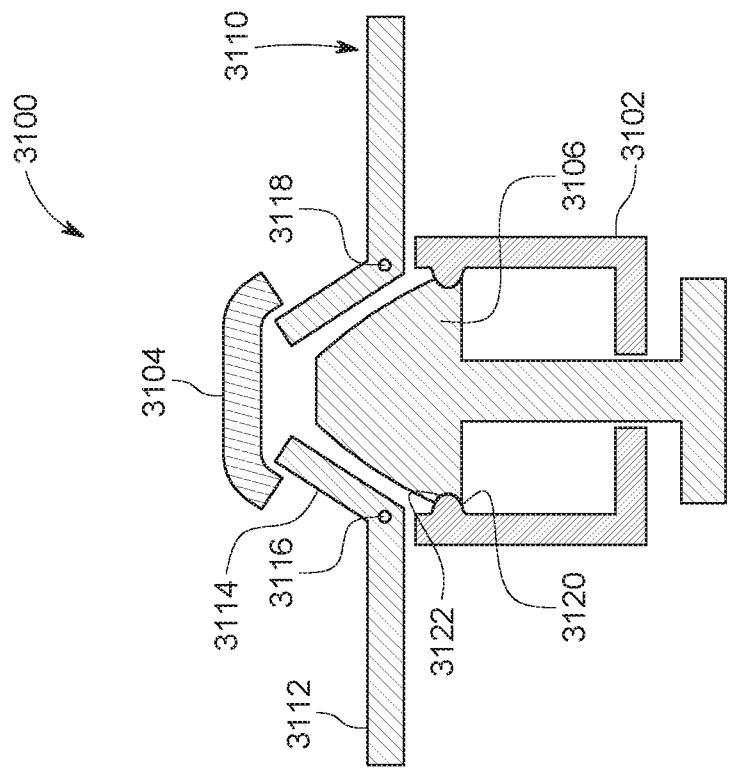
FIG. 32 is a partial view of the pessary with a rigid stem cap of FIG. 31, shown in a deployed state, according to an embodiment.

FIG. 32 is a partial cutaway view showing the inner workings of the pessary with a rigid stem cap of FIG. 31, shown in a deployed state, according to an embodiment. When the plunger cap 3106 is pushed up into the stem 3102, the plunger cap 3106 can push the short segments 3114 upwards, which can cause the petal members 3110 to rotate on the hinge 3118 until the elongated segments 3112 are in a deployed position. The ridge 3120 can be engaged with the groove 3122 to hold the pessary in the deployed position. In the embodiment shown in FIG. 32, the stem 3102 does not have (is free of) a shelf. In this embodiment without a shelf, the rigid stem cap 3104 can hold the petal members 3110 in the deployed position with the elongated segments 3112 extending outwards. When the petal members 3110 are rotated into the deployed position, the rigid stem cap 3104 can prevent the petal members 3110 from rotating beyond the deployed position. The short segments 3114 can be held in place between the plunger cap 3106 and the rigid stem cap 3104, so that the elongated segments 3112 can be maintained in the deployed position. When the plunger is pulled down, the short segments 3114 can rotate down into the stem 3102 and the elongated segments can rotate upwards back into the collapsed state shown in FIG. 31.

Figure 33:
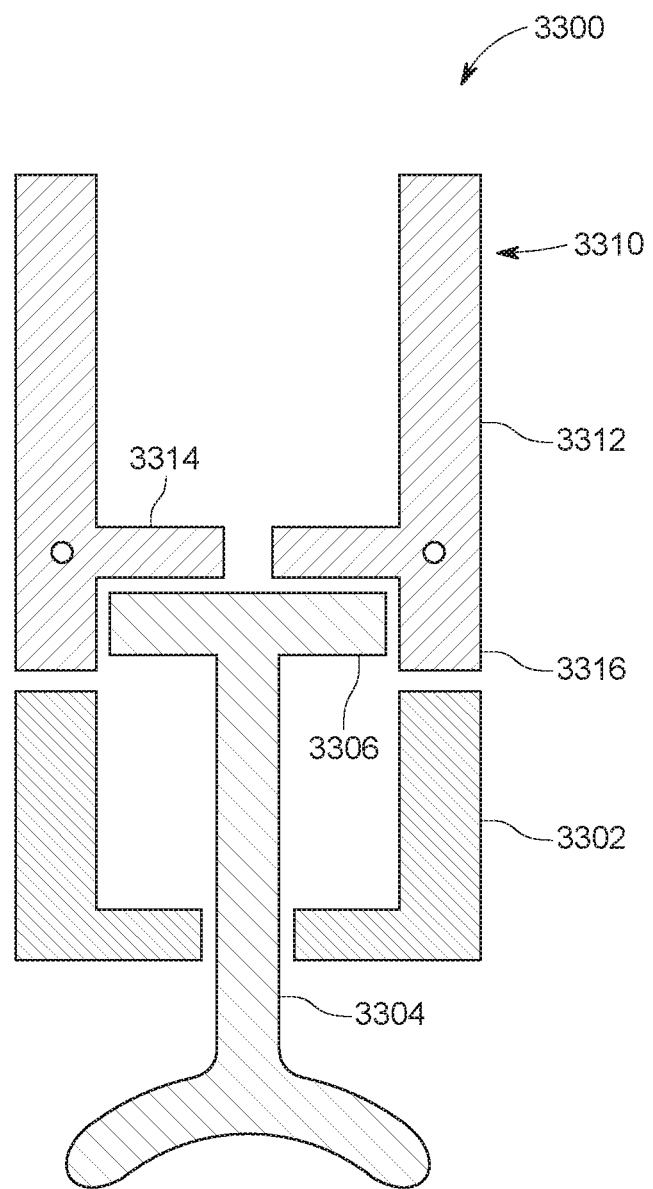
FIG. 33 is a partial view of a pessary with petals that can be held in place by a plunger, shown in a collapsed state, according to an embodiment.

FIG. 33 is a partial cutaway view showing the inner workings of a pessary with petals that can be held in place by a plunger, shown in a collapsed state. A pessary 3300 can have a stem 3302, a plunger 3304 with a plunger cap 3306, and petal members 3310. Petal members 3310 can have an elongated segment 3312, an intermediate segment 3314, and a short segment 3316. The petals 3310 can be maintained in the collapsed state by the plunger 3304. In the collapsed state with the plunger in the down position, the short segment 3316 can rest against the side of the plunger cap 3306, so that the plunger cap 3306 can prevent the short segment 3316 from rotating inwards. By preventing the short segments 3316 from rotating inwards, the plunger cap 3306 also prevents the elongated segments 3312 from rotating outwards into the deployed position. When the plunger 3304 is pushed up into the stem 3302, the plunger cap 3306 can push upwards on the intermediate segments 3314, causing the intermediate segments 3314 to rotate up and out, and thereby causing the elongated segments 3312 to rotate out and down into the deployed position.

Figure 34:
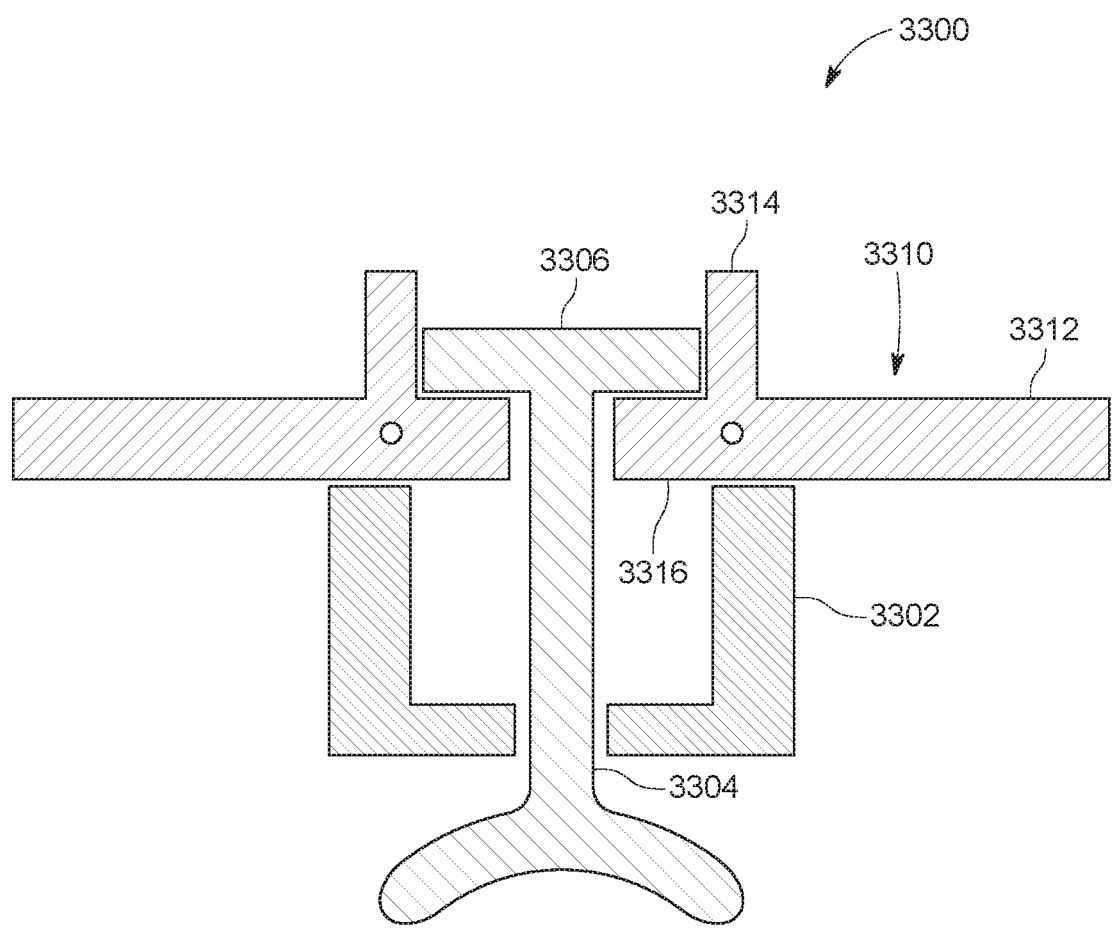
FIG. 34 is a partial view of the pessary of FIG. 33 with the petals in a deployed state, according to an embodiment.

FIG. 34 is a partial cutaway view showing the inner workings of the pessary of FIG. 33 with the petals in a deployed state, according to an embodiment. The pessary 3300 can be free of a supporting shelf for the petal members 3310, and the petal members 3310 can be held in a deployed position by the plunger cap 3306. In the deployed position, the short segments 3316 can contact the bottom of the plunger cap 3306. The bottom of the plunger cap 3306 can prevent the short segments 3316 from rotating upwards. Because the plunger cap 3306 prevents the short segments 3316 from rotating upwards, the petal members 3310 cannot over-rotate out of the deployed position. There is no need for a shelf on the stem, because the plunger cap 3306 can maintain the petal members 3310 in the deployed position, with the elongated segments 3312 extending outwards. The plunger cap 3306 can also prevent the intermediate segments 3314 from rotating inwards. In the deployed position, the intermediate segments 3314 can rest against the side of the plunger cap 3306, so that the petal members 3310 cannot rotate into the collapsed position. The plunger cap 3306 can prevent the petal members 3310 from rotating into the collapsed position by preventing the intermediate segments 3314 from rotating inward and downward, and the plunger cap 3306 can prevent the petal members from over-rotating out of the deployed position with the elongated segments extending outward by preventing the short segments 3316 from rotating upwards. The pessary 3300 can be locked into the deployed position with the petal members 3310 supported by the plunger cap 3306.

Pulling down on the plunger 3304 can cause the pessary 3300 to transition into the collapsed state. When the plunger 3304 is pulled down, the bottom of the plunger cap 3306 can push down on the short segments 3316, thereby causing the short segments 3316 to rotate downward and outward. When the short segments 3316 rotate downward, the elongated segments rotate upwards into the collapsed position.

Figure 35:
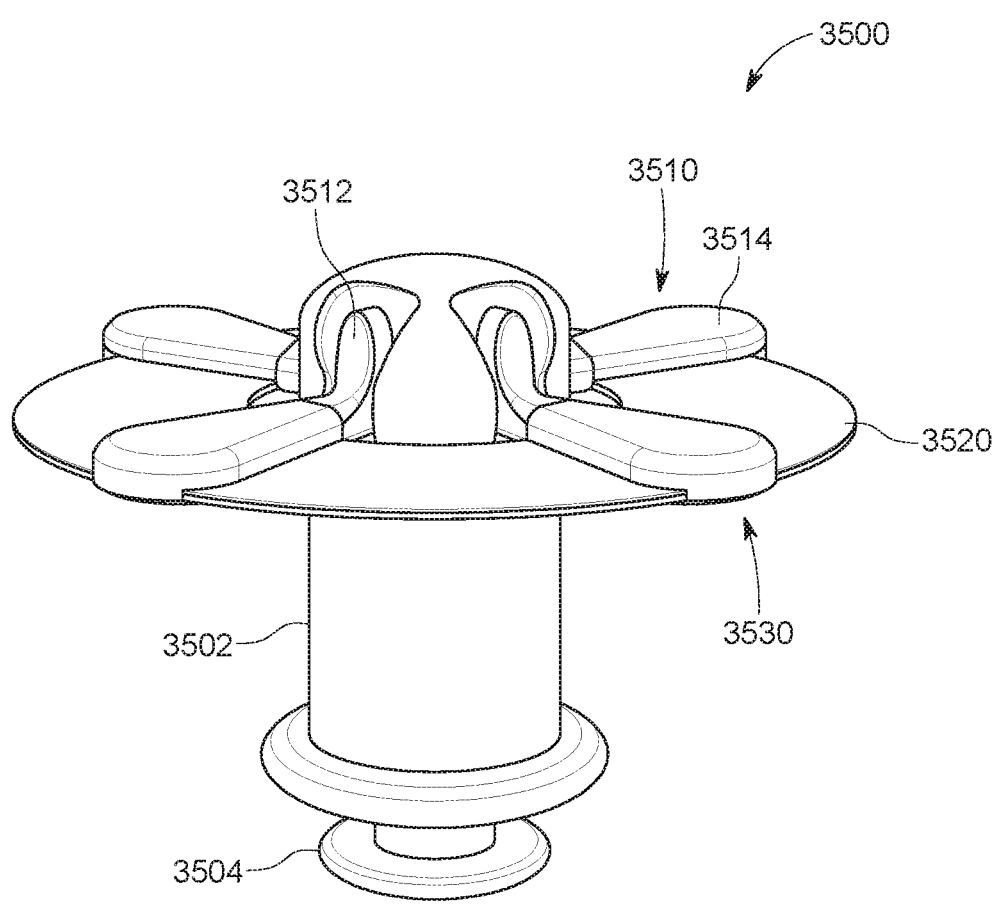
FIG. 35 is a perspective view of a pessary with webbing between petals, according to an embodiment.

FIG. 35 is a perspective view of a pessary with webbing between petals, according to an embodiment. A pessary 3500 can have a stem 3502, a plunger 3504, petal members 3510 with short segments 3512 and elongated segments 3514, and a petal webbing 3520. The petal webbing 3520 can connect the petal members 3510, thereby forming a unitary petal member 3530. The petal members 3510 and the petal webbing 3520 together can form a supportive surface that can work together to support the pelvic organs. The petal webbing 3520 can be made of a silicone or other deformable material, so that the petal webbing 3520 can fold when the pessary 3500 is transitioned into the collapsed state. The petal webbing 3520 can at least partially envelop the elongated segments 3514 with the silicone or other material, as well as providing additional supportive material between the elongated segments 3514. The petal webbing 3520 is depicted in FIG. 35 as a solid disc, however, the petal webbing can be a series of concentric rings connecting the petal members 3510, or the petal webbing 3520 can be a net or a mesh, or other arrangements of material connecting the petal members 3510. In various embodiments, unitary petal members such as the unitary petal members shown in FIGS. 20-26 can be used in place of the unitary petal member 3520 shown in FIG. 35.

Figure 36:
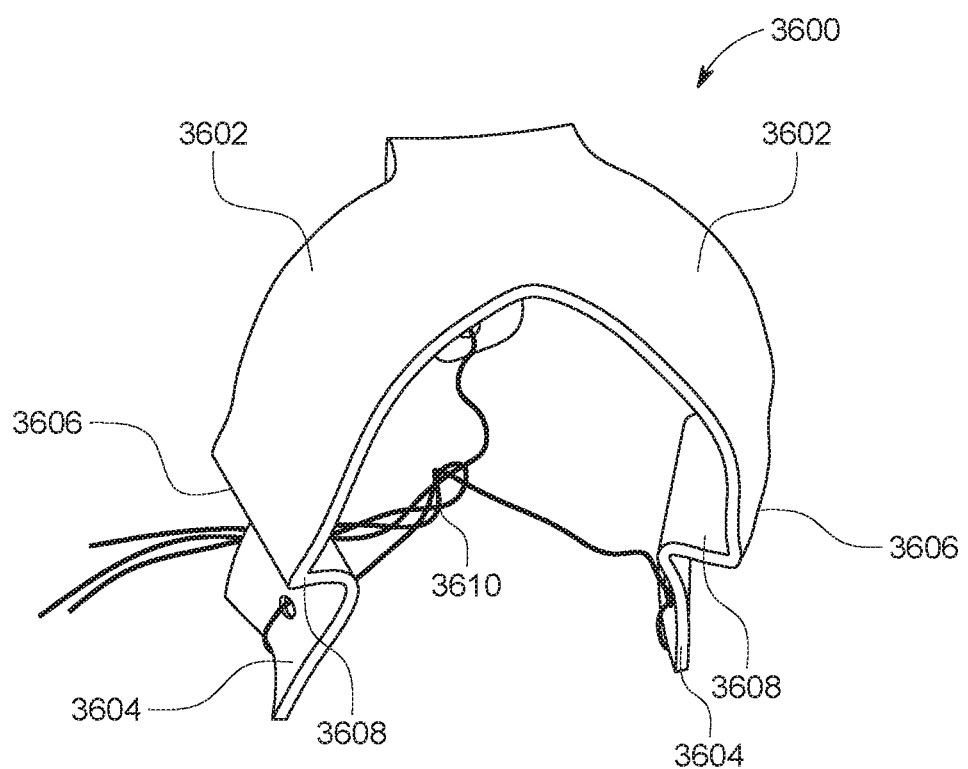
FIG. 36 is a perspective view of a domed pessary with resilient deformable petals, according to an illustrative embodiment.

FIG. 36 is a perspective view of a domed pessary with resilient deformable petals, according to an illustrative embodiment. A pessary 3600 can have three or more resilient deformable petal members 3602 that can be joined at the top. Resilient deformable petal members 3602 can be ribs defining a curved dome shape. Resilient deformable petal members 3602 can be connected by a skin (not shown) forming a dome, and the skin can be a silicone overmolding, or other soft flexible material such as silicone. Resilient deformable petal members 3602 can have indented finger tabs 3604. A resilient deformable petal member 3602 can have an outer perimeter 3606, a recess portion 3608, and a finger tab 3604, so that a radius distance from a central vertical axis to the outer perimeter 3606 is greater than a radius distance from the central vertical axis to the finger tab 3604. The pessary 3600 can be inserted by pinching the finger tabs 3604 towards each other to decrease the overall diameter of the pessary 3600, including the diameter at the outer perimeter 3606. Once the pessary 3600 is inserted, the finger tabs 3604 can be released and the pessary can return to the resting state shown in FIG. 36. To remove the pessary 3600, the finger tabs 3604 can be pinched towards each other to decrease the overall diameter of the pessary 3600.

In various embodiments, a lower portion of the deformable petal members 3602 can be connected by a string 3610 that can be a silicone, a nylon material with a silicone coating, or other material. String 3610 can be connected to each petal member 3602, and the strings from each petal member can be joined together. The pessary can be removed by pulling on the string 3610. Pulling on the string 3610 can cause the resilient deformable petal members 3602 to move towards each other and decrease the overall diameter of the pessary 3600, including the diameter at the outer perimeter 3606. Pulling on the string 3610 can also exert a force on the pessary 3600 to remove the pessary as the deformable petal members 3602 have moved towards each other.

Figure 37:
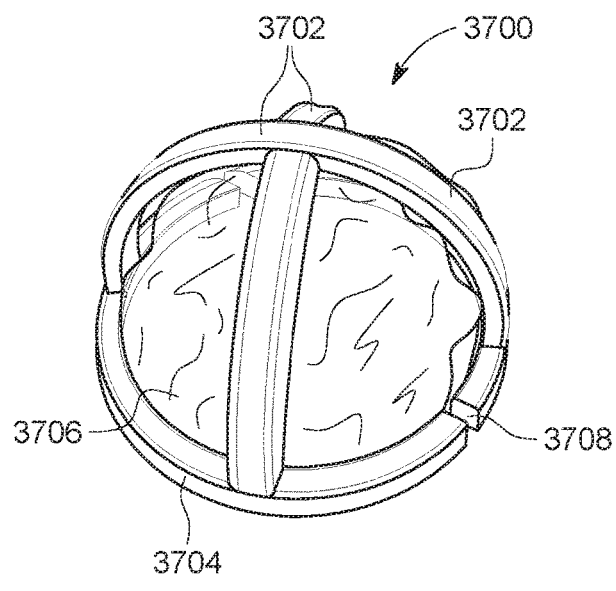
FIG. 37 is a perspective view of a pessary with resilient deformable members connected to a base ring, according to an embodiment.

FIG. 37 is a perspective view of a pessary with resilient deformable members connected to a base ring, according to an embodiment. A pessary 3700 can have 3 or more resilient deformable petal members 3702 that can be joined at the top, and can be connected to a base ring 3704. Resilient deformable petal members 3702 can be ribs forming a curved dome shape. A soft skin 3706 can connect the resilient deformable petal members 3702 and/or the base ring 3704. Soft skin 3706 can be a soft plastic, a silicone, or other biocompatible material. Base ring 3704 can have one or more ring breaks 3708 in the internal structure of the base ring 3704 to allow the base ring 3704 to be collapsed for easier insertion and removal of the pessary 3700. Base ring 3704 can be overmolded with silicone or other soft biocompatible material, and the silicone can cover or encapsulate the ring breaks 3708. Ring breaks 3708 may not be complete cuts or gaps, but can be portions of the ring that are thinner or otherwise weakened to allow easy collapsibility. In various embodiments, the pessary 3700 can have recess portions and finger tabs to ease removal. In various embodiments, the pessary 3700 can have strings connecting multiple lower portions of the base ring 3704 or finger tabs, and the strings can be connected together. Pulling on the string can help to collapse the base ring 3704 and can help to remove the pessary 3700.

Figure 38A:
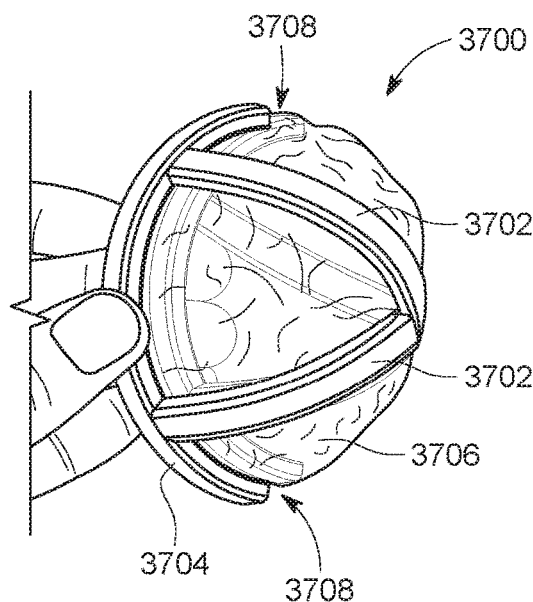
FIG. 38A is a side view of the domed pessary of FIG. 37 shown in a collapsed conformation, according to an illustrative embodiment.
Figure 38B:
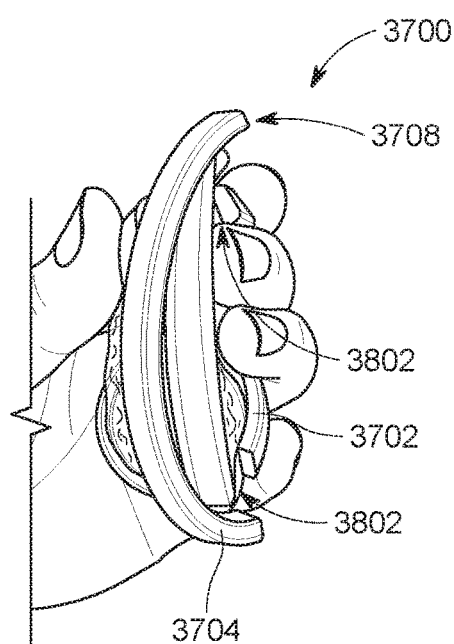
FIG. 38B is a bottom view of the domed pessary of FIG. 37 shown in a collapsed conformation, according to an illustrative embodiment.
Figure 38C:
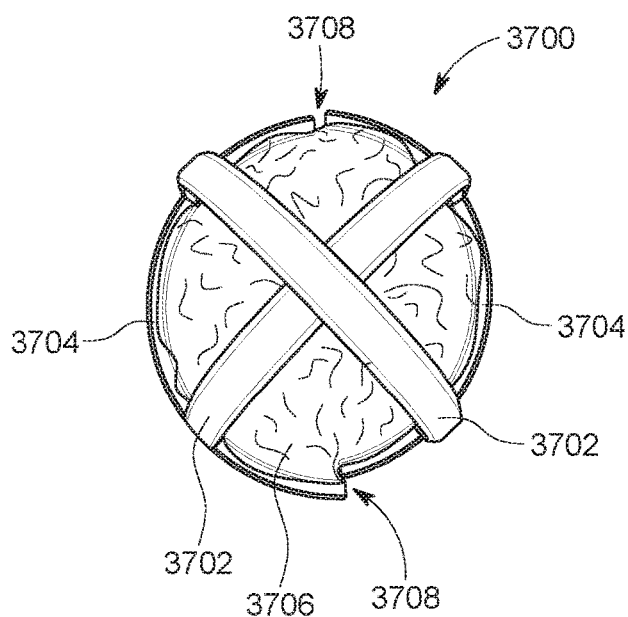
FIG. 38C is a top view of the domed pessary of FIG. 37 shown in a deployed conformation.

FIG. 38A is a side view of the domed pessary of FIG. 37 shown in a collapsed conformation, according to an illustrative embodiment. A user can flatten or otherwise collapse the pessary 3700 by squeezing sides of the base ring 3704 together and collapsing the base ring 3704 at the ring breaks 3708. Ring breaks 3708 are shown exposed and without silicone overmolding in FIG. 38A for clarity, but it should be clear that ring breaks 3708 can be encapsulated to avoid protruding edges. FIG. 38B is a bottom view of the domed pessary of FIG. 37 shown in a collapsed conformation, according to an illustrative embodiment. The base ring 3704 can have two or more ring breaks 3708 to allow easy collapsibility for ease of insertion. Pessary 3700 can have petal breaks 3802 where the resilient deformable petal members 3702 meet the ring 3704. Petal breaks 3802 can allow the pessary 3700 to collapse more fully for ease of insertion. The pessary 3700 can be overmolded with silicone or other soft biocompatible material, and the silicone can cover or encapsulate the petal breaks 3802. Petal breaks 3802 may not be complete cuts or gaps, but can be portions of the resilient deformable petal members 3702 that are thinner or otherwise weakened to allow easy collapsibility. When the pessary 3700 is released, the resilient deformable petal members 3702 can bias the pessary into the deployed conformation shown in FIG. 37. FIG. 38C is a top view of the domed pessary of FIG. 37 shown in a deployed conformation. When a user releases the pessary, the resilient deformable petal members 3702 can return to their unstressed conformation and can bias the pessary 3700 into the deployed conformation.

Figure 39A:
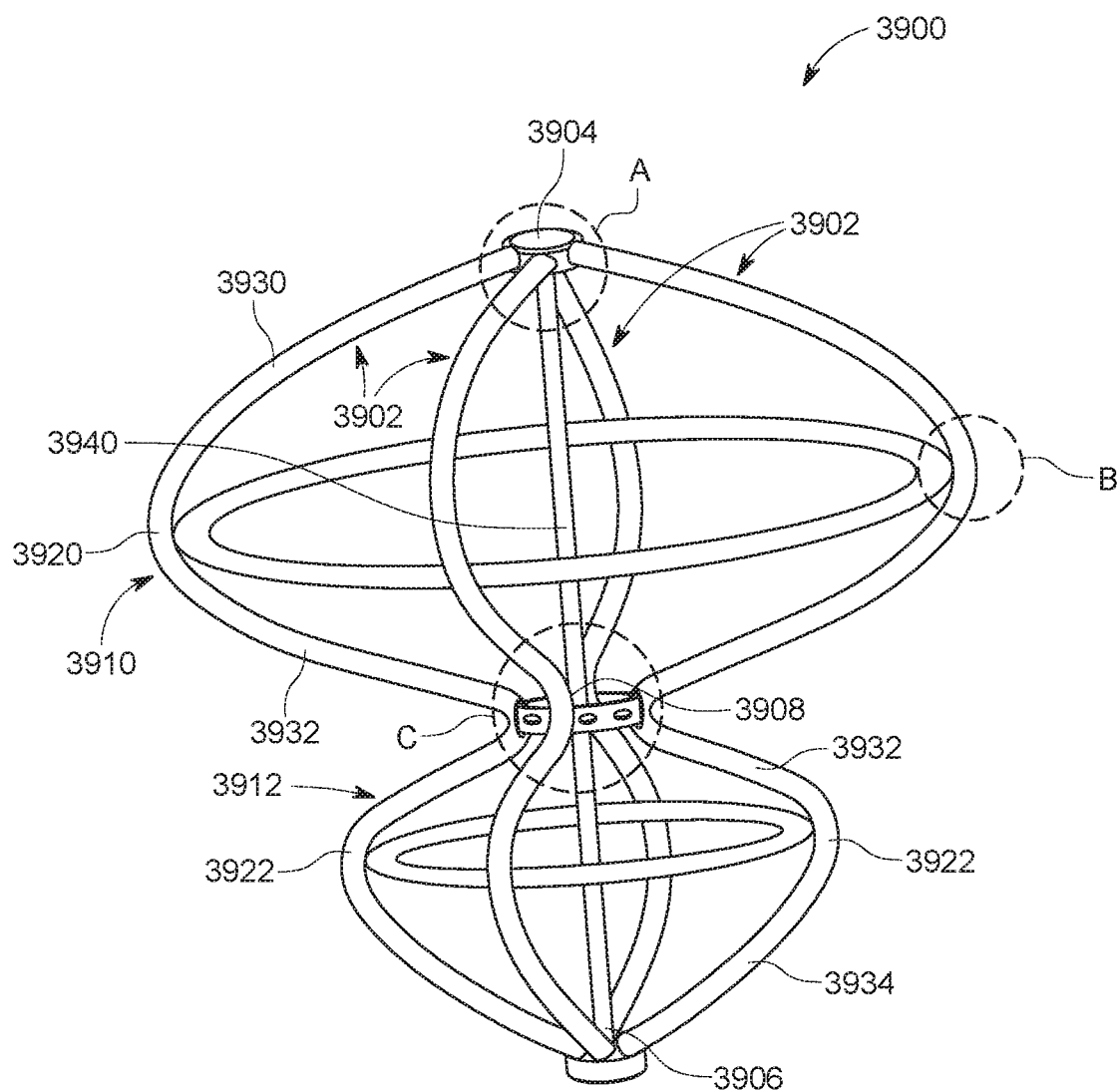
FIG. 39A is a diagram of a figure-eight pessary in a deployed conformation, according to an illustrative embodiment.

FIG. 39A is a diagram of a figure-eight pessary in a deployed conformation, according to an illustrative embodiment. A figure eight-shaped pessary 3900 in a deployed conformation can have a structural frame with three or more helical petal members 3902. The exemplary figure-eight pessary in FIG. 39A is shown with four helical petal members 3902. The helical petal members 3902 can be joined at the apex 3904 and at the bottom 3906. The figure-eight pessary 3900 can have a central union 3908, and the helical petal members 3902 can be hingedly joined at the central union 3908. The portion of the figure-eight pessary 3900 between the apex 3904 and the central union 3908 can be a supportive portion 3910, and the portion of the pessary between the central union 3908 and the bottom 3906 can be a pinchable handle portion 3912.

A helical petal member 3902 can have an upper hinge 3920 at the largest diameter section of the supportive portion, and a lower hinge 3922 at the largest diameter section of the pinchable handle portion. The region of the petal member 3902 between the upper hinges 3920 and the apex 3904 can be a top region 3930, the region of the petal member 3902 between the upper hinges 3920 and the lower hinges 3922 can be a middle region 3932, and the region of the petal member 3902 between the lower hinges 3922 and the bottom 3906 can be a lower region 3934. The upper region 3930 can provide support for the pelvic organs.

The apex 3904 and the bottom 3906 can be connected with a tensioner 3940. Tensioner 3940 can include an elastic cord or a tension spring between the apex 3904 and the bottom 3906. The tension force between the apex 3904 and the bottom 3906 can bias the pessary into the deployed conformation shown in FIG. 39A. The figure-eight pessary 3900 can have a silicone overmolding, and the silicone overmolding can be molded over the frame in the deployed conformation, so that the silicone overmolding can bias the figure-eight pessary 3900 in the deployed conformation. The frame of the pessary 3900 can be molded or otherwise constructed in the deployed conformation, so that the frame biases the pessary 3900 into the deployed conformation. The figure-eight pessary 3900 can be collapsed by pinching the lower portion of the figure-eight pessary, and the figure-eight pessary can return to a resting deployed conformation when the lower portion is released.

Figure 39B:
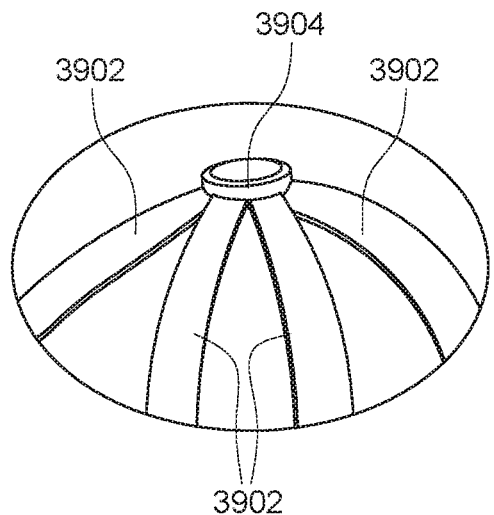
FIG. 39B is a detailed view of the apex region A from FIG. 39A, according to an illustrative embodiment.

FIG. 39B is a detailed view of the apex region A from FIG. 39A, according to an illustrative embodiment. In various embodiments, the apex 3904 and/or bottom 3906 can be molded or otherwise constructed with a resilient deformable unitary joint between the petal members 3902. The frame can be molded with a unitary apex 3904 with the petal members 3902 extending outward in the deployed conformation. The resilient deformable unitary joint can be semi-rigid, and can bias the frame into the deployed conformation.

Figure 39C:
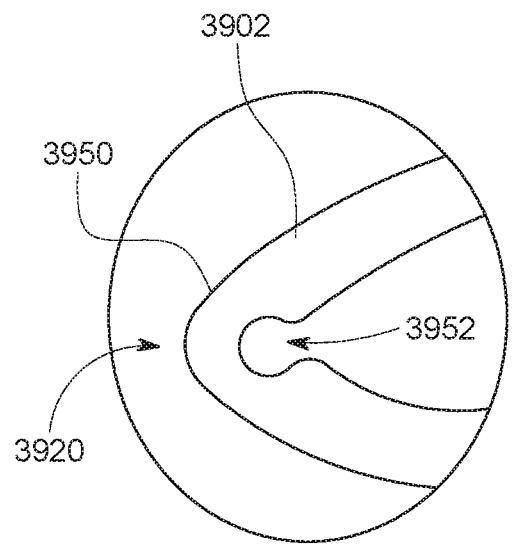
FIG. 39C is a detailed view of the hinge region B from FIG. 39A, according to an illustrative embodiment.

FIG. 39C is a detailed view of the hinge region B from FIG. 39A, according to an illustrative embodiment. In various embodiments, upper hinge 3920 and/or lower hinge 3922 can be a unitary hinge. A portion of the petal member 3902 can be removed to create a thinner section 3950, or the petal member can be molded with a thinner section 3950 and a gap 3952. The living hinge can allow the frame to bend easily into the deployed conformation.

Figure 39D:
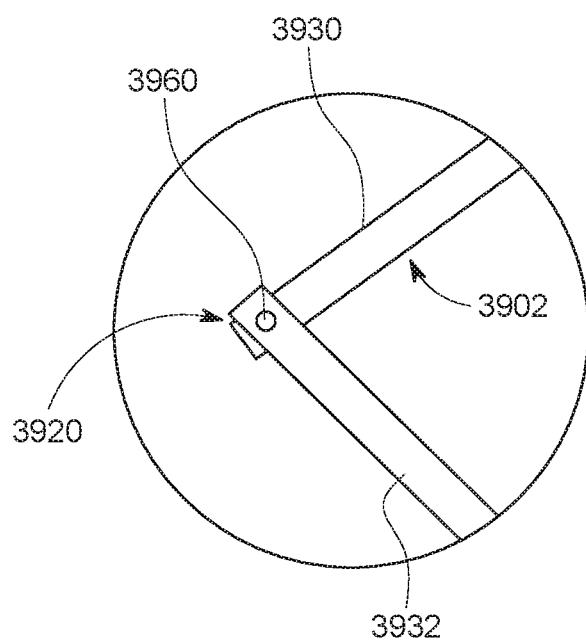
FIG. 39D is a detailed view of the hinge region B from FIG. 39A, according to another illustrative embodiment.

FIG. 39D is a detailed view of the hinge region B from FIG. 39A, according to another illustrative embodiment. In various embodiments, the upper region 3930, middle region 3932, and lower region 3934 of the petal members 3902 can be distinct components. A pivoting hinge can connect the upper region 3930 and the middle region 3932, so that the regions of the petal members can rotate freely relative to each other, and/or a pivoting hinge can connect the middle region 3932 and the lower region 3934 of the petal members so that the regions of the petal members can rotate freely relative to each other. The pivoting hinge can include a pin 3960 connecting regions of the petal member so that the regions of the petal member can rotate around the pin 3960.

Figure 39E:
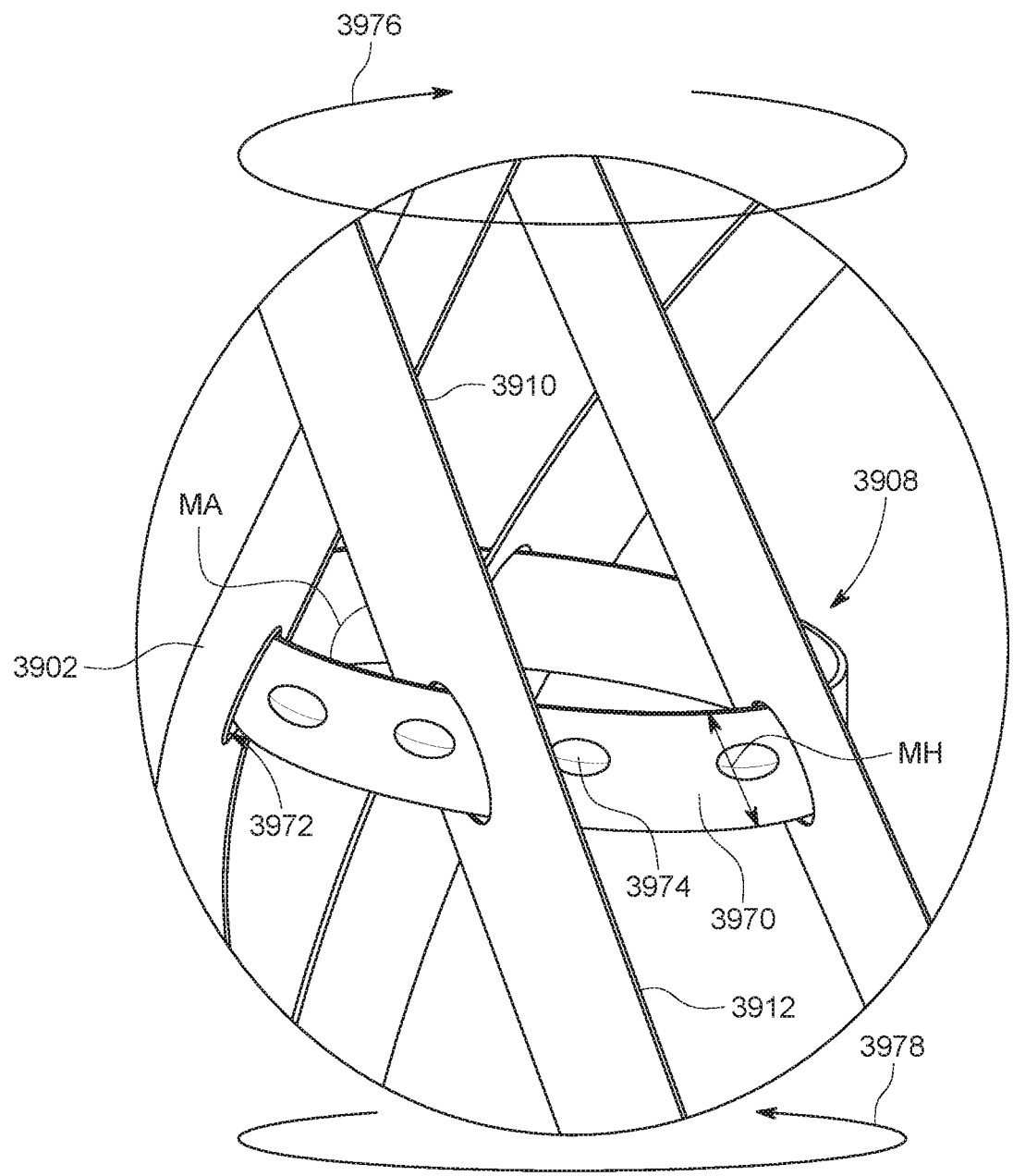
FIG. 39E is a detailed view of the central union region C from FIG. 39A, according to an illustrative embodiment.

FIG. 39E is a detailed view of the central union region C from FIG. 39A, according to an illustrative embodiment. In various embodiments, a central union 3908 can include a union ring 3970. Union ring 3970 can have a rectangular cross section, and the petal members 3902 can have mating slots 3972 that can be sized and shaped to accommodate the union ring 3970. The mating slots 3972 can define at least a portion of a shape that is larger than the cross section of the union ring 3970, so that the union ring 3970 can be snapped into the slots 3972, and the slots 3972 can retain the union ring 3970. The union ring can have mechanical stops 3974 that can be bumps or other extensions outward from the union ring between the petal members 3902. The mechanical stops 3974 can prevent the petal members 3902 from sliding around the union ring 3970.

The supportive portion 3910 of the petal members 3902 can rotate, or lean over, along arrow 3976 to reach the fully deployed conformation, while the pinchable handle portion 3912 of the petal members 3902 can rotate, or lean, along arrow 3978 to reach the fully deployed conformation. In a fully deployed conformation, petal members 3902 can be at a minimum angle MA relative to the union ring 3970, and the upper diameter of the supportive portion of the frame at the upper hinges 3920 can be at the maximum diameter. The mating slots 3972 can have a maximum height MH that can limit how far the petal members can rotate relative to the union ring 3970, thereby limiting the maximum diameter of the supportive portion at the upper hinges. Limiting the maximum diameter of the supportive portion can increase comfort for the user of the pessary. When the user pinches the pinchable handle region of the frame in a region that can include the lower hinges 3922, the petal members can rotate relative to the union ring 3970 in a direction opposite to arrows 3976 and 3978, and the angle of the petal members 3902 relative to the union ring 3970 can increase.

Figure 40B:
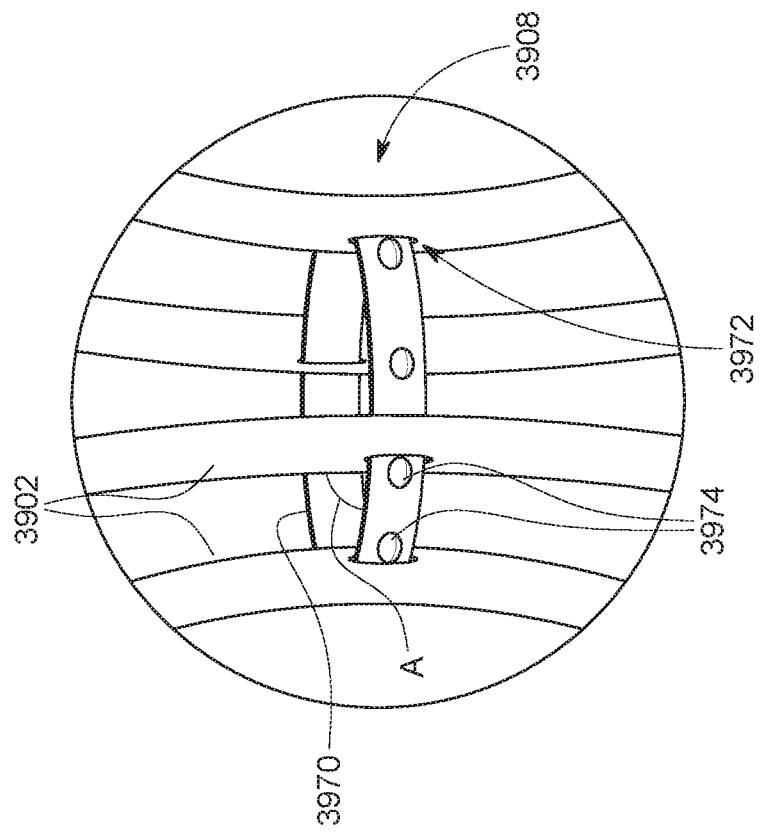
FIG. 40B is a detailed view of the central union region A from FIG. 40A, according to an illustrative embodiment.
Figure 40A:
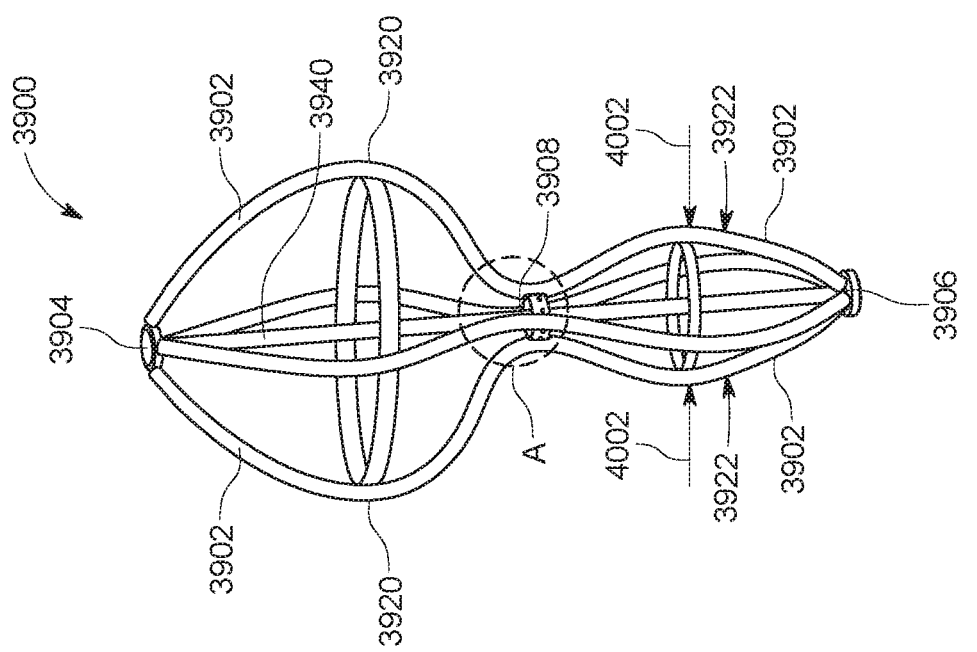
FIG. 40A is a diagram of a figure-eight pessary in a collapsed conformation, according to an illustrative embodiment.

FIG. 40A is a diagram of a figure-eight pessary in a collapsed conformation, according to an illustrative embodiment. In the collapsed state, the petal members 3902 have been deformed out of the helical shape of the deployed conformation, and are now in a more vertical arrangement. A user can apply a pinching force along arrows 4002 at or near the lower hinges 3922 to squeeze the lower hinges 3922 towards each other, thereby elongating the pessary 3900, and decreasing the diameter of the pessary 3900 at the upper hinges 3920.

The petal members 3902 can be molded into the helical shape shown in FIG. 39A, so that a force is required to deform the petal members 3902 out of the helical shape and into the shape shown in FIG. 40A, and the molded shape of the petal members 3902 can bias the pessary 3900 back into the deployed conformation of FIG. 39A when the pessary 3900 is released by the user. A silicone overmolding can be molded over the pessary 3900 in the deployed conformation, and the silicone overmolding can bias the pessary into the deployed conformation. A unitary joint at the apex and/or the bottom of the pessary can bias the pessary into the deployed conformation. A tensioner can bias the pessary into the deployed conformation.

FIG. 40B is a detailed view of the central union region A from FIG. 40A, according to an illustrative embodiment. Petal members 3902 are now in a more vertical arrangement, and petal members 3902 are at a maximum angle XA relative to the union ring. Mating slots 3972 are taller than the union ring 3970, and now have extra space at the top and/or bottom the mating slot 3972. The width of the mating slots 3972 can be approximately the same as the width of the cross section of the union ring 3970, so that the petal members can pivot side to side, but cannot rock in and out. Mechanical stops 3974 prevent the petal members 3902 from sliding around the union ring 3970.

Figure 41:
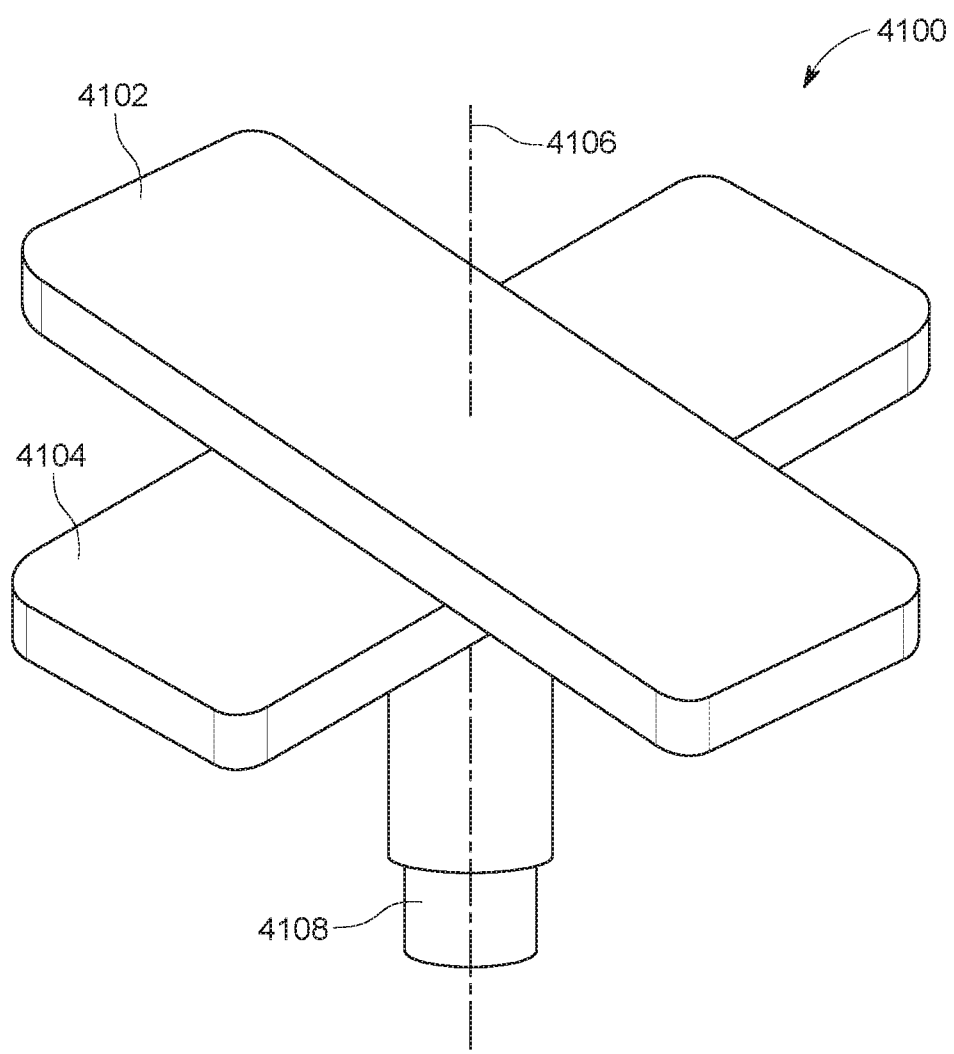
FIG. 41 is a diagram of a pessary with petals that rotate about a central axis, according to an illustrative embodiment.

FIG. 41 is a diagram of a pessary with petals that rotate about a central axis, according to an illustrative embodiment. A pessary 4100 can have at least two rigid petals 4102, 4104 that can rotate about a central axis 4106. In the deployed state, the upper petal 4102 can be rotated into a position that is rotationally remote from the lower petal 4104. In various embodiments, pessary 4100 can have a knob 4108 that can be rotated to rotate the lower petal 4104 from the collapsed state to the deployed state relative to the upper petal 4102, and/or from the deployed state to the collapsed state. Various means can be used for biasing the pessary into a deployed state.

Figure 42A:
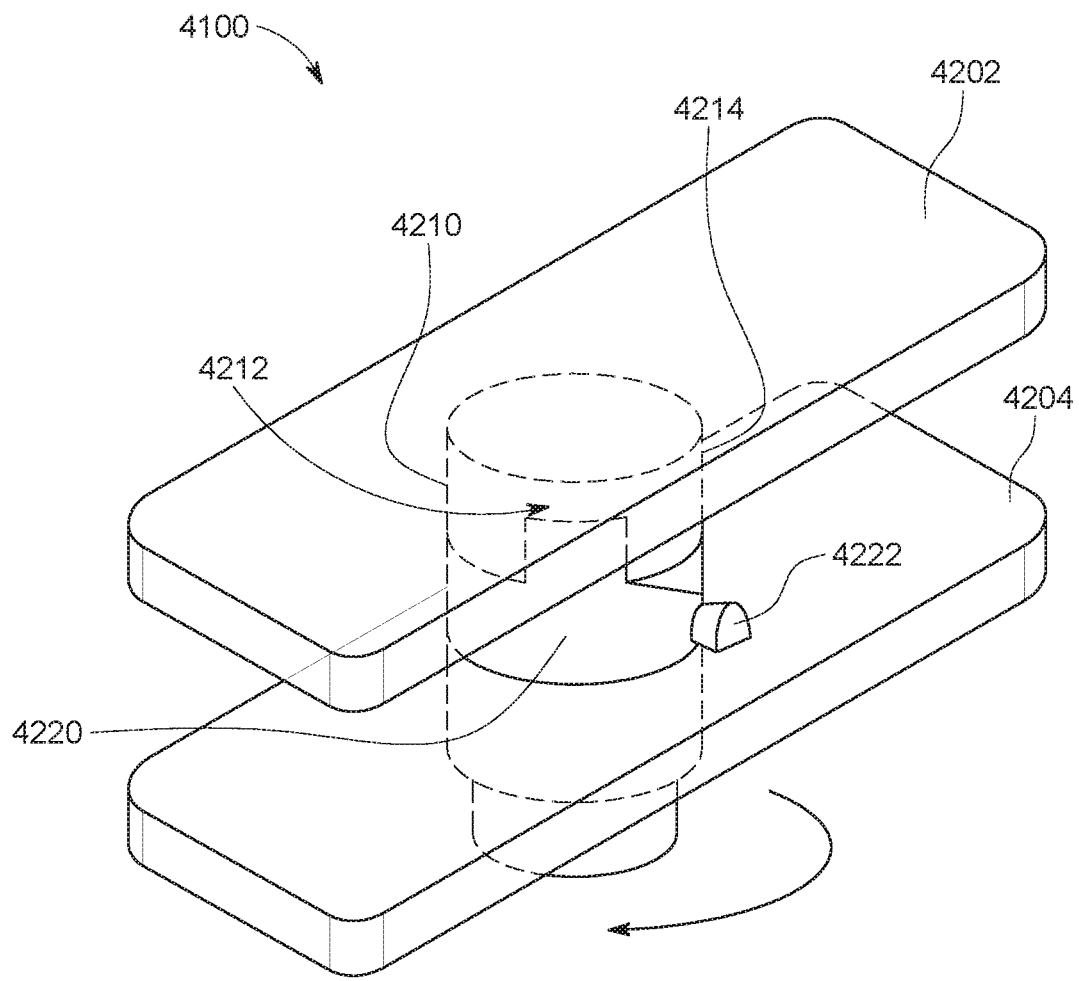
FIG. 42A is a partially cutaway diagram of the pessary of FIG. 41 showing inner workings of the pivoting hinge and shown in a collapsed state, according to an illustrative embodiment.

FIG. 42A is a partially cutaway diagram of the pessary of FIG. 41 showing inner workings of the pivoting hinge and shown in a collapsed state, according to an illustrative embodiment. In a collapsed state, the lower petal 4104 can be parallel to the upper petal 4102. The upper petal 4102 can have an upper hinging member 4210, and the lower petal 4104 can have a lower hinging member 4220. The lower hinging member 4220 can have a tooth 4222 extending radially outward from the lower hinging member 4220. The upper hinging member 4210 can have a locking recess 4212 and a slide 4214. The upper petal 4102 can be biased towards the lower petal 4104 by various means that can include a tensioner such as a tension spring inside of the hinge, or a silicone overmolding surrounding the pivoting hinge that has been molded around the pivoting hinge in the deployed position. As the upper petal 4102 and the lower petal member 4104 are biased towards each other, the lower petal 4104 rotates along arrow 4230 relative to the upper petal 4202, and the tooth 4222 is urged along the slide 4214 and into the locking recess 4212. When the tooth 4222 is in the locking recess 4212 the pessary is in a relaxed and deployed state.

Figure 42B:
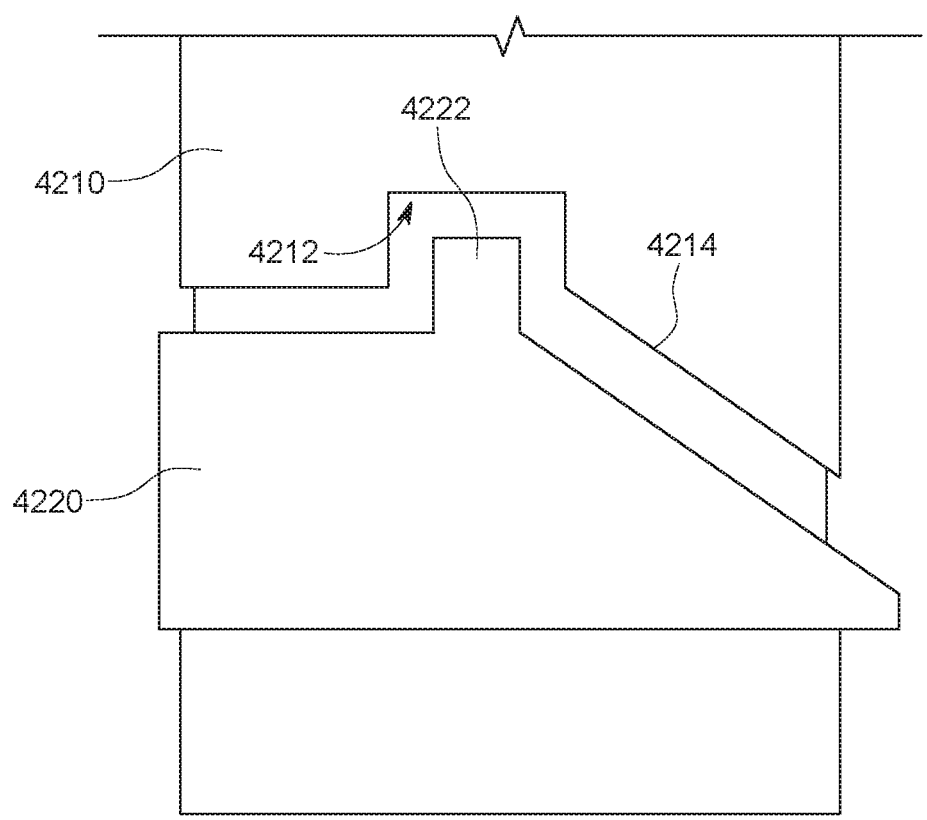
FIG. 42B is a cutaway view of a central pivoting hinge for the pessary of FIG. 41 showing inner workings and shown in a deployed state, according to an illustrative embodiment.

FIG. 42B is a cutaway view of a central pivoting hinge for the pessary of FIG. 41 showing inner workings and shown in a deployed state, according to an illustrative embodiment. In the deployed state, the tooth 4222 is held within the locking recess 4212. The upper hinging member 4210 and the lower hinging member 4220 are biased towards each other, thereby holding the tooth 4222 within the locking recess 4212.

FIG. 43 is a cutaway view of a central pivoting hinge for the pessary of FIG. 41 showing inner workings and in a deployed state, according to another illustrative embodiment. Pessary 4100 can have a compression spring 4302 that can bias the lower petal 4104 away from the upper petal 4102, and the pessary 4100 can have a retention lip 4304 that can retain the lower petal 4104 together with the upper petal 4102, thereby limiting how far the compression spring 4302 can force the lower petal 4104 away from the upper petal 4102. The lower petal 4104 can have a groove 4306 that can travel along a thread 4308 on the upper petal 4102. In the relaxed and deployed state shown in FIG. 43, the compression spring has forced the lower petal 4104 to rotate and travel downwards along thread 4308, and the lower petal 4102 is at the most distant point from the upper petal 4104. To insert the pessary, a user can rotate the lower petal 4104 upwards and around the thread 4308 into the collapsed state, and when the user releases the pessary the compression spring 4302 can return the pessary to the deployed state.

Figure 44:
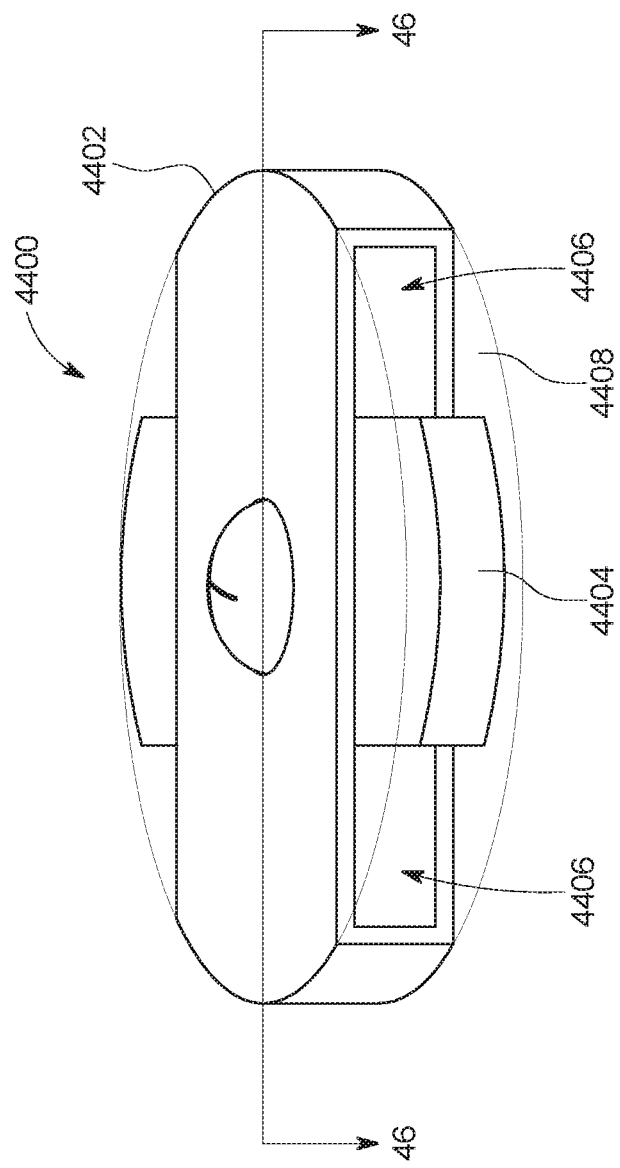
FIG. 44 is a perspective view of a pessary with enclosed rotating petals, according to an illustrative embodiment.
Figure 45:
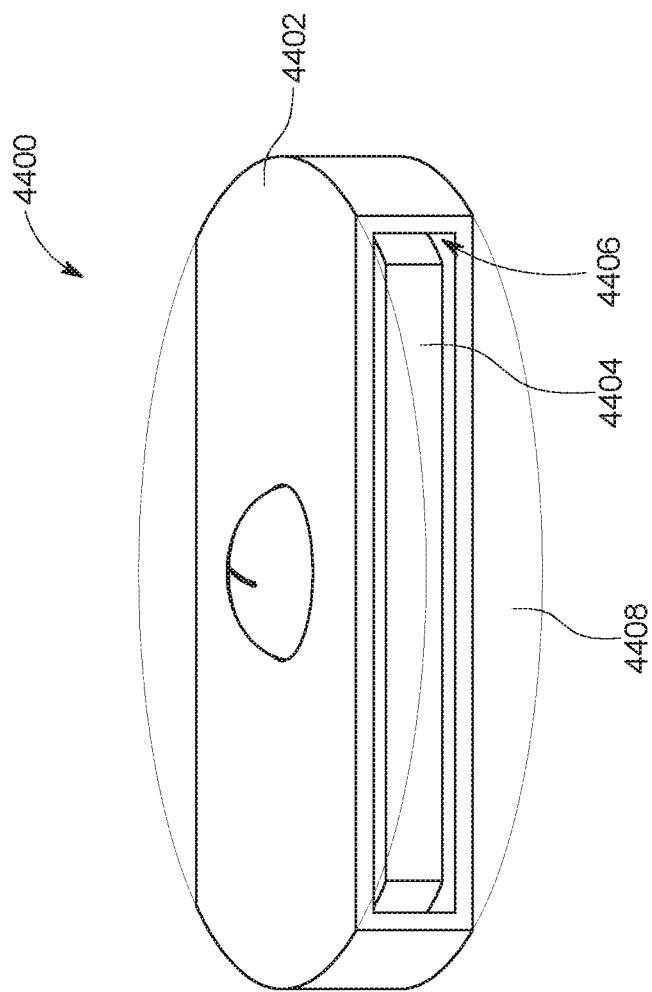
FIG. 45 is a perspective view of the pessary of FIG. 44, shown in the collapsed state.
Figure 46:
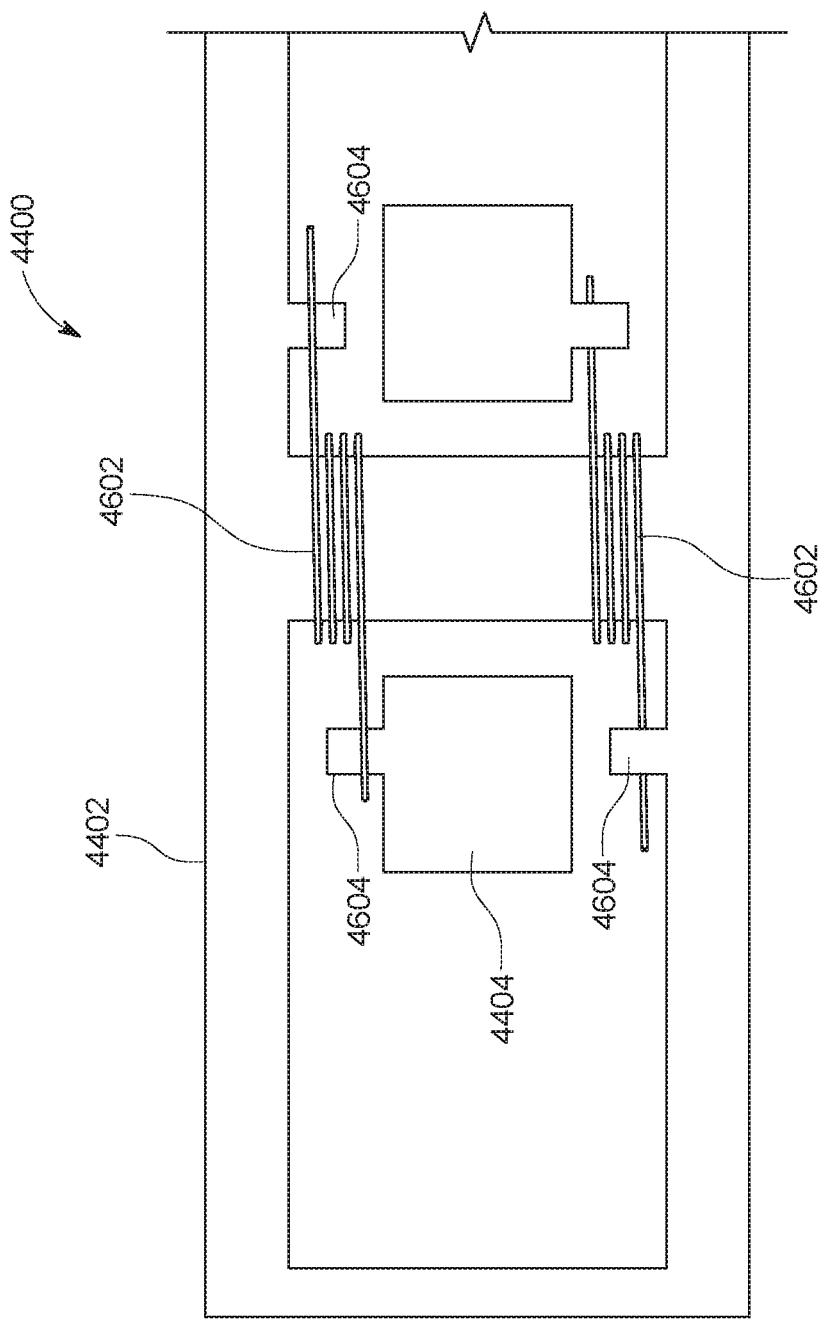
FIG. 46 is a cross section of the pessary of FIG. 44 in the deployed state, taken along line 46-46 of FIG. 44, according to an illustrative embodiment.

FIG. 44 is a perspective view of a pessary with enclosed rotating petals, according to an illustrative embodiment. A pessary 4400 can have an outer petal 4402 and an inner petal 4404 that can rotate relative to each other around a central axis. The outer petal 4402 can be a rigid member with an inner chamber 4406 that can accommodate the inner petal 4402. Outer petal 4402 can be overmolded with a silicone casing 4408 that can encapsulate the outer petal 4402 and the inner petal 4404. In various embodiments, the silicone overmolding can have holes that can allow for drainage. The inner petal 4404 can be rotationally remote from the inner petal 4404 in the deployed state shown in FIG. 44. FIG. 45 is a perspective view of the pessary of FIG. 44, shown in the collapsed state. Inner petal 4404 can rotate into the inner chamber 4406 of the outer petal 4402. Rotating the inner petal 4404 into the inner chamber 4406 can decrease the size of the pessary so that it can be inserted into the vaginal canal. FIG. 46 is a cross section of the pessary of FIG. 44 in the deployed state, taken along line 46-46 of FIG. 44, according to an illustrative embodiment. The pessary 4400 can have one or more torsion springs 4602 that can bias the inner petal 4404 into a deployed state that is rotationally remote from the outer petal 4402. The torsion spring 4602 can be connected to, or can press against, spring tabs 4604 on the outer petal 4402 and the inner petal 4404.

The pessary 4400 can be manufactured by molding the outer petal in two halves along line 46-46 of FIG. 44, and then overmolding the silicone casing around each half separately. The pessary 4400 can then be assembled by snapping the two halves of the outer petal together around the inner petal. An additional layer of silicone overmolding can then seal the snap at the seam.

Figure 47:
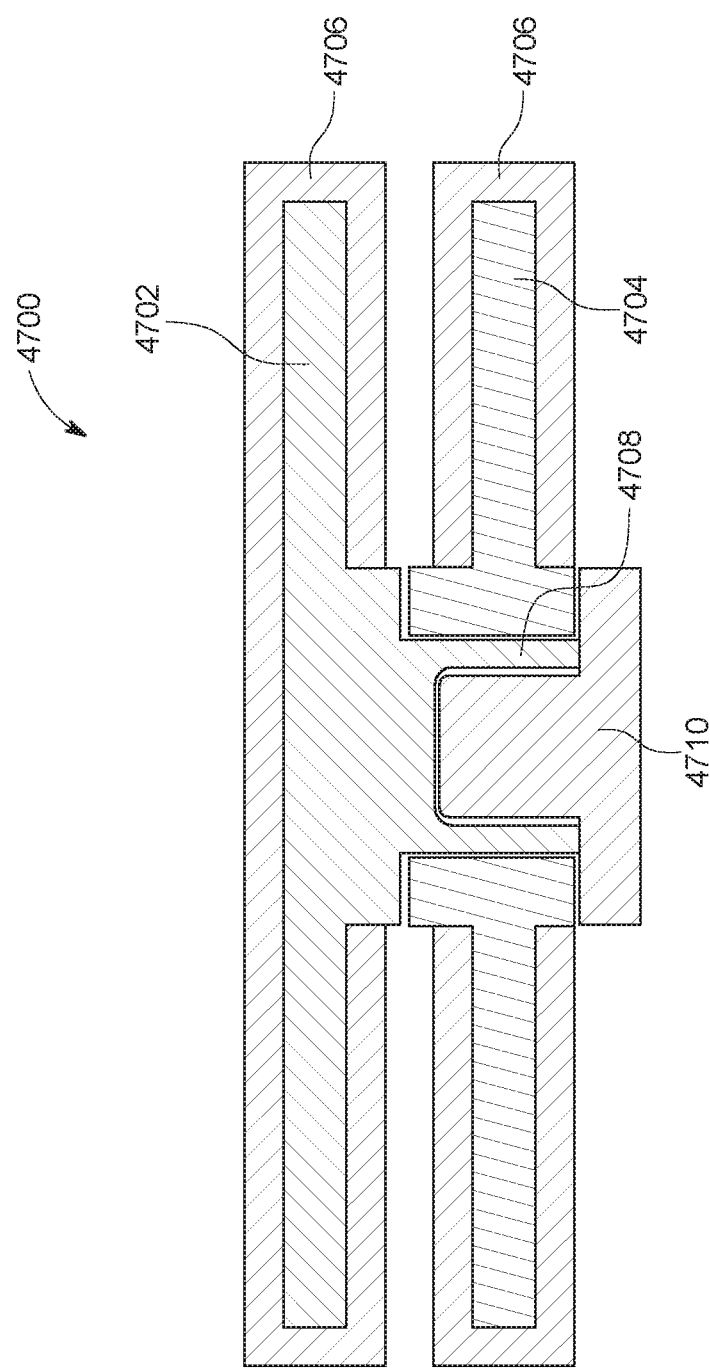
FIG. 47 is a partially cutaway view of a rotating pessary that can be disassembled for cleaning, according to an illustrative embodiment.

FIG. 47 is a partially cutaway view of a rotating pessary that can be disassembled for cleaning, according to an illustrative embodiment. A rotating pessary 4700 can have an upper petal 4702 and a lower petal 4704. Upper petal 4702 and lower petal 4704 can have a silicone overmolding 4706 that can increase comfort for the user. Upper petal 4702 can include an axle 4708, and the lower petal 4704 can rotate around the axle 4706. The pessary 4700 can have a removable endcap 4710. A user can remove the endcap 4710 from the axle 4708 to disassemble the pessary 4700. The lower petal 4704 can be separated from the upper petal 4702 so that each component can be cleaned separately.

Figure 48:
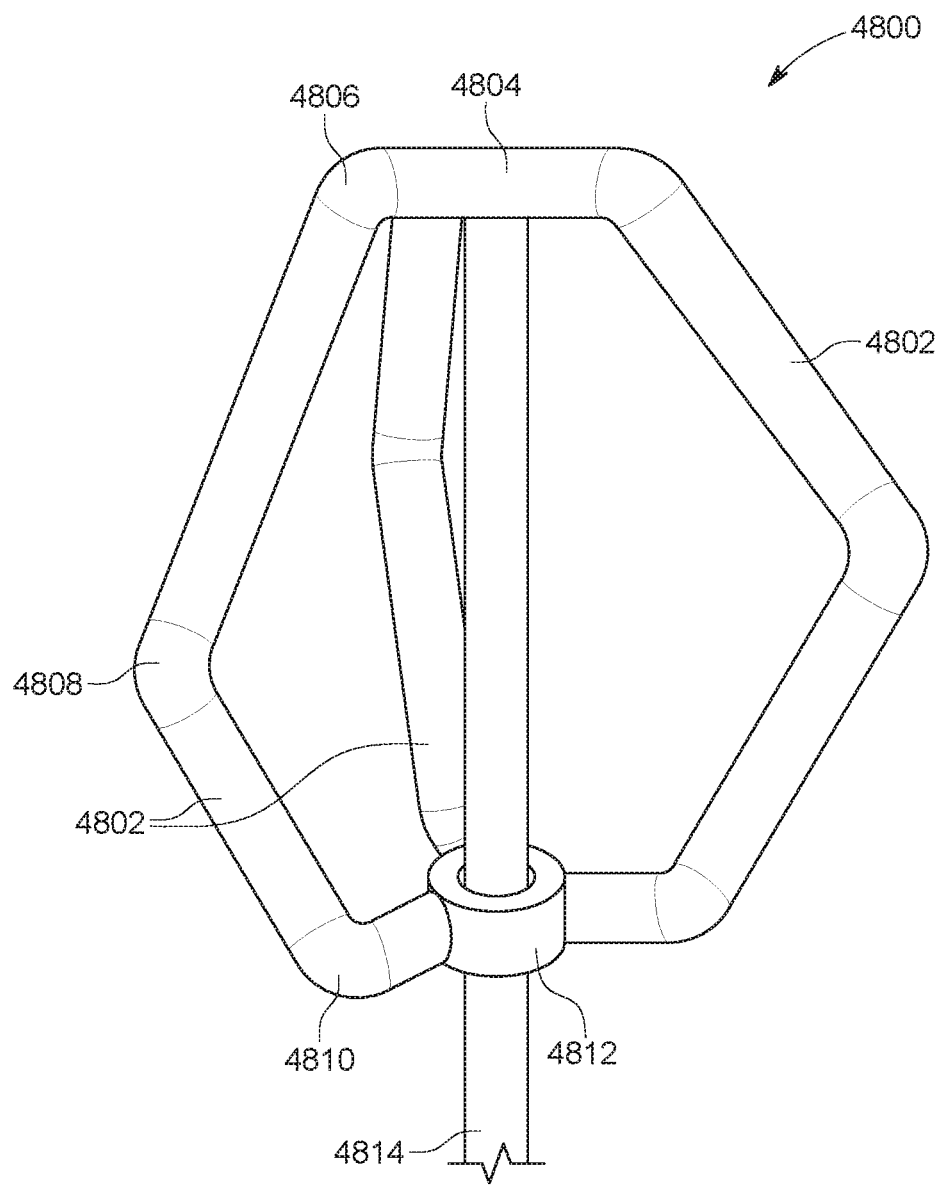
FIG. 48 is a perspective view of a pessary with a sliding ring lock, according to an illustrative embodiment.

FIG. 48 is a perspective view of a pessary with a sliding ring lock, according to an illustrative embodiment. A pessary 4800 can have three or more hinged petals 4802 that can be joined together at an apex 4804. Petal members 4802 can have an upper hinge 4806, a middle hinge 4808, and a lower hinge 4810. The petal members 4802 can be attached to a sliding ring 4812 that can slide along a central stem 4814. Sliding ring 4812 can slide along the central stem 4814 to move the pessary 4800 between a deployed state and a collapsed state. In various embodiments a silicone overmolding, or other soft material can surround the petal members 4802.

Figure 49:
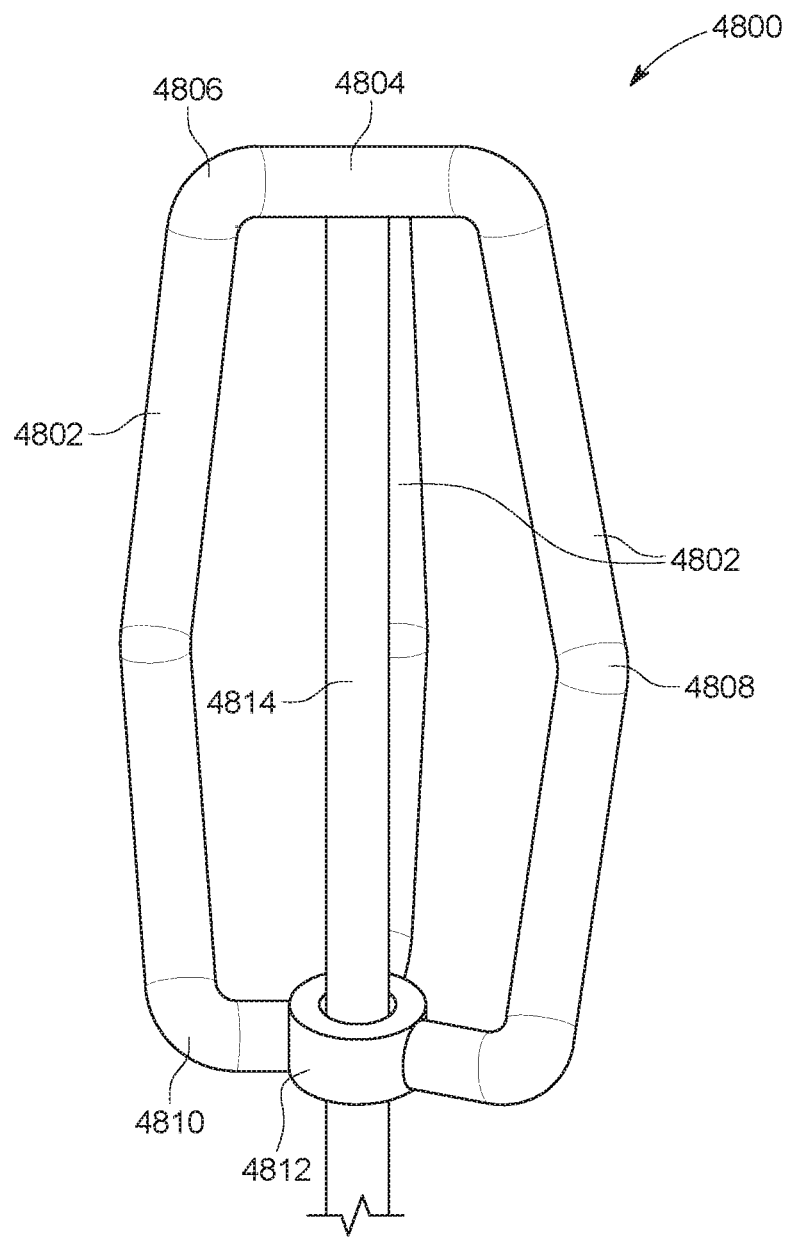
FIG. 49 is a perspective view of the pessary of FIG. 48 in a collapsed state, according to an illustrative embodiment.
Figure 50:
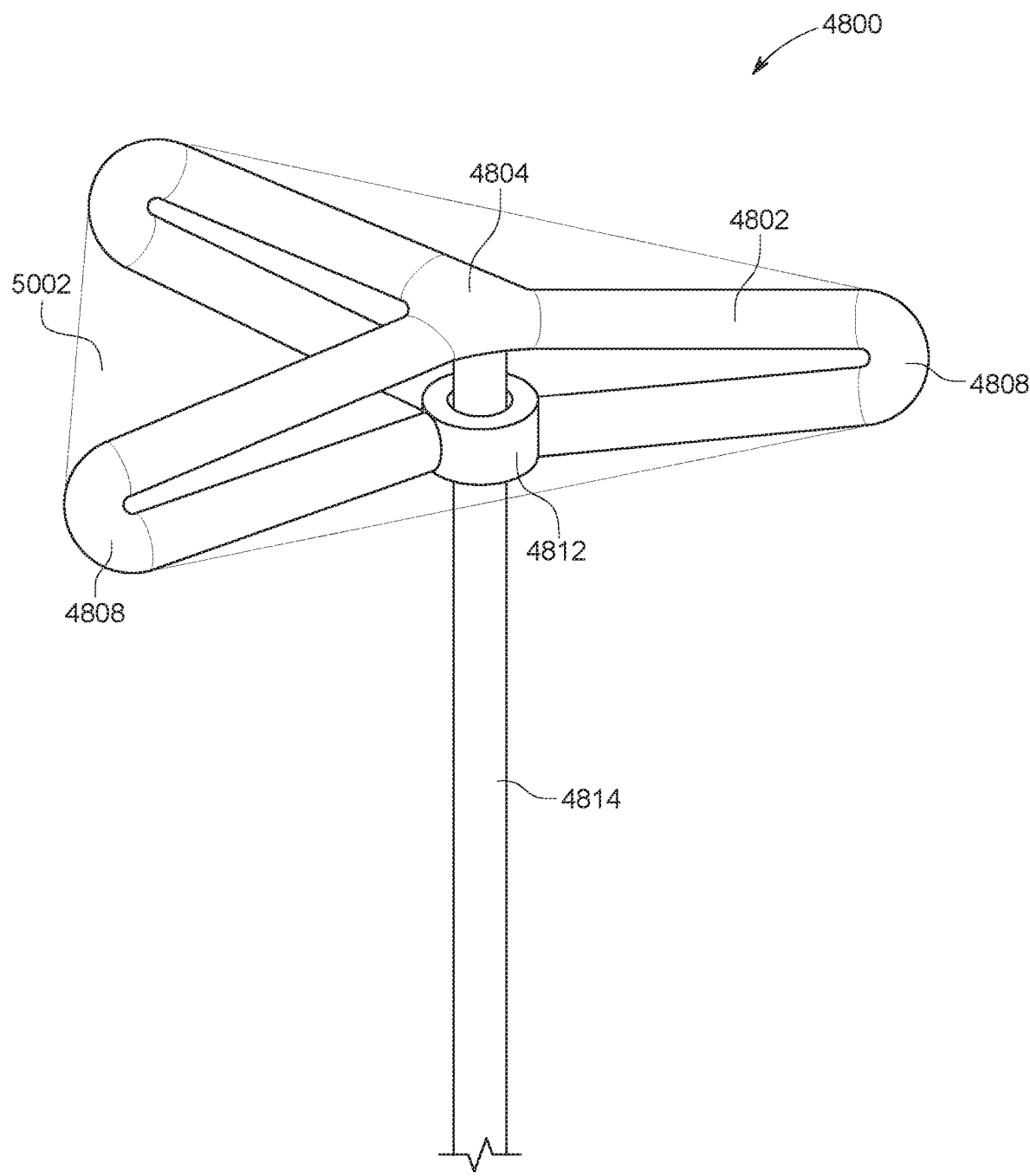
FIG. 50 is a perspective view of the pessary of FIG. 48 in a deployed state, according to an illustrative embodiment.

FIG. 49 is a perspective view of the pessary of FIG. 48 in a collapsed state, according to an illustrative embodiment. The sliding ring 4812 can be at the lowest position along the central stem 4814, and upper hinges 4806 and lower hinges 4810 can be bent. FIG. 50 is a perspective view of the pessary of FIG. 48 in a deployed state, according to an illustrative embodiment. The sliding ring can be at the highest position along the central stem 4814, and the middle hinges 4808 can be bent. In the deployed position, the petals 4802 are extending radially outward from the central stem, and the diameter of the pessary around the middle hinges 4808 is at a maximum diameter. In various embodiments, a silicone overmolding 5002 or other soft material that can surround the petals can be expanded outwards with the petals, so that the petals 3802 and the silicone overmolding together can support the pelvic organs.

FIG. 51A is a perspective view of a locking mechanism for the pessary of FIG. 48, according to an illustrative embodiment. The central stem 4814 can have one or more locking bumps 5102 that extend outwards from the stem 4814. Stem 4814 can be hollow and/or flexible, and stem 4814 can flex to allow the sliding ring 4812 to pass over the locking bumps 5102. The locking bumps 5102 can retain the sliding ring 4812 in the upward position, thereby locking the petals 4802 in the deployed state extending radially outward from the central stem 4814. A user can release the pessary 4800 from the deployed state by squeezing the stem 4814 inward along arrows 5104, so that the sliding ring 4812 can pass over the locking bumps 5102 and can slide downward on the stem 4814 into the collapsed state.

FIG. 51B is a partially cut away perspective view of a locking mechanism for the pessary of FIG. 48 and shown in a deployed state, according to another illustrative embodiment. The central stem of the pessary can include an outer sleeve 5110 and an inner slider 5112 that can slide, or telescope, within the outer sleeve 5110. The tops of the petals 4802 can be attached at a top of the slider, and the bottoms of the petals 4802 can be attached to the sleeve. Although only two petals are shown in FIG. 51B for clarity, it should be clear that the pessary can have more than two petals 4802. The inner slider 5112 can have a ridge 5114 or lip around at least a portion of the circumference of the inner slider 5112, and the outer sleeve 5110 can have one or more bumps 5116 or extensions that can extend inward from an interior wall of the slider. The bumps 5116 and the ridge 5114 can limit the movement of the pessary between a deployed state and a collapsed state, because a force must be exerted on the pessary to move the ridge 5114 past the bumps 5116. Additionally, the pessary can be molded so that it is biased to the deployed stage, or it can have a spring (not shown) biasing it to the deployed stage which stretches in the collapsed state.

51C is a partially cut away perspective view of a locking mechanism pessary of FIG. 51B and shown in a collapsed state, according to the illustrative embodiment. To collapse the pessary, a user can pull on the outer sleeve so that the bumps 5116 can move past the ridge 5114 and the outer sleeve 5110 can move relative to the inner slider 5112. When a user pulls on the outer sleeve to remove the stem from the vagina, the outer sleeve can extend away from the petals, and the pessary can collapse. As the pessary collapses, the petals can fold upwards for ease of removal. In various embodiments, the outer sleeve can be provided with a string 5118, so that a user can pull on the string in removing the pessary.

FIG. 51D is a partial perspective view of an upper portion of a pessary with a sliding ring, according to another embodiment. Turning to FIGS. 48 and 51D, the upper portion of a pessary as shown in FIG. 51D can be adapted for use with a sliding ring and stem as shown in FIG. 48. A pessary 51D can have a sliding ring that can be free of a locking mechanism. A pessary 5110 can have a plurality of rigid or semi rigid petals 5112 that can be rotatably connected to a fixed upper ring 5114, pins, or other rotatable hinging mechanisms. Petals 5112 can have an upper hinge 5116 where petal members rotate around a ring 5114, a middle hinge 4808 that can include a pin or other rotating hinge, and a lower hinge 4810 at or near sliding ring 4812. In various embodiments a silicone overmolding, or other soft material can surround the petals 5112. Sliding ring 4812 can slide along the central stem 4814 to move the pessary 5110 between a deployed state and a collapsed state.

FIG. 51E is a partial perspective view of the upper portion of the pessary of FIG. 51D shown in a collapsed state, according to the embodiment. A user can slide the sliding ring 4812 downwards to transform the pessary 5110 into the collapsed state with a minimum diameter for insertion. After the pessary has been inserted, the user can slide the sliding ring upwards to transform the pessary into the deployed state. After the pessary 5110 has been inserted and is in the deployed conformation, the pessary can remain in the deployed, supportive state shown in FIG. 38A due to the placement of the pessary 5110 in the body and the natural distribution of forces within the body. The majority of forces acting on the pessary 5110 while the pessary is in the deployed conformation within the body are exerted downwards on the pessary, thereby maintaining the pessary in a stable and supportive deployed conformation. The tops of the petals 5112 can be cut or otherwise manufactured with interlocking angled ends 5118 so that in the deployed state they can meet at the apex to form a smooth dome top.

FIG. 52 is a top view of a pessary with a rotating ring lock, according to an illustrative embodiment. A pessary 5200 can have a plurality of broad petals 5202 that can support the pelvic organs. Petals 5202 can be attached to a stem 5204 at flexible joints 5206. A rotating ring lock 5208 can have extended locking portions 5210 and notches 5212. The extended locking portions 5210 can extend radially outward beyond the flexible joints 5206 to support the petals 5202. In various embodiments the pessary can have a silicone overmolding that forms a webbing between the petals. The rotating ring lock 5208 can be rotated in the direction of arrow 5214 to unlock the pessary 5200. When the notches 5212 are under the flexible joints 5206 the petals 5202 can fold downwards into the collapsed position. FIG. 53 is a cross sectional view of the pessary with a rotating ring lock taken along cross section line 53-53 of FIG. 52, according to an illustrative embodiment. An extended locking portion 5210 is shown extending under the petal 5202 and supporting the petal 5202 in the deployed state.

FIG. 54 is a top view of a pessary with a rotating ring lock in a collapsed state, according to an illustrative embodiment. The rotating ring 5208 lock has been rotated around the stem 5204 so that the notches 5212 are under the flexible joints 5206. Petals 5202 are bent downwards through the notches 5212 into the collapsed state. FIG. 55 is a cross sectional view of the pessary of with a rotating ring lock in a collapsed state, taken along cross section line 55-55 of FIG. 54, according to an illustrative embodiment. Petals 5202 can be flexed downward into the collapsed state, and the extend locking portions can extend outward between the petals 5202 without interfering with the petals 5202 folding downward into the collapsed state.

FIG. 56 is a perspective view of a pessary with a twisting deployment shown in a deployed state, according to an illustrative embodiment. A pessary 5600 can have a plurality of three or more petals 5602. The upper ends of the petals 5602 can be flexibly joined to the top of the stem 5604, and petals can have a hinge 5606. The lower ends of the petals 5602 can be flexibly joined to a sliding and rotating ring 5608 that can slide along and rotate around the stem 5604. The pessary 5600 can have a silicone overmolding 5610 connecting the petals 5602 to form a supportive webbing between the petals 5602.

FIG. 57 is a perspective view of the pessary with a twisting deployment shown in a collapsed state, according to an illustrative embodiment. Ring 5608 can be slid downward along arrow 5702 and can be rotated along arrow 5704 to transition the pessary 5600 into the collapsed state. In the collapsed state, petals 5602 can be elongated and twisted around the stem 5604 to minimize the diameter of the pessary 5600.

FIG. 58 is a perspective view of the pessary with a twisting deployment of FIG. 56 showing a locking mechanism, according to an illustrative embodiment. In FIG. 58, only two petals 5602 are shown for clarity, but it should be clear that pessary 5600 can have more than two petals. Stem 5604 can have spiral grooves 5802, and ring 5608 can have one or more threads that can slide within the spiral grooves 5802, so that the ring 5608 can be guided through the motion up and down the stem 5604 and the rotational motion around the stem 5604 at the same time. The stem 5604 can have one or more locking bumps 5802 that extend outwards from the stem 5604. Stem 5604 can be hollow and/or flexible, and stem 5604 can flex to allow the sliding ring 5608 to pass over the locking bumps 5802. The locking bumps 5802 can retain the sliding ring 5608 in the upward position, thereby locking the petals 5602 in the deployed state extending radially outward from the stem 5604. A user can release the pessary 5600 from the deployed state by squeezing the stem 5604 inward along arrows 5806, so that the sliding ring 5608 can pass over the locking bumps 5802 and can slide downward on the stem 5604 into the collapsed state.

FIG. 59 is a partially cut away perspective view of the pessary with a twisting deployment of FIG. 56 showing the interior of the petals, according to an illustrative embodiment. In FIG. 59, only two petals 5602 are shown for clarity, but it should be clear that pessary 5600 can have more than two petals. Petals 5602 can have rigid floats 5902 within the petals 5602, and the petals can include a silicone overmolding 5904 that contains the rigid floats 5902. Silicone overmolding 5904 can form the flexible joints between the top of the petals 5602 and the stem 5604, the flexible joints between the bottom of the petals 5602 and the ring 5608, and the joints 5606 in the petals 5602.

FIG. 60 is a perspective view of the pessary with a twisting deployment of FIG. 56 showing living hinges, according to an illustrative embodiment. In various embodiments, the petals 5602 can be molded together as one part along with the sliding and rotating ring 5608 and a fixed ring 6002. The fixed ring 6002 can be fixedly attached to the top of the stem 5604, so that the tops of the petals 5602 are held in a fixed position relative to the top of the stem, and the petals can have flexible joints where the petals meet the fixed ring. Petals 5602 can have living hinges as part of the unitary structure between the petals 5602 and the fixed ring 6002, and the petals can have living hinges as part of the unitary structure between the petals 5602 and the sliding and rotating ring 5608. Petals 5602 can also have unitary living hinges at hinge 5606.

It should be clear to one of ordinary skill that the foregoing describes various embodiments of pessaries that can flexible and can assume a smaller diameter during insertion and removal for greater convenience and comfort. The functions of the pessary and the variable geometry of the diameter can provide for easier handling by the user. This in turn can allow the user to provide their own personal care for the pessary without visiting a health practitioner, greater spontaneity for intimacy, and the ability to remove the pessary when not needed. In various embodiments, an overmolding of silicone or other flexible material can form a webbing between petals to create a supportive structure that can be collapsed during removal.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, in other embodiments for insertion purposes, the pessary can include an applicator that wholly or partially encases the pessary in its collapsed state. The upward and downward motion of the plunger, as well as insertion and removal of the pessary, can be accomplished by manipulation of an applicator. The removal of the pessary can be performed with an assisting applicator. The applicator can be a string in further embodiments. The petals can be formed in a variety of geometries that all have in common the reduction of diameter in the collapsed state. Also, as used herein, various directional and orientational terms (and grammatical variations thereof) such as "vertical", "horizontal", "up", "down", "bottom", "top", "side", "front", "rear", "left", "right", "forward", "rearward", and the like, are used only as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Accordingly, this description is meant to be taken only by way of example, and not to otherwise limit the scope of this invention.

What is claimed is:

1. A pessary comprising:
    a stem including an insertion end and a bottom end, the stem including a shelf at the insertion end; and
    at least one petal member hingedly attached to the insertion end of the stem, the at least one petal member being rotatable between a collapsed state and a deployed state, wherein in the deployed state the at least one petal member extends outward from the stem, and in the collapsed state the at least one petal member is rotated upwards, towards a top end of the pessary, so that a collapsed diameter of the pessary in the collapsed state is smaller than a deployed diameter of the pessary in the deployed state,
    wherein when the pessary is in the deployed state, a surface of the at least one petal member, facing the bottom end, is supported by the shelf.

2. The pessary of claim 1, further comprising a plunger that moves within the stem along a vertical axis of the stem, wherein the plunger can slide away from the insertion end of the stem to allow the at least one petal member to rotate upwards into the collapsed state, and the plunger can slide towards the insertion end of the stem to push the at least one petal member into the deployed state.

3. The pessary of claim 2, wherein the at least one petal member comprises an elongated segment, a short segment, and a bend between the elongated segment and the short segment, the elongated segment and the short segment being at a fixed angle relative to each other.

4. The pessary of claim 3, wherein when the plunger is pushed towards the insertion end of the stem, a top of the plunger pushes upwards on the short segment causing the at least one petal member to rotate into the deployed state with the elongated segment extending outwards from the stem.

5. The pessary of claim 3, further comprising a connection between the top of the plunger and the short segment of the at least one petal member, wherein when the plunger is pulled away from the insertion end of the stem, the top of the plunger pulls the short segment inwards and downwards, thereby rotating the elongated segment upwards into the collapsed state.

6. The pessary of claim 3, further comprising a deformable membrane that is connected to and located between a plurality of short segments.

7. The pessary of claim 6, wherein the deformable membrane is connected to the top of the plunger.

8. The pessary of claim 3, wherein the at least one short segment is connected to the top of the plunger.

9. The pessary of claim 3, the at least one petal member further comprising a tab at the bend, and the plunger cap further comprising at least one groove, wherein when the pessary is in a deployed state, the tab is engaged with the groove.

10. The pessary of claim 2, further comprising a stem cap, wherein in a deployed position, the short segment is held between the plunger and the stem cap, thereby preventing the petal member from rotating out of the deployed position.

11. The pessary of claim 2, the petal member further comprising an intermediate segment, wherein in a deployed state, the plunger can prevent the short segment from rotating upwards, thereby preventing the petal member from over-rotating out of the deployed position, and the plunger can prevent the intermediate segment from rotating inwards, thereby preventing the petal member from rotating back to the collapsed state.

12. The pessary of claim 1, further comprising at least one sliding hinge between the stem and the at least one petal member, the at least one sliding hinge hingedly attached to the at least one petal member, and the at least one sliding hinge slidably attached within the interior of the stem, the sliding hinge sliding along the interior of the stem in a direction parallel to the vertical axis.

13. The pessary of claim 1, wherein the at least one petal member comprises at least two petal members, the pessary further comprising a petal webbing between the petal members, the petal members and the petal webbing forming a unitary petal member.

14. The pessary of claim 1, wherein the at least one petal member comprises at least two petal members, the pessary further comprising an outer rim, wherein the outer rim connects the at least two petal members, thereby forming a unitary petal member.

15. The pessary of claim 1, wherein in the collapsed state the at least one petal member is substantially parallel to a vertical axis of the stem.

* * * * *